(12) United States Patent
Trotta

(10) Patent No.: US 7,829,503 B2
(45) Date of Patent: Nov. 9, 2010

(54) METHODS OF IDENTIFYING COMPOUNDS THAT TARGET TRNA SPLICING ENDONUCLEASE AND USES OF SAID COMPOUNDS AS ANTI-FUNGAL AGENTS

(75) Inventor: Christopher R. Trotta, Somerset, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 533 days.

(21) Appl. No.: 10/551,304

(22) PCT Filed: Mar. 26, 2004

(86) PCT No.: PCT/US2004/009574

§ 371 (c)(1),
(2), (4) Date: May 18, 2006

(87) PCT Pub. No.: WO2004/087070

PCT Pub. Date: Oct. 14, 2004

(65) Prior Publication Data

US 2006/0269923 A1 Nov. 30, 2006

Related U.S. Application Data

(60) Provisional application No. 60/458,090, filed on Mar. 27, 2003.

(51) Int. Cl.
*C40B 30/06* (2006.01)
*C40B 40/08* (2006.01)
*A61K 31/00* (2006.01)

(52) U.S. Cl. .............................................. 506/10; 435/6

(58) Field of Classification Search ....................... None
See application file for complete search history.

(56) References Cited

U.S. PATENT DOCUMENTS

| 4,987,071 A | 1/1991 | Cech et al. |
| 5,093,246 A | 3/1992 | Cech et al. |
| 5,310,664 A | 5/1994 | Butow et al. |
| 5,354,855 A | 10/1994 | Cech et al. |

(Continued)

FOREIGN PATENT DOCUMENTS

| CA | 1340280 | 12/1998 |

(Continued)

OTHER PUBLICATIONS

Abelson et al., 1998, "tRNA splicing." Journal of Biological Chemistry 273(21):12685-12688.

Adams et al., 1991, "Fluorescence ratio imaging of cyclic AMP in single cells." Nature 349:694-697.

(Continued)

*Primary Examiner*—Jeffrey S Lundgren
*Assistant Examiner*—Christian Boesen
(74) *Attorney, Agent, or Firm*—Jones Day

(57) ABSTRACT

The present invention relates to a method for screening and identifying compounds that modulate the activity of a fungal tRNA splicing endonuclease. In particular, the invention provides assays for the identification of compounds that inhibit or reduce the activity of a fungal tRNA splicing endonuclease. The methods of the present invention provide a simple, sensitive assay for high-throughput screening of libraries of compounds to identify pharmaceutical leads useful for preventing, treating, managing and/or ameliorating a fungal infection or fungal infestation or one or more symptoms thereof.

12 Claims, 1 Drawing Sheet

HTS Fluorescent Screening

U.S. PATENT DOCUMENTS

Figure 1:
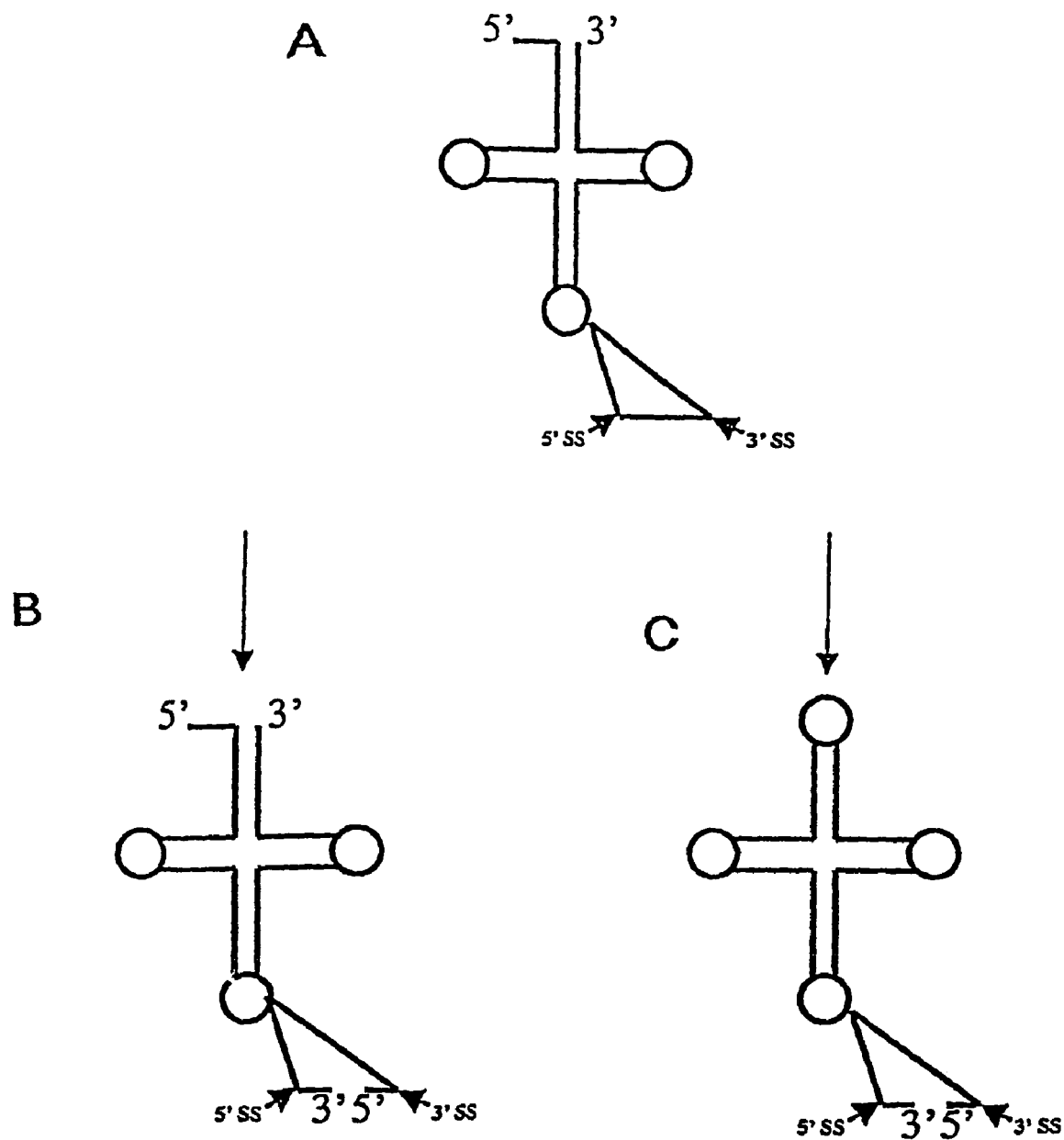

| | | | |
|---|---|---|---|
| 5,439,797 | A | 8/1995 | Tsien et al. |
| 5,591,610 | A | 1/1997 | Cech et al. |
| 5,726,195 | A | 3/1998 | Hill et al. |
| 5,776,738 | A | 7/1998 | Dell'Orco, Sr. |
| 5,939,288 | A | 8/1999 | Thornburg |
| 5,994,124 | A | 11/1999 | Bozzoni |
| 6,025,167 | A | 2/2000 | Cech et al. |
| 6,180,399 | B1 | 1/2001 | Cech et al. |
| 6,214,563 | B1 | 4/2001 | Negulescu et al. |
| 6,221,587 | B1 | 4/2001 | Ecker et al. |
| 6,221,612 | B1 | 4/2001 | Knapp et al. |
| 6,232,070 | B1 | 5/2001 | Shuman |
| 6,446,032 | B1 | 9/2002 | Schimmel |
| 6,503,713 | B1 | 1/2003 | Rana et al. |
| 6,583,309 | B1 | 6/2003 | Rana et al. |
| 6,875,736 | B2 | 4/2005 | Rana et al. |
| 2004/0023239 | A1 | 2/2004 | Tocchini-Valentini et al. |
| 2004/0219545 | A1 | 11/2004 | Rando et al. |
| 2005/0053985 | A1 | 3/2005 | Trotta |
| 2005/0142545 | A1 | 6/2005 | Conn et al. |
| 2005/0221368 | A1 | 10/2005 | Rana et al. |
| 2006/0194234 | A1 | 8/2006 | Conn et al. |
| 2006/0228730 | A1 | 10/2006 | Rando et al. |
| 2007/0020630 | A1 | 1/2007 | Trotta |
| 2007/0178456 | A1 | 8/2007 | Trotta |

FOREIGN PATENT DOCUMENTS

| | | |
|---|---|---|
| CN | 1328156 | 12/2001 |
| EP | 0177827 | 11/1993 |
| WO | WO 91/09942 | 7/1991 |
| WO | WO 98/49274 | 11/1998 |
| WO | WO 99/20795 | 4/1999 |
| WO | WO 00/67580 | 11/2000 |
| WO | WO 01/12820 | 2/2001 |
| WO | WO 01/25486 | 4/2001 |
| WO | WO 01/53455 | 7/2001 |
| WO | WO 01/92463 | 12/2001 |
| WO | WO 02/040685 | 5/2002 |
| WO | WO 02/042326 | 5/2002 |
| WO | WO 02/083837 | 10/2002 |
| WO | WO 02/083953 | 10/2002 |
| WO | WO 04/001010 | 12/2003 |
| WO | WO 2004/087069 | 10/2004 |
| WO | WO 2004/087070 | 10/2004 |
| WO | WO 2004/087884 | 10/2004 |
| WO | WO 2005/003316 | 1/2005 |

OTHER PUBLICATIONS

Belford et al., 1993, "Multiple nucleotide cofactor use by yeast ligase in tRNA splicing. Evidence for independent ATP- and GTP-binding sites" J. Biol. Chem. 268(4):2444-2450.

Belfort, M., & Weiner, A., 1997, "Another bridge between kingdoms: tRNA splicing in archaea and eukaryotes." Cell 89(7):1003-1006.

Bjork, G., 1995, "Biosynthesis and Function of Modified Nucleosides, in tRNA: Structure, Biosynthesis and Function." D. Soll & U. RajBhandary (eds.), American Society for Microbiology, Washington DC: pp. 165-205.

Deutscher, M.P. , 1995 "tRNA Processing Nucleases, in tRNA:Structure, Biosynthesis and Function." D. Soll and U. RjaBhandary (eds.), American Society for Microbiology, Washington DC: pp. 51-65.

Diener & Moore, 1998, "Solution Structure of a Substrate for the Archael Pre-tRNA Splicing Endonucleases: The Bulge-Helix-Bulge Motif." Mol. Cell. 1:883-894.

Fruscoloni et al., 2001, "Cleavage of non-tRNA substrates by eukaryal tRNA splicing endonucleases." EMBO Rep 2(3):217-221.

Gomes et al., 1997, "RNA splicing ligase activity in the archaeon Haloferax volcanii" Biochem & Biophys. Res. Comm. 237:588-94.

Greer et al., 1982, "Mechanism of action of a yeast RNA ligase in tRNA splicing" Cell 32:537-546.

Greer., 1986, "Assembly of tRNA Splicing Complex: Evidence for Concerted Excision and Joining Steps in Splicing In Vitro." Mol. and Cellular. Bio., 6(2):638-642.

Hyde-Deruyscher et al., 2000, "Detection of Small-Molecule Enzyme Inhibitors with Peptides Isolated from Phage-Displayed Combinatorial Peptide Libraries." Chem. & Biol. 7:17-25.

Ikemura, 1985, "Codon Usage and tRNA Content in Unicellular and Multicellular Organisms." Mol. Biol. Evol., 2(1):13-34.

Ikemura, T. And Okeki, H., 1983, "Codon usage and transfer RNA contents: organism-specific codon-choice patterns in reference to the isoacceptor contents." Cold Spring Harbor Symp. Quant. Biol. 47:1087-1097.

Kleman-Leyer et al., 1997, "Properties of H. volcanii tRNA Intron Endonuclease Reveal a Relationship between the Archaeal and Eucaryal tRNA Intron Processing Systems." Cell., 89:839-847.

Li & Abelson, 2000, "Crystal Structure of a Dimeric Archaeal Splicing Endonuclease." J. Mol. Biol. 302:639-648.

Li et al., 1998, "Crystal structure and evolution of a transfer RNA splicing enzyme" Science 280(5361):279-284.

Lykke-Andersen, J. & Garrett, R.A.., 1997, "RNA-protein interactions of an archaeal homotetrameric splicing endoribonuclease with an exceptional evolutionary history." EMBO J 16(20):6290-6300.

Phizicky et al., 1986, "Saccharomyces cerevisiae tRNA ligase. Purification of the protein and isolation of the structural gene" J. of Biol. Chem. 261(6):2978-2986.

Qin & Pyle, 1999, "Site-specific labeling of RNA with fluorophores and other structural probes." Methods 18 (1):60-70.

Reyes & Abelson 1988, "Substrate Recognition and Splice Site Determination in Yeast tRNA Splicing." Cell, 55:719-730.

Sarkar & Hopper., 1998, "tRNA Nuclear Export in *Saccharomyces cerevisiae*: In Situ Hybridization Analysis." Mol. Biol. of the Cell., 9:3041-3055.

Saxena et al., 1992, "Angiogenin is a Cytotoxic, tRNA-specific Ribonuclease in the RNase A Superfamily." J. of Biol. Chem. 267(30):21982-21986.

Trotta et al., 1997, "The yeast tRNA splicing endonuclease: a tetrameric enzyme with two active site subunits homologous to the archaeal tRNA endonucleases." Cell 89:849-858.

Trotta, C.R. And Abelson, J.N., 1999, "tRNA Splicing: An RNA World Add-On or an Ancient Reaction? In RNA World II" Tom Cech, Ray Gesteland and John Atkins (eds.), Cold Spring Harbor Laboratory Press, 561-584.

Trotta., 1999, "The Composition, Function and Evolution of the tRNA Splicing Endonuclease." Thesis, California Institute of Technology, pp. 1-147.

Tsien et al., 1993, "FRET for studying intracellular signaling." Trends in Cell. Bio. 3(7): 242-245.

Vaughn et al., 2002, "Methonine In and Out of Proteins: Targets for Drug Design." Curr. Med. Chem. 9(3):385-409.

Volarevic et al., 2000, "Proliferation, But not Growth Blocked by Conditional Deletion of 40S Ribosomal Protein S6." Science 288:2045-2047.

Wang et al., 1990, "Substrate Masking: Binding of RNA by EGTA-Inactivated Micrococcal Nuclease Resutls in Artifactual Inhibition of RNA Processing Reactions." Nuc. Acids Res. 18(22):6625-6626.

Winter et al., 2000, "RNA polymerase III transcription factor TFIIIC2 is overexpressed in ovarian tumors." Proc. Natl. Acad. Sci., 97(23):12619-12624.

Xu et al., 1990, "Purification of yeast transfer RNA ligase." Meth. in Enzymol. 181:463-471.

Zhang et al., 1997, "Gene Expression Profiles in Normal and Cancer Cells." Science 276:1268-1272.

Baldi et al., 1992, "Participation of the intron in the reaction catalyzed by the Xenopus tRNA splicing endonuclease." Science 255:1404-1408.

Barbino & Kelller, 1999, "Last but not least: regulated poly(A) tail formation." Cell 99(1):9-11.

Bujnicki, J.M., & Rychlewski, L., 2000, "Prediction of a common fold for all four subunits of the yeast tRNA splicing endonuclease: implications for the evolution of the EndA/Sen family." FEBS Lett 486: 328-329.

Buvoli et al, 2000, "Suppression of nonsense mutations in cell culture and mice by multimerized suppressor tRNA genes" Molecular and Cellular Biology 20(9):3116-3124.

Calvo, O., and Manley, J.L., 2003, "Strange bedfellows: polyadenylation factors at the promoter." Genes Dev 17(11):1321-1327.

Choi and Dreyfuss, 1984, "Monoclonal antibody characterization of the C proteins of heterogeneous nuclear ribonucleoprotein complexes in vertebrate cells." J. Cell. Biol. 99(6):1997-2004.

Culver et al., 1997, "A 2'-phosphotransferase implicated in tRNA splicing is essential in *Saccharomyces cerevisiae*." J Biol Chem 272:13203-13210.

De Vries, H. et al., 2000, "Human pre-mRNA cleavage factor II(m) contains homologs of yeast proteins and bridges two other cleavage factors." EMBO J 19:5895-5904.

Fabbri, S et al., 1998, "Conservation of substrate recognition mechanisms by tRNA splicing endonucleases." Science 280, 284-286.

Frank & Pace, 1998, "Ribonuclease P: unity and diversity in a tRNA processing ribozyme." Annu Rev Biochem 67, 153-180.

Gandini-Attardi, et al., 1990, "Transfer RNA splicing endonuclease from *Xenopus laevis*." Methods Enzymol 181:510-517.

Hirose and Manley, 2000, "RNA polymerase II and the integration of nuclear events." Genes Dev., 14(12):1415-1429.

Hopper, A.K., and Phizicky, E.M., 2003, "tRNA transfers to the limelight." Genes Dev 17(2):162-180.

Huh, et al., 2003, "Global analysis of protein localization in budding yeast." Nature 425:686-691.

Jacobson et al., 1997, "Nuclear domains of the RNA subunit of RNase P." J Cell Sci. 110 (Pt 7):829-837.

Laski, F.A. et al., 1983, "Characterization of tRNA precursor splicing in mammalian extracts." J Biol. Chem. 258(19):11974-11980.

Minvielle-Sebastia, L. & Keller, W., 1999, "mRNA polyadenylation and its coupling to other RNA processing reactions and to transcription." Curr. Opin. Cell. Biol. 11:352-357.

O'Connor, J.P., & Peebles, C.L., 1992, "PTA1, an essential gene of *Saccharomyces cerevisiae* affecting pre-tRNA processing." Mol Cell Biol 12:3843-3856.

Otsuka, et al., 1981, "Ribonuclease 'XlaI' an activity from Xenopus laevis oocytes that excises intervening sequences from yeast transfer ribonucleic acid precursors." Mol Cell Biol 1:269-280.

Park & Bhandary, 1998, "Tetracycline-regulated suppression of amber codons in mammalian cells." Mol. & Cell. Biol. 18:4418-4425.

Preker et al., 1997, "A multisubunit 3'-end processing factor from yeast containing poly(A) polymerase and homologues of the subunits of mammalian cleavage and polyadenylation specificity factor." EMBO J 16:4727-4737.

Proudfoot, 2000, "Connecting transcription to messenger RNA processing." Trends Biochem Sci. Jun. 2000;25(6):290-3. Review.

Rauhut et al., 1990, "Yeast tRNA-splicing endonuclease is a heterotrimeric enzyme." J Biol. Chem. 265(30): 18180-18184.

Reyes et al., 1987, "A synthetic substrate for tRNA splicing." Anal. Biochem. 166(1):90-106.

Standring et al., 1981, "Yeast tRNA3Leu gene transcribed and spliced in a HeLa cell extract." Proc. Natl. Acad. Sci. USA 78(10):5963-5967.

Takagaki et al., 2000, "Complex protein interactions within the human polyadenylation machinery identify a novel component." Mol. Cell. Biol. 20:1515-1525.

Takaku et al., 2003, "A candidate prostate cancer susceptibility gene encodes tRNA 3' processing endoribonuclease." Nucleic Acids Res 31(9):2272-2278.

Wahle & Ruegsegger, 1999, "3'-End processing of pre-mRNA in eukaryotes." FEMS Micro Rev., 23(3):277-295.

Wallace et al., 1999, "Two distinct forms of the 64,000 Mr protein of the cleavage stimulation factor are expressed in mouse male germ cells." Proc. Natl. Acad. Sci. 96(12):6763-6768.

Xiao et al., 2002, "Eukaryotic ribonuclease P: a plurality of ribonucleoprotein enzymes." Annu Rev Biochem 71, 165-189.

Yoshihisa et al., 2003, "Possibility of cytoplasmic pre-tRNA splicing: the yeast tRNA splicing endonuclease mainly localizes on the mitochondria." Mol Biol Cell 14(8):3266-3279.

Zhao, 1999 "Formation of mRNA 3' ends in eukaryotes: mechanism, regulation, and interrelationships with other steps in mRNA synthesis." Microbiol. Mol. Biol. Rev. 63:405-445.

Miao et al., 1993, "Yeast tRNA-splicing endonuclease cleaves precursor tRNA in a random pathway," J. Biol. Chem. 268(1):672-7.

Greer et al., 1987, "Substrate recognition and identification of splice sites by the tRNA-splicing endonuclease and ligase from Saccharomyces cerevisiae." Mol. & Cell. Biol. 7(1): 76-84.

Phizicky et al., 1992, "Yeast tRNA Ligase Mutants are Nonviable and Accumulate tRNA Splicing Intermediates." J. Biol. Chem. 267(7):4577-4582.

Zillman et al., 1991, "Conserved mechanism of tRNA splicing in eukaryotes." Mol. & Cell. Biol. 11(11):5410-5416.

Branden et al., 1991. Chapter 16: Prediction, Engineering, and Design of Protein Structures in Introduction to Protein Structure, Garland Publishing, Inc., p. 247.

Brown, 1993, Hybridization Analysis of DNA Blots, in Current Protocols in Molecular Biology, p. 2.10.1-2.10.11.

Genbank Accesion No: AAH19582, "TRNA splicing" dated Jan. 3, 2002.

Genbank Accession No,: BC019582, "*Homo sapiens* TRNA" dated Jan. 3, 2002.

Genbank Accession No. CAA19575, "tRNA-splicing endonuclease subunit Sen34 [Schizosaccharomyces pombe]," dated Jun. 30, 2009.

Genbank Accession No. CAA21061, "tRNA-splicing endonuclease subunit Sen54 (predicted) [Schizosaceharoinyces pombe]." dated Jun. 30, 2009.

Genbank Accession No. CAD27500, "tRNA-splicing endonuclease subunit Sen2 [*Schizosaccharomyces pombe*]," dated Jun. 30, 2009.

Genbank Accession No. CAE46913; "tRNA-splicing endonuclease subunit Sen 15 [*Schizosaccharomyces pombe*]," dated Jun. 30, 2009.

Genbank Accession No. NP 079541; "tRNA splicing endonuclease 2 homolog [*Homo sapiens*]," dated Mar. 2, 2006.

Genbank: Accession No. NT_005927.I2; "*Homo sapiens* chromosome 3 reference genomic contig," dated Aug. 1, 2002.

Genbank: Accession No: NT_011225.9; "*Homo sapiens* chromosome 19 reference genomic contig," dated Aug. 1, 2002.

Genbank: Accession No. XP_085899; "similar to LENG5 protein [*Homo sapiens*]," dated Aug. 1, 2002.

Greer, 1986, "Assembly of a tRNA splicing complex: evidence for concerted excision and joining steps in splicing in vitro." Mol Cell Biol. 6:635-644.

Herrenknecht, 1988, "Pre t-RNA splicing in a nuclear extract from human leukemia cells: separation of endonuclease and ligase activities." Nuc. Acids Res. 16:7713-7714.

Kaminska, 2002, "The isoprenoid biosynthetic pathway in *Saccharomyces cerevisiae* is affected in a mafl-1 mutant with altered tRNA synthesis." FEMS Yeast Res. 2:31-37.

Lucas et al., 2000, "Yeast Sequencing Report: Sequence analysis of two cosmids from the right arm of the *Schizosaccharomyces pombe*chromosome II." Yeast 16:229-306.

Marras, 2002, "Efficiences of Fluorence Resonance Energy transfer and contact-mediated quenching in oligonucelotide probes." Nucleic Acids Res. 30:1-8.

Paushkin et al., 2004, "Identification of a human endonuclease complex reveals a link between tRNA splicing and pre-mRNA 3' End Formation." Cell, 117:311-321.

Seffernick et al., 2001, "Melamine deaminase and atrazine chlorohydrolase: 98 percent identical but functionally different." J Bacteriol 183(8):2405-2410.

Sood et al., 2001, "Cloning and characterization of 13 novel transcripts and the human RGS8 gene from the Iq25 region encompassing the hereditary prostate cancer (HPC1) locus." Genomics 73:211-222.

Spaltmann et al., 1999, "Computer-aided target selection—prioritizing targets for antifungal drug discovery." DDT, 4(1):17-26.

Stryer, 1999, Chapter 5: Flow of Genetic Information, p. 96-97; Chapter 33: RNA Synthesis and Splicing, p. 860-864, Chapter 34: Protein Synthesis, p. 875-880: in Biochemistry, $4^{th}$ edition, W.H. Freeman and Co., New York.

Witkowski, 1999, "Converstion of β-ketaoacyl Synthase to Malonyl Decarboxylase by Replacement of the Active-site Cysteine and Glutamine." Biochemistry, 38:11643-11650.

Yeast Accession No. YLR1O5C; SEN2: http://www.yeastgenome.org/, dated Mar. 8, 2006.

Yeast Accession No. YAR008w; SEN34 http://www.yeastgenome.org/, dated Mar. 8, 2006.

Yeast Accession No. YMR059w; SEN 15 http://www.yeastgenome,org/ dated Mar. 8, 2006.

Yeast Accession No: YPL083c; SEN54 "http://www.yeastgenome.org/," dated Mar. 8, 2006.

Response To Office Communication Regarding Sequence Disclosure and Preliminary Amendment dated Feb. 28, 2006. for U.S. Appl. No. 10/884,695, filed Jul. 2, 2004.

Requirement Restriction/Election dated Jun. 13, 2006 for U.S. Appl. No. 10/884,695, filed Jul. 2, 2004.

Response to Requirement for Restriction/Election and Preliminary Amendment dated Oct. 13, 2006 for U.S. Appl. No. 10/884,695, filed Jul. 2, 2004.

Non-Final Rejection, dated Dec. 21, 2006, for U.S. Appl. No. 10/884,695, filed Jul. 2, 2004.

Amendment after non-final rejection, dated Apr. 17, 2007. For U.S. Appl. No. 10/884,695, filed Jul. 2, 2004.

Non-Final Rejection, dated Jul. 13, 2007, for U.S. Appl. No. 10/884,695, filed Jul. 2, 2004.

Amendment after non-final rejection, dated Nov. 13. 2007, for U.S. Appl. No. 10/884,695, filed Jul. 2, 2004.

Non-Final Rejection, dated Feb. 5, 2008, for U.S. Appl. No. 10/884,695, filed Jul. 2, 2004.

Amendment after non-final rejection, dated Aug. 5, 2008, for U.S. Appl. No. 10/884,695, filed Jul. 2, 2004.

Detailed Action, dated Dec. 1, 2008, for U.S. Application No. 10/884,695, filed Jul. 2, 2004.

Notice of Abandonment, dated Jun. 4, 2009, for U.S. Appl. No. 10/884,695, filed Jul. 2, 2004.

Requirement for Restriction/Election, dated Sep. 8, 2008, for U.S. Appl. No. 10/551,300, filed Nov. 29, 2006.

Response to Restriction Requirement and Preliminary Amendment, dated Nov. 10, 2008, for U.S. Appl. No. 10/551,300, filed Nov. 29, 2006.

Notice of Non-compliant, dated Feb. 4, 2009, for U.S. Appl. No. 10/551,300, filed Nov. 29, 2006.

Response to Notice of Non-compliant, dated Mar. 2, 2009, for U.S. Appl. No. 10/551,300, filed Nov. 29, 2006.

Non-Final Rejection, dated May 22, 2009, for U.S. Appl. No. 10/551,300, filed Nov. 29, 2006.

Preliminary Amendment dated Sep. 27, 2005, for PCT/US2004/009572-U.S. Appl. No. 10/551,301, filed Jul. 12, 2006.

Preliminary Amendment dated Aug. 4, 2008, for U.S. Appl. No. 10/551,301, filed Jul. 12, 2006.

Requirement for Restriction/Election, dated Jan. 16, 2009, for U.S. Appl. No. 10/551,301, filed Jul. 12, 2006.

Response to requirement for Restriction/Election, dated Feb. 17, 2009, for U.S. Appl. No. 10/551,301, filed Jul. 12, 2006.

Non-Final Rejection, dated May 12, 2009, for U.S. Appl. No. 10/551,301, filed Jul. 12, 2006.

International Search Report, dated Jun. 22, 2005 of PCT/US2004/009572, filed Mar. 26, 2004.

Written Opinion, dated Jun. 22, 2005 of PCT/US2004/009572, filed Mar. 26, 2004.

International Preliminary Report on Patentability, dated Nov. 11, 2005 of PCT/US2004/009572, filed Mar. 26, 2004.

European Search Report, dated Jul. 23, 2007 of EP 1 613 158 published Jan. 11, 2006.

International Search Report, dated Jan. 27, 2005 of PCT/US2004/009590, filed Mar. 26, 2004.

Written Opinion, dated Jan. 27, 2005 of PCT/US2004/009590, filed Mar. 26, 2004.

International Preliminary Report on Patentability, dated Jun. 16, 2005 of PCT/US2004/009590, filed Mar. 26, 2004.

European Search Report, dated Jul. 23, 2007 of EP 1 613 160 published Jan. 11, 2006.

International Search Report, dated Apr. 24, 2007 of PCT/US2004/021334, filed Jul. 2, 2004.

Written Opinion, dated Apr. 24, 2007 of PCT/US2004/021334, filed Jul. 2, 2004.

International Preliminary Report on Patentability, Dec. 12, 2007 of PCT/US2004/021334, filed Jul. 2, 2004.

European Search Report, dated May 8, 2009 of EP 1 649 002 published Apr. 26, 2006.

International Search Report, dated Jun. 9, 2005 of PCT/US2004/009574, filed Mar. 26, 2004.

Written Opinion, dated Jun. 9, 2005 of PCT/US2004/009574, filed Mar. 26, 2004.

International Preliminary Report on Patentability, dated Nov. 11, 2005 of PCT/US2004/009574, filed Mar. 26, 2004.

European Search Report, dated Jul. 3, 2007 of EP 1 613 159 published Jan. 11, 2006.

European communication regarding possible amendment of claims/payment of fees, dated Nov. 14, 2005, of EP 1 613 158, published Jan. 11, 2006.

Reply to European communication before examination dated Dec. 21, 2005, of EP 1 613 158, published Jan. 11, 2006.

European communication regarding transmission of search report, dated Jul. 23, 2007, of EP 1 613 158, published Jan. 11, 2006.

European communication from the examining division, dated Nov. 16, 2007, of EP 1 613 158, published Jan. 11, 2006.

Reply to European communication from the examining division, dated May 15, 2008, of EP 1 613 158, published Jan. 11, 2006.

European communication from the examining division, dated Jul. 15, 2008, of EP 1 613 158, published Jan. 11, 2006.

Reply to European communication from the examining division, dated Nov. 14, 2008, of EP 1 613 158, published Jan. 11, 2006.

European communication from the examining division, dated Nov. 26, 2008, of EP 1 613 158, published Jan. 11, 2006.

Reply to European communication from the examining division, dated Jan. 23, 2009, of EP 1 613 158, published Jan. 11, 2006.

European communication regarding possible amendment of claims/payment of fees, dated Nov. 14, 2005, of EP 1 613 159, published Jan. 11, 2O06.

European communication regarding transmission of search report, dated Jul. 3, 2007, of EP 1 613 159, published Jan. 11, 2006.

European communication from the examining division, dated Oct. 10, 2007, of EP 1 613 159, published Jan. 11, 2006.

Reply to European communication from the examining division, dated Apr. 21, 2008, of EP 1 613 159, published Jan. 11, 2006.

European communication from the examining division, dated Aug. 5, 2008, of EP 1 613 159, published Jan. 11, 2006.

Reply to European communication from the examining division, dated Aug. 18, 2008, of EP 1 613 159, published Jan. 11, 2006.

European communication from the examining division, dated Dec. 17, 2008, of EP 1 613 159, published Jan. 11, 2006.

Reply to European communication from the examining division, dated Jun. 26, 2009, of EP 1 613 159, published Jan. 11, 2006.

European communication regarding possible amendment of claisms/payment of fees, dated Nov. 14, 2005, of EP 1 613 160, published Jan. 11, 2006.

European communication regarding transmission of search report, dated Jul. 23, 2007, of EP 1 613 160, published Jan. 11, 2006.

European communication from the examining division, dated Apr. 23, 2008, of EP 1 613 160, published Jan. 11, 2006.

Reply to European communication from the examining division, dated Oct. 31, 2008, EP 1 613 160, published Jan. 11, 2006.

European communication from the examining division, dated Dec. 17, 2008, of EP 1 613 160, published Jan. 11, 2006.

Reply to European communication from the examining division, dated Jun. 26, 2009, of EP 1 613 160, published Jan. 11, 2006.

Genbank Accession No. M32336. "S.cerevisiae tRNA splicing endonuclease beta-subunit (SEN2) gene. complete cds," dated Aug. 19, 1997.

Spingola et al., 1999. Genome-wide bioinformatic and molecular analysis of introns in *Saccharomyces cerevisiae*, RNA, 5:221-234.

Response to Non-Final Rejection, dated Aug. 19, 2009, for U.S. Appl. No. 10/551,300, filed Nov. 29, 2006.

Response to Non-Final Rejection, dated Sep. 10, 2009, for U.S. Appl. No. 10/551,301, filed Jul. 12, 2006.

Final Rejection, dated Dec. 2, 2009, for U.S. Appl. No. 10/551,300, filed Nov. 29, 2006.

Final Rejection, dated Dec. 9, 2009, for U.S. Appl. No. 10/551,301, filed Jul. 12, 2006.

European communication from the examining division, dated Dec. 1, 2009, of EP 1 613 158, published Jan. 11, 2006.

European communication from the examining division, dated Dec. 1, 2009, of EP 1 613 159, published Jan. 11, 2006.

European communication from the examining division, dated Dec. 1, 2009, of EP 1 613 160, published Jan. 11, 2006.

Kohrer et al., 1990, "A yeast tRNA precursor containing a pre-mRNA intron is spliced via the pre-mRNA splicing mechanism", EMBO J, 9(3):705-9.

US 7,829,503 B2

METHODS OF IDENTIFYING COMPOUNDS THAT TARGET TRNA SPLICING ENDONUCLEASE AND USES OF SAID COMPOUNDS AS ANTI-FUNGAL AGENTS

This application claims benefit of United States Provisional Application No. 60/458,090, filed on Mar. 27, 2003.

1. FIELD OF THE INVENTION

The present invention relates to a method for screening and identifying compounds that modulate the activity of a fungal tRNA splicing endonuclease. In particular, the invention provides assays for the identification of compounds that inhibit or reduce the activity of a fungal tRNA splicing endonuclease. The methods of the present invention provide a simple, sensitive assay for high-throughput screening of libraries of compounds to identify pharmaceutical leads useful for preventing, treating, managing and/or ameliorating a fungal infection or one or more symptoms thereof.

2. BACKGROUND OF THE INVENTION

2.1 Fungal Infection and Related Health Issues

Fungi are eukaryotic microorganisms and can occur as yeasts, molds, or as a combination of both forms. Some fungi are capable of causing superficial, cutaneous, subcutaneous, systemic or allergic diseases. Yeasts are microscopic fungi consisting of solitary cells that reproduce by budding. Molds, in contrast, occur in long filaments known as hyphae, which grow by apical extension. Hyphae can range from sparsely septate to regularly septate and possess a variable number of nuclei. Regardless of their shape or size, fungi are all heterotrophic and digest their food externally by releasing hydrolytic enzymes into their immediate surroundings (absorptive nutrition).

Fungal and other mycotic pathogens (some of which are described in *Human Mycoses*, E. S. Beneke, Upjohn Co.: Kalamazoo, Mich., 1979; *Opportunistic Mycoses of Man and Other Animals* J. M. B. Smith, CAB International: Wallingford, UK, 1989; and *Scrip's Antifungal Report*, by PJB Publications Ltd, 1992) are responsible for a variety of diseases in humans, animals, and plants ranging from mycoses involving skin, hair, or mucous membranes, including, but not limited to, Aspergillosis, Black piedra, Candidiasis, Chromomycosis, Cryptococcosis, Onychomycosis, or Otitis externa (otomycosis), Phaeohyphomycosis, Phycomycosis, Pityriasis versicolor, ringworm, *Tinea barbae, Tinea capitis, Tinea corporis, Tinea cruris, Tinea favosa, Tinea imbricata, Tinea manuum, Tinea nigra* (palmaris), *Tinea pedis, Tinea unguium, Torulopsosis,* Trichomycosis axillaris, White piedra; and severe systemic or opportunistic infections, including, but not limited to, Actinomycosis, Aspergillosis, Candidiasis, Chromomycosis, Coccidioidomycosis, Cryptococcosis, Entomophthoramycosis, Geotrichosis, Histoplasmosis, Mucormycosis, Mycetoma, Nocardiosis, North American Blastomycosis, Paracoccidioidomycosis, Phaeohyphomycosis, Phycomycosis, pneumocystic pneumonia, Pythiosis, Sporotrichosis, and *Torulopsosis*, some among these of which may be fatal.

Known fungal and mycotic pathogens include, but are not limited to, *Absidia* spp., *Actinomadura madurae, Actinomyces* spp., *Allescheria boydii, Alternaria* spp., *Anthopsis deltoidea, Apophysomyces elegans, Arnium leoporinum, Aspergillus* spp., *Aureobasidium pullulans, Basidiobolus ranarum, Bipolaris* spp., *Blastomyces dermatitidis, Candida* spp., *Cephalosporium* spp., *Chaetoconidium* spp., *Chaetomium* spp., *Cladosporium* spp., *Coccidioides immitis, Conidiobolus* spp., *Cornyebacterium tenuis, Cryptococcus* spp., *Cunninghamella bertholletiae, Curvularia* spp., *Dactylaria* spp., *Epidermophyton* spp., *Epidermophyton floccosum, Exserophilum* spp., *Exophiala* spp., *Fonsecaea* spp., *Fusarium* spp., *Geotrichum* spp., *Helminthosporium* spp., *Histoplasma* spp., *Lecythophora* spp., *Madurella* spp., *Malassezia furfur, Microsporum* spp., *Mucor* spp., *Mycocentrospora acerina, Nocardia* spp., *Paracoccidioides brasiliensis, Penicillium* spp., *Phaeosclera dematioides, Phaeoannellomyces* spp., *Phialemonium obovatum, Phialophora* spp., *Phoma* spp., *Piedraia hortai, Pneumocystis carinii, Pythium insidiosum, Rhinocladiella aquaspersa, Rhizomucor pusillus, Rhizopus* spp., *Saksenaea vasiformis, Sarcinomyces phaeomuriformis, Sporothrix schenckii, Syncephalastrum racemosum, Taeniolella boppii, Torulopsosis* spp., *Trichophyton* spp., *Trichosporon* spp., *Ulocladium chartarum, Wangiella dermatitidis,* and *Xylohypha* spp. Other fungi that "obviously have pathogenic potential" (Smith, op. cit.) include, but are not limited to, *Thermomucor indicae-seudaticae, Radiomyces* spp., and other species of known pathogenic genera. There are also reports implicating *Saccharomyces* as a human pathogen (e.g., Fungemia with Saccharomycetacea, H. Nielson, J. Stenderup, & B. Bruun, Scand. J. Infect. Dis. 22:581-584, 1990). To a large extent, fungal infections in humans have been satisfactorily controlled by a human host's immune response mechanisms combined with the aid of conventionally-accepted and readily available antifungal treatments; however, in recent years, there has been a marked increase in the number of serious mycoses as a result of the growing number of immunosuppressed and immunocompromised individuals, such as transplant recipients, patients receiving chemotherapy, and HIV-infected individuals, and thus greater attention has been devoted to the need to develop safer and more effective antifungal agents.

Fungal infection is also a significant problem in veterinary medicine including, but not limited to, candidiasis, cryptococcosis, aspergillosis, mucormycosis, pythiosis, entomophthoramycosis, oomycosis, chromomycosis, *torulopsosis,* infections with *Penicillium* spp., *Trichosporon* spp., *Paecilomyces* spp., *Microsporum* spp., and a variety of miscellaneous/rarer opportunistic mycoses (Opportunistic Mycoses of Man and Other Animals, J. M. B. Smith, CAB International, Wallingford, UK, 1989). Fungal infections are a common cause of nasal disease in dogs and cats (Fungal Diseases of the Nasal Cavity of the Dog and Cat, Wolf, A. M., 1992, Vet. Clin. of North Amer.: Small Anim. Prac. 22, 1119-1132). A variety of fungi, including, but not limited to, *Aspergillus* spp., *Candida* spp., *Paecilomyces* spp., *Penicillium* spp., *Alternaria* spp., *Geotrichum* spp., and *Cladosporium* spp., have been isolated from animal eyes and may cause fungal keratitis in several species including, but not limited to, horses, dogs, and cats (Microbiology of the Canine and Feline Eye, P. A. Gerding and I. Kakoma, 1990, Vet. Clin. of North Amer.: Small Anim. Prac. 20, 615-625). Skin infections by fungi, including, but not limited to, *Microsporum canis, Trichophyton mentagrophytes, Trichophyton verucosum, Microsporum equinum, Microsporum gallinae,* and *Microsporum nanum,* occur in many different animals, both wild and domestic, with some infections being specific to a given host species (Fungal Skin Infections Associated with Animal Contact, W. H. Radentz, 1991, AFP 43, 1253-1256).

Some of the fungi that infect animals can be transmitted from animals to humans. Fungal zoonotic diseases are most commonly associated with animals as pets, with a higher frequency found among veterinary personnel, owing to higher levels of contact with animals (ibid., M. R. Lappin, Vet. Clin. of North Amer.: Small Anim. Prac. 23, 57-78). Topical and systemic antifungal agents are used to treat both humans and animals.

Fungal infections or infestations are also a very serious problem in agriculture with fungicides being employed to protect vegetable, fruit, and nut crops (F. L. McEwen and G. R. Stephenson, 1979, The Use and Significance of Pesticides in the Environment. Wiley, N.Y.). Fungicides are applied to soil, seeds, propagating material, growing plants, and produce to combat pathogens. Seed and soil-borne pathogens include but are not limited to *Aphanomyces* spp., *Armillaria* spp., *Cephalosporium* spp., *Cylindrocladium* spp., *Fusarium* spp., *Helminthosporium* spp., *Macrophomina* spp., *Magnaporthe* spp., *Ophiobolus* spp., *Phymatotrichum* spp., *Phytophthora* spp., *Pythium* spp., *Rhizoctonia* spp., *Scerotium* spp., *Sclerotinia* spp., *Thielaviopsis* spp., *Ustilago* spp., *Verticillium* spp., and *Whetxelinia* spp., (R. Rodriguez-Kabana, P. A. Backman, and E. A. Curl, Control of Seed and Soil-Borne Plant Diseases. In Antifungal Compounds, M. Siegel and H. Sisler, eds., Marcel Dekker Inc., NY, 1977). Post-harvest diseases of fresh fruits and vegetables are caused by fungi including, but not limited to, *Alternaria* spp., *Botrytis* spp., *Centrospora* spp., *Ceratocystis* spp., *Colletotrichum* spp, *Cryptoporiopsis* spp., *Diplodia* spp., *Fusarium* spp., *Helminthosporium* spp. *Monilinia* spp., *Nectria* spp., *Oospora* spp., *Penicillium* spp., *Phlyctaena* spp., *Phoma* spp., *Phomopsis* spp., *Rhizopus* spp., *Sclerotinia* spp., and *Verticillium* spp.

It has been estimated that fungicides are employed in the farming of one-half of the world's crops (G. Ordish and J. F. Mitchell. 1967, World Fungicide Usage. In Fungicides, an Advanced Treatise, Vol. 1, pp. 39-62. D. C. Torgeson, ed. Academic Press, NY) either to control disease during crop development, to improve the storage of produce, or to increase production of a particular crop. Approximately 20% of U.S. non-pasture crop land is treated with fungicides (E. W. Palm, Estimated Crop Losses Without the Use of Fungicides and Nematicides and Without Nonchemical Controls. CRC Handbook of Pest Management in Agriculture, Vol. 1, p. 139f). In economic terms, the cessation of fungicide use would result in losses to field crops, vegetable crops, and fruit and nut crops estimated to total over two billion dollars (ibid.). Some crops would be particularly hard hit, e.g., peanut losses would be expected to be >70% of the total crop, pecan losses >65% of the total crop, tomato losses >60% of the total crop, potato losses >40% of the total crop, and fruits such as apples, cherries, peaches, and pears each >50% of their total crop (ibid.).

Fungal attack of wood products is also of major economic importance with an estimated one billion dollars in damage annually (not including damage to living trees) in the U.S., even with the extensive use of existing preservatives (M. P. Levi, Fungicides in Wood Preservation, In *Antifungal Compounds*, M. Siegel and H. Sisler, eds., Marcel Dekker Inc., NY, 1977). Hundreds of fungal species have been isolated from wood products. Surface molds result from infestation by genera including, but not limited to, *Trichoderma* spp., *Gliocladium* spp., *Penicillium* spp., *Aspergillus* spp., and *Altemaria* spp. Sap stain fungi include, but are not limited to, *Ceratocystis* spp., *Diplodia* spp., *Graphium* spp., *Aureobasidium* spp., and *Cytospora* spp. Decay fungi responsible for a large proportion of the economic losses include, but are not limited to, *Coniophora* spp., *Lentinus* spp., *Lenzites* spp., *Polyporus* spp., *Poria* spp., and *Merulius* spp. Soft-rot fungi include, but are not limited to, *Ascomycetes* spp., *Chaetomium* spp., and Fungi Imperfecti.

Additional products that are susceptible to fungal infestation include textiles, plastics, paper, rubber, adhesives, emulsion polymers, leather, cosmetics, household disinfectants, deodorants, and paint. (C. C. Yeager, Fungicides in Industry, in *Antifungal Compounds*, M. Siegel and H. Sisler, eds., Marcel Dekker Inc., NY, 1977). More work has been done on paint than on any other substrate. Fungi that attack painted surfaces often disfigure the paint film to the point where replacement is required. Repainting can solve the problem only temporarily as the organism may erupt through the new coating. Paint infestations include, but are not limited to, *Pullularia* spp., *Cladosporium* spp., *Aspergillus* spp., and *Penicillium* spp. The only successful method of combating fungal growth on paint systems requires the addition of a suitable fungistat or fungicide.

The infestation of mold and other fungi in the surfaces and structures of commercial buildings and residences creates more than a basic concern for property damage and such attendant costs. Rather, the conditions that lead to severe mold/fungal infestations in places where people work and live, e.g., moist, poorly ventilated closed areas, also may increase the susceptibility of fungal infection and other illnesses in the occupants and thus present a significant and currently well-publicized health problem. Thus, development of practical and effective means of combatting such mold and other fungal infestations in residences and places of work and recreation, wherein such antifungal agents are effective yet present little or no risk to individuals, is a salient and relevant problem. Such innovative developments for antifungals are particularly important as conventional fungicides in current use may prove ineffective in eradicating the problem of infestation and/or may present aversive or impractical consequences for use in closed areas with high occupancies and/or high volumes of foot traffic (and thus present risks to large numbers of individuals), or in such areas where people reside (and thus present factors or long exposure times of individuals to fungicidal agents and impracticalities in the provision of alternative housing arrangements).

2.2 Current Therapies

Four main classes of anti-fungal agents are in the market so far and their mechanism of action is summarized below.

Polyene Antifungal Drugs

Amphotericin, nystatin, and pimaricin interact with sterols in the cell membrane (ergosterol in fungi, cholesterol in humans) to form channels through which small molecules leak from the inside of the fungal cell to the outside.

Azole Antifungal Drugs

Fluconazole, itraconazole, and ketoconazole inhibit cytochrome P450-dependent enzymes (particularly C14-demethylase) involved in the biosynthesis of ergosterol, which is required for fungal cell membrane structure and function.

Allylamine and Morpholine Antifungal Drugs

Allylamines (naftifine, terbinafine) inhibit ergosterol biosynthesis at the level of squalene epoxidase. The morpholine drug, amorolfine, inhibits the same pathway at a later step.

Antimetabolite Antifungal Drugs

5-Fluorocytosine acts as an inhibitor of both DNA and RNA synthesis via the conversion of 5-fluorocytosine to 5-fluorouracil.

The development of antifungal drug therapies has not evolved as rapidly as the development of antibacterial drug therapies in large part because the human or animal host and the fungal pathogen are both eukaryotes and have many drug targets in common. To date, most of the antifungal drugs and lead compounds have been active against components of the fungal cell surface or membrane (New Antifungal Agents, J. R. Graybill, Eur. J. Clin. Microbiol. Dis. 8:402-412, 1989;

Targets for Antifungal Drug Discovery, Y. Koltin, Annual Reports in Medicinal Chemistry 25:141-148, 1989; Screening of Natural Products for Antimicrobial Agents, L. Silver & K. Bostian, Eur. J. Clin. Microbiol. Dis. 9:455-461, 1990; *New Approaches for Antifungal Drugs*, P. B. Fernandes, ed, Birkhauser: Boston, 1992; *Scrip's Antifungal Report*, by PJB Publications Ltd, 1992). For example, polyene macrolides bind to fungal-specific ergosterol on the cell surface and azole drugs inhibit an ergosterol biosynthetic enzyme. While there has been some effort directed at intracellular targets, such as tubulin and nucleotide metabolism, the resulting compounds, such as benomyl and fluorocytosine, have problems with toxicity and resistance. Cycloheximide (Actidione) is used as a fungicide on some crops even though it is not particularly specific for fungi. Blasticidin S is also used as an antifungal agent on crops.

Not only are fungal-specific therapeutics difficult to identify, but many of the drugs currently available for treatment of mycoses have significant side effects or lack effectiveness against some important pathogens. For example, amphotericin B, an antifungal polyene macrolide antibiotic, has both short-term and long-term adverse effects, ranging from nausea and vomiting to kidney damage. Azole drugs such as clotrimazole and miconazole have such adverse side effects that their use is generally limited to the treatment of topical or superficial infections. The more recently developed triazole drugs, such as fluconazole, have fewer side effects but are not completely effective against all pathogens. Also, some evidence exists for the development of resistance to these drugs. There is therefore an ongoing need for novel antifungal drugs with few, if any, side effects and with effectiveness against pathogens for which current drugs are inadequate.

Furthermore, fungal and mycotic pathogens often are either naturally resistant, or develop resistance, to many therapeutics by virtue of cellular permeability barriers to drug entry. Development of fungicide resistance occurs when a fungal cell or a fungal population that originally was sensitive to a fungicide becomes less sensitive by heritable changes after a period of exposure to the fungicide. Most instances of resistance are related to a change at the site of action or a change in the uptake of the fungicide, with detoxification being a rare event (J. Dekker, Preventing and Managing Fungicide Resistance, Pesticide Resistance: Strategies and Tactics in Man). In certain applications (e.g., agriculture) it is possible to combat resistance through alternation of fungicides or the use of fungicide mixtures. To prevent or delay the buildup of a resistant pathogen population, different chemicals that are effective against a particular disease must be available. One way of increasing the number of available chemicals is to search for new site-specific inhibitors (id.). Thus, the challenge is to develop methods for identifying compounds which can penetrate the pathogen and specifically kill it or arrest its growth without also adversely affecting the human, animal, or plant host.

Classical approaches for identifying antifungal compounds have relied almost exclusively on inhibition of fungal growth as an endpoint. Libraries of natural products, semisynthetic, or synthetic chemicals are screened for their ability to kill or arrest growth of the target pathogen or a related nonpathogenic model organism. These tests are cumbersome and provide no information about a compound's mechanism of action. The promising lead compounds that emerge from such screens must then be tested for possible toxicity to the human, animal, or plant host, and detailed mechanism-of-action studies must subsequently be conducted to identify the affected molecular target and precisely how the drug interacts with this target.

Because treatment of mycoses are assuming even greater public importance, especially in light of the growing number of immunocompromised or immunosuppressed individuals and pronounced public apprehension of mycotic infestation in residences and places of work, pressure has mounted to develop more effective methods for antifungal and antimycotic drug discovery.

Commercial succes of antifungal agents is heavily dependent on efficacy relative to existing therapies for the target indication. Thus, the heightened specificity and expected lower cytotoxicity of inhibitors of a fungal tRNA splicing endonuclease identified and developed through the methods of the present invention will lead to a drug with a compeititive advantage to those currently on the market.

2.3 tRNA Production

Maturation and maintenance of tRNA within eucaryal cells requires several processing events including 5' and 3' endtrimming, modification of specific bases, and in some cases, intron removal. The enzymes for these various steps in processing have been characterized in the yeast, archaeal, mammalian and bacterial systems (Deutscher, M. P. tRNA Processing Nucleases, in tRNA: Structure, Biosynthesis and Function, D. Soll and U. RajBhandary (eds.), American Society for Microbiology, Washington D.C., (1995), pp. 51-65). 5' end trimming requires the activity of Rnase P and 3' end trimming requires the function of various endo- and exo-nucleases. Modification occurs through interaction of tRNA with various modification enzymes. Most tRNAs contain a number of global as well as species-specific modifications (Bjork, G. Biosynthesis and Function of Modified Nucleosides, in tRNA: Structure, Biosynthesis and Function, D. Soll and U. RajBhandary (eds.), American Society for Microbiology, Washington D.C., (1995), pp. 165-205). In archaea and eucarya, several isoaccepting groups of tRNA contain intervening sequences ranging in size from 14-105 nucleotides (Trotta, C. R. and Abelson, J. N. tRNA Splicing: An RNA World Add-On or an Ancient Reaction? In RNA World II, Tom Cech, Ray Gesteland and John Atkins (eds.), Cold Spring Harbor Laboratory Press (1999) and Abelson et al., 1998, Journal of Biological Chemistry 273:12685-12688). Removal of the intron requires the activity of 3 enzymes. In the first step, the tRNA is recognized and cleaved at the 5' and 3' junction by the tRNA splicing endonuclease. The archaeal and eucaryal tRNA endonuclease are evolutionary conserved enzymes and contain a similar active site to achieve cleavage at the 5' and 3' splice sites. However, they have diverged to recognize the tRNA substrate in a different manner. The archaeal enzyme recognizes a conserved intronic structure known as the bulge-helix-bulge. This structure is comprised of two 3-nucleotide bulges separated by a 4-nucleotide helix. Cleavage occurs within each bulge to release the intron. The eucaryal endonuclease recognizes the tRNA substrate in a mature domain dependent fashion, measuring a set distance from the mature domain to the 5' and 3' splice sites (Reyes et al., 1988, Cell 55:719-730). It has recently been demonstrated, however, that the eucaryal enzyme requires a bulge at each splice site and that the enzyme has actually retained the ability to recognize tRNA by an intron-dependent recognition mechanism identical to that of the archaeal endonuclease (Fruscoloni et al., 2001, EMBO Rep 2:217-221). Once cleaved, the tRNA half molecules are ligated by the action of a unique tRNA splicing ligase (Trotta, C. R. and Abelson, J. N. tRNA Splicing: An RNA World Add-On or an Ancient Reaction? In RNA World II, Tom Cech, Ray Gesteland and John Atkins (eds.), Cold Spring Harbor Laboratory Press (1999) and Abelson et al., 1998, Journal of Biological Chemistry 273:12685-12688). In fungi, the product of ligation is a tRNA with a phosphate at the splice junction. Removal of the phosphate is carried out by a tRNA 2'-phosphotransferase to yield a mature tRNA product (Trotta, C. R. and Abelson, J. N. tRNA Splicing: An RNA World Add-On or an Ancient Reaction? In RNA World II, Tom Cech, Ray Gesteland and John Atkins (eds.), Cold Spring Harbor Laboratory Press (1999) and Abelson et al., 1998, Journal of Biological Chemistry 273:12685-12688). The ubiquity of tRNA in the eukaryotic cell and the capacity for innovative contemporary efforts to isolate and exploit key differences in tRNA functionality between fungi and animalia kingdoms offers a distinct potential for new compounds that selectively and effectively target the tRNA machinery of infectious fungi while minimizing deleterious effects upon an infected human or animal host. Citation of any reference herein is not to be construed as an admission of its availability as prior art.

3. SUMMARY OF THE INVENTION

The present invention provides methods for identifying a compound that modulates the activity of a fungal tRNA splicing endonuclease. In particular, the invention provides methods for identifying a compound that inhibits the activity of a fungal tRNA splicing endonuclease. The invention encompasses the use of the compounds identified for the prevention, treatment, management or amelioration of a fungal infection or a symptom thereof. The invention also encompasses the use of the compounds identified to impede fungal infestation.

The invention provides cell-based and cell-free assays for the identification of a compound that modulates the activity of a fungal tRNA splicing endonuclease. These assays may be reporter gene-based assays, fluorescence resonance energy transfer ("FRET")-based assays, or fluorescence polarization assays and may be conducted in a high-throughput screen format. Further, these assays directly or indirectly measure the ability of a compound to modulate a fungal tRNA splicing endonuclease. In a preferred embodiment, the ability of a compound to modulate fungal tRNA splicing endonuclease activity that is identified utilizing an indirect assay (e.g., a cell-based assay such as a reporter gene cell-based assay or a FRET cell-based assay) is confirmed utilizing a more direct assay (e.g., a FISH assay).

The reporter gene-based assays may be conducted by contacting a compound with a fungal cell genetically engineered to express a nucleic acid comprising a reporter gene, wherein the reporter gene comprises a tRNA intron, and measuring the expression of said reporter gene. Alternatively, the reporter gene-based assays may be conducted by contacting a compound with a fungal cell-free extract and a nucleic acid comprising a reporter gene, wherein the reporter gene comprises a tRNA intron, and measuring the expression of said reporter gene. The alteration in reporter gene expression relative to a previously determined reference range, or to the expression in the absence of the compound or the expression in the presence of an appropriate control (e.g., a negative control) in such reporter-gene based assays indicates that a particular compound modulates the activity of the tRNA splicing endonuclease. In particular, a decrease in reporter gene expression relative to a previously determined reference range, or relative to the reporter gene expression in the absence of the compound or presence of an appropriate control (e.g., a negative control) under proper control conditions in such reporter-gene based assays indicates that a particular compound reduces or inhibits the activity of a fungal tRNA splicing endonuclease (e.g., the recognition or cleavage of a tRNA intron). In contrast, an increase in reporter gene expression relative to a previously determined reference range, or to the expression in the absence of the compound or the presence of an appropriate control (e.g., a negative control) in such reporter-gene based assays indicates that a particular compound enhances the activity of a fungal tRNA splicing endonuclease.

In one embodiment, the invention provides a method for identifying a compound that modulates fungal tRNA splicing endonuclease activity, said method comprising: (a) expressing a nucleic acid comprising a reporter gene in a fungal cell, wherein the reporter gene comprises a tRNA intron; (b) contacting said cell with a member of a library of compounds; and (c) detecting the expression of said reporter gene, wherein a compound that modulates the tRNA splicing endonuclease activity is identified if the expression of said reporter gene in the presence of a compound is altered relative to that of a previously determined reference range, or the expression of said reporter gene in the absence of the compound or the presence of a negative control (e.g., PBS).

In another embodiment, the invention provides a method for identifying a compound that modulates fungal tRNA splicing endonuclease activity, said method comprising: (a) contacting a member of a library of compounds with a fungal cell containing a nucleic acid comprising a reporter gene, wherein the reporter gene comprises a tRNA intron; and (b) detecting the expression of said reporter gene, wherein a compound that modulates the tRNA splicing endonuclease activity is identified if the expression of said reporter gene in the presence of a compound is altered relative to a previously determined reference range, or the expression of said reporter gene in the absence of the compound or in the presence of a negative control (e.g., PBS).

In another embodiment, the invention provides a method for identifying a compound that modulates fungal tRNA splicing endonuclease activity, said method comprising: (a) contacting a member of a library of compounds with a fungal cell-free extract and a nucleic acid comprising a reporter gene, wherein the reporter gene comprises a tRNA intron; and (b) detecting the expression of said reporter gene, wherein a compound that modulates tRNA splicing endonuclease activity is identified if the expression of said reporter gene in the presence of such compound is altered relative to a previously determined reference range, or the expression of said reporter gene in the absence of the compound or in the presence of a negative control (e.g., PBS).

In accordance with the invention, the step of contacting a compound with a fungal cell or a fungal cell-free extract and a nucleic acid in the reporter gene-based assays described herein is preferably conducted in an aqueous solution comprising a buffer and a combination of salts (such as KCl, NaCl and/or $MgCl_2$). The optimal concentration of each salt used in the aqueous solution is dependent on the endonuclease and the compounds used, and can be determined using routine experimentation. In a specific embodiment, the aqueous solution approximates or mimics physiologic conditions. In another specific embodiment, the aqueous solution further comprises a detergent or a surfactant.

The reporter gene constructs utilized in the reporter gene-based assays described herein may comprise the coding region of a reporter gene and a tRNA intron that renders the mRNA coding the reporter gene out of frame. Alternatively, the reporter gene constructs utilized in the reporter gene-based assays described herein may comprise a tRNA intron within the 5' untranslated region, 3' untranslated region or both the 5' and 3' untranslated regions. In another alternative, the tRNA intron interrupts an mRNA splicing element. In a specific embodiment, a reporter gene construct utilized in the reporter gene-based assays described herein comprises the coding region of a reporter gene and a tRNA intron within the open reading frame of the reporter gene. The intron utilized in the reporter gene constructs described herein preferably comprises a bulge-helix-bulge conformation.

Any reporter gene well-known to one of skill in the art may be utilized in the reporter gene constructs described herein. Examples of reporter genes include, but are not limited to, the gene encoding firefly luciferase, the gene coding renilla luciferase, the gene encoding click beetle luciferase, the gene encoding green fluorescent protein, the gene encoding yellow fluorescent protein, the gene encoding red fluorescent protein, the gene encoding cyan fluorescent protein, the gene encoding blue fluorescent protein, the gene encoding beta-galactosidase, the gene encoding beta-glucoronidase, the gene encoding beta-lactamase, the gene encoding chloramphenicol acetyltransferase, and the gene encoding alkaline phosphatase.

The reporter gene-based assays described herein may potentially be conducted in a fungal cell genetically engineered to express a reporter gene or in vitro utilizing a fungal cell-free extract. A cell or cell line of any fungal species well-known to one of skill in the art may be utilized in accordance with the methods of the invention. Further, a fungal cell-free extract may be derived from any cell or cell line of any species well-known to one of skill in the art; fungal species of interest include, but are not limited to, such species as Absidia spp., Actinomadura madurae, Actinomyces spp., Allescheria boydii, Alternaria spp., Anthopsis deltoidea, Apophysomyces elegans, Arnium leoporinum, Aspergillus spp., Aureobasidium pullulans, Basidiobolus ranarum, Bipolaris spp., Blastomyces dermatitidis, Candida spp., Cephalosporium spp., Chaetoconidium spp., Chaetomium spp., Cladosporium spp., Coccidioides immitis, Conidiobolus spp., Corynebacterium tenuis, Cryptococcus spp., Cunninghamella bertholletiae, Curvularia spp., Dactylaria spp., Epidermophyton spp., Epidermophyton floccosum, Exserophilum spp., Exophiala spp., Fonsecaea spp., Pusarium spp., Geotrichum spp., Helminthosporium spp., Histoplasma spp., Lecythophora spp., Madurella spp., Malassezia furfur, Microsporum spp., Mucor spp., Mycocentrospora acerina, Nocardia spp., Paracoccidioides brasiliensis, Penicillium spp., Phaeosclera dematioides, Phaeoannellomyces spp., Phialemonium obovatum, Phialophora spp., Phoma spp., Piedraia hortai, Pneumocystis carinii, Pythium insidiosum, Rhinocladiella aquaspersa, Rhizomucor pusillus, Rhizopus spp., Saksenaea vasiformis, Sarcinomyces phaeomuriformis, Sporothrix schenckii, Syncephalastrum racemosum, Taeniolella boppii, Torulopsosis spp., Trichophyton spp., Trichosporon spp., Ulocladium chartarum, Wangiella dermatitidis, and Xylohypha spp.

Fluorescent resonance energy transfer ("FRET") assays may be used to identify a compound that modulates the activity of a fungal tRNA splicing endonuclease. The FRET assays may be conducted utilizing labeled subunits of a fungal tRNA splicing endonuclease or labeled substrates for a fungal tRNA splicing endonuclease. The FRET cell-based assays may be conducted by microinjecting or transfecting a substrate for a fungal tRNA splicing endonuclease into a fungal cell and contacting the cell with a compound, wherein the substrate is labeled at the 5' end with a fluorophore and labeled at the 3' end with a quencher, or, alternatively, the substrate is labeled at the 5' end with a quencher and labeled at the 3' end with a fluorophore, and measuring the fluorescence of the substrate by, e.g., fluorescence microscopy or a fluorescence emission detector such as a Viewlux or Analyst. The endogenous tRNA splicing endonuclease will cleave the substrate and result in the production of a detectable fluorescent signal. A compound that inhibits or reduces the activity of the endogenous tRNA splicing endonuclease will inhibit or reduce the cleavage of the substrate and thus, inhibit or reduce the production of a detectable fluorescent signal. A compound that enhances the activity of the endogenous tRNA splicing endonuclease will enhance the cleavage of the substrate and thus, increase the production of a detectable fluorescent signal. Alternatively, the FRET cell-based assays may be conducted by microinjecting or transfecting a substrate for a fungal tRNA splicing endonuclease into a fungal cell and contacting the cell with a compound, wherein the substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety, and measuring the fluorescence of the substrate by, e.g., fluorescence microscopy or a fluorescence emission detector such as a Viewlux or Analyst. The endogenous tRNA splicing endonuclease will cleave the substrate and result in a decrease in the fluorescence emission of the fluorescent acceptor moiety at the wavelength of the fluorescent donor moiety. A compound that inhibits or reduces the activity of the endogenous tRNA splicing endonuclease will inhibit or reduce cleavage of the substrate and thus, increase the fluorescence emission of the fluorescent acceptor moiety at the wavelength of the fluorescent donor moiety. A compound that enhances the activity of the endogenous tRNA splicing endonuclease will enhance the cleavage of the substrate and thus maintain or further reduce the fluorescence emission of the fluorescent acceptor moiety at the wavelength of the fluorescent donor moiety.

Optionally, an agent known to inhibit or reduce the activity of a fungal tRNA splicing ligase, such as an antibody that specifically binds to the ligase, is included in the contacting step of the FRET assays to exclude the possibility that the compound is solely inhibiting or reducing the activity of the ligase. In some embodiments, the activity of a tRNA splicing ligase is inhibited or reduced by excluding ATP from the reaction mixture. Although not intending to be bound by a particular mechanism of action, since the activity of tRNA splicing ligase is dependent on the presence of ATP, excluding ATP from the reaction effectively reduces the activity of the tRNA splicing ligase. Alternatively, a fungal cell deficient in tRNA splicing ligase activity is utilized in the FRET assays.

In one embodiment, the invention provides a method of identifying an antifungal compound that inhibits or reduces fungal tRNA splicing endonuclease activity, said method comprising: (a) microinjecting or transfecting a substrate of a tRNA splicing endonuclease into a fungal cell, wherein the substrate is labeled at the 5' end with a fluorophore and at the 3' end with a quencher, or, alternatively, the substrate is labeled at the 5' end with a quencher and labeled at the 3' end with a fluorophore; (b) contacting the cell with a member of a library of compounds; and (c) measuring the activity of the tRNA splicing endonuclease, wherein an antifungal compound that inhibits tRNA splicing activity is identified if a fluorescent signal is less detectable in the presence of the compound relative to the signal in the absence of the compound or the presence of an appropriate control (e.g., a negative control, such as PBS). In another embodiment, the invention provides a method of identifying an antifungal compound that inhibits fungal tRNA splicing endonuclease activity, said method comprising: (a) contacting a fungal cell containing a substrate of a tRNA splicing endonuclease with a member of a library of compounds, wherein the substrate is labeled at the 5' end with a fluorophore and at the 3' end with a quencher, or, alternatively, the substrate is labeled at the 5' end with a quencher and labeled at the 3' end with a fluorophore; and (b) measuring the activity of the tRNA splicing endonuclease, wherein an antifungal compound that inhibits or reduces tRNA splicing activity is identified if a fluorescent signal is less detectable in the presence of the compound relative to the signal in the absence of the compound or the presence of an appropriate control (e.g., a negative control, such as PBS).

In another embodiment, the invention provides a method of identifying an antifungal compound that inhibits or reduces fungal tRNA splicing endonuclease activity, said method comprising: (a) microinjecting or transfecting a substrate of a tRNA splicing endonuclease into a fungal cell, wherein said substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety; (b) contacting the cell with a member of a library of compounds; and (c) measuring the activity of the tRNA splicing endonuclease, wherein an antifungal compound that inhibits or reduces tRNA splicing endonuclease activity is identified if the fluorescence emission of the fluorescent acceptor moiety at the wavelength of the fluorescent donor moiety in the presence of the compound is increased relative to the fluorescence emission in the absence of the compound or the presence of an appropriate control (e.g., a negative control, such as PBS). In another embodiment, the invention provides a method of identifying an antifungal compound that inhibits or reduces fungal tRNA splicing endonuclease activity, said method comprising: (a) contacting a fungal cell containing substrate of a tRNA splicing endonuclease with a member of a library of compounds, wherein said substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with fluorescent donor moiety; and (b) measuring the activity of the tRNA splicing endonuclease, wherein an antifungal compound that inhibits or reduces tRNA splicing endonuclease activity is identified if the fluorescence emission of the fluorescent acceptor moiety at the wavelength of the fluorescent donor moiety in the presence of the compound is increased relative to the fluorescence emission in the absence of the compound or the presence of an appropriate control (e.g., a negative control, such as PBS).

The FRET cell-free assays may be conducted by contacting a substrate for a fungal tRNA splicing endonuclease with a fungal cell-free extract (preferably, a fungal tRNA splicing endonuclease extract) or a purified fungal tRNA splicing endonuclease and a compound under conditions conducive to the cleavage of the substrate, wherein the substrate is labeled at the 5' end with a fluorophore and labeled at the 3' end with a quencher, or, alternatively, the substrate is labeled at the 5' end with a quencher and labeled at the 3' end with a fluorophore, and measuring the fluorescence of the substrate by, e.g., a fluorescence emission detector such as a Viewlux or Analyst. The tRNA splicing endonuclease in the fungal cell-free extract or the purified fungal tRNA splicing endonuclease will cleave the substrate and result in the production of a detectable fluorescent signal. A compound that inhibits or reduces the activity of the fungal tRNA splicing endonuclease will inhibit or reduce the cleavage of the substrate and thus, inhibit or reduce the production of a detectable fluorescent signal. A compound that enhances the activity of the fungal tRNA splicing endonuclease will enhance the cleavage of the substrate and thus, maintain or increase the production of a detectable fluorescent signal.

Alternatively, the FRET cell-free assays may be conducted by contacting a substrate for a fungal tRNA splicing endonuclease with a fungal cell-free extract or a purified fungal tRNA splicing endonuclease and a compound under conditions conducive to the cleavage of the substrate by the endonuclease, wherein the substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety, and measuring the fluorescence of the substrate by, e.g., a fluorescence emission detector such as a Viewlux or Analyst. The tRNA splicing endonuclease in the fungal cell-free extract or the purified fungal tRNA splicing endonuclease will cleave the substrate and reduce the fluorescence emission of the fluorescent acceptor moiety at the wavelength of the fluorescent donor moiety. A compound that inhibits or reduces the activity of the tRNA splicing endonuclease will inhibit or reduce cleavage of the substrate and thus, increase the fluorescence emission of the fluorescent acceptor moiety at the wavelength of the fluorescent donor moiety. A compound that enhances the activity of the endogenous tRNA splicing endonuclease will enhance the cleavage of the substrate and thus, maintain or reduce the fluorescence emission of the fluorescent acceptor moiety at the wavelength of the fluorescent donor moiety.

Optionally, an agent known to inhibit or reduce the activity of a fungal tRNA splicing ligase, such as an antibody that specifically binds to the ligase, is included in the contacting step of the FRET assays to exclude the possibility that the compound is functioning by solely inhibiting or reducing the activity of the ligase. In some embodiments, the activity of a tRNA ligase is inhibited or reduced by excluding ATP from the reaction mixture. Although not intending to be bound by a particular mechanism of action, since the activity of tRNA splicing ligase is dependent on the presence of ATP, excluding ATP from the reaction effectively reduces the activity of the tRNA splicing ligase. Alternatively, a cell-free extract from a fungal cell deficient in tRNA splicing ligase is utilized in the FRET assays.

In one embodiment, the invention provides a method of identifying an antifungal compound that inhibits or reduces fungal tRNA splicing endonuclease activity, said method comprising: (a) contacting a fungal cell-free extract (preferably, a fungal tRNA splicing endonuclease extract) or a purified fungal tRNA splicing endonuclease with a substrate of a tRNA splicing endonuclease and a member of a library of compounds under conditions conducive to the cleavage of the substrate by the endonuclease, wherein the substrate is labeled at the 5' end with a fluorophore and at the 3' end with a quencher, or, alternatively, the substrate is labeled at the 5' end with a quencher and labeled at the 3' end with a fluorophore; and (b) measuring the activity of the tRNA splicing endonuclease, wherein an antifungal compound that inhibits or reduces tRNA splicing endonuclease activity is identified if a fluorescent signal is less detectable in the presence of the compound relative to the signal in the absence of the compound or the presence of an appropriate control (e.g., a negative control, such as PBS). In another embodiment, the invention provides a method of identifying an antifungal compound that inhibits or reduces fungal tRNA splicing endonuclease activity, said method comprising: (a) contacting a fungal cell-free extract (preferably, a fungal tRNA splicing endonuclease extract) or a purified fungal tRNA splicing endonuclease with a substrate of a tRNA splicing endonuclease and a member of a library of compounds under conditions conducive for the cleavage of the substrate, wherein said substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety; and (b) measuring the activity of the tRNA splicing endonuclease, wherein an antifungal compound that inhibits or reduces tRNA splicing endonuclease activity is identified if the fluorescent emission of the fluorescent acceptor moiety at the wavelength of the fluorescent donor moiety in the presence of the compound is increased relative to the fluorescence emission in the absence of the compound or the presence of an appropriate control (e.g., a negative control, such as PBS).

The substrates for a fungal tRNA splicing endonuclease utilized in the FRET assays described herein comprise an intron. The intron may have a bulge-helix-bulge conformation or a mature domain that contains an intron. Any fungal species may be utilized in the FRET assays described herein. In a specific embodiment, the fungal species utilized in the FRET assays described herein are deficient in tRNA splicing ligase activity.

The substrates for a fungal tRNA splicing endonuclease utilized in the FRET assays described herein have a conformation such that the labeled ends of the substrate are in close spatial proximity prior to cleavage by the endonuclease. In a specific embodiment, the substrate is created by joining two tRNAs together, 5' to 3', to enable the tRNA to be circularized within the highly-structured 60 nucleotide intron. Oligonucleotides are then selected that foster PCR amplification of the entire tRNA from within the intron. Upon transcription, the tRNA 5' and 3' ends are located within the intron. When this tRNA substrate is cleaved by the tRNA splicing endonuclease at the two cleavage sites, the intronic sequences are released from the tRNA. The 5' and 3' ends of this embodiment may be designed so that a 5-10 nucleotide intron or a 50-55 nucleotide intron are released upon cleavage.

The effect of a compound on the activity of a fungal tRNA splicing endonuclease may be determined utilizing a fluorescence polarization-based assay. In such an assay, a fluorescently labeled substrate for a fungal tRNA splicing endonuclease is contacted with a a purified fungal tRNA splicing endonuclease and a compound or member of a library of compounds under conditions conducive to the cleavage of the substrate by the endonuclease; and the fluorescent polarized light emitted is measured utilizing techniques well-known to one of skill in the art or described herein, wherein an alteration in the fluorescently polarized light emitted relative to emission in the absence of the compound or presence of a an appropriate control (e.g., a negative control, such as PBS) indicates that the compound or member of a library of compounds modulates fungal tRNA splicing endonuclease activity.

Further, the effect of a compound on the activity of a fungal tRNA splicing endonuclease may be determined utilizing a tRNA endonuclease suppression assay. In such an assay, a host cell is engineered to contain a reporter gene construct and a suppressor, tRNA, wherein the reporter gene construct comprises a reporter gene with a nonsense codon in its open reading frame such that the open reading frame is interrupted, and the expression of the suppressor tRNA is regulated by an inducible regulatory element and the suppressor tRNA contains a tRNA intron in the anticodon stem such that only properly spliced suppressor tRNA is functional. The expression of the suppressor tRNA is induced and the host cell is contacted with a compound, whereupon the expression of the reporter gene and/or the activity of the protein encoded by the reporter gene is measured utilizing techniques well-known to one of skill in the art or described herein. A compound that inhibits or reduces the activity of a fungal tRNA splicing endonuclease will inhibit or reduce the production of functional suppressor tRNA and thus, reduce the expression of the reporter gene relative to a previously determined reference range, in the absence of the compound or the presence of an appropriate control (e.g., a negative control, such as PBS). A compound that enhances the activity of a fungal tRNA splicing endonuclease will enhance the production of functional suppressor tRNA and thus enhance the production of the reporter gene relative to that of a previously determined reference range, or relative to the absence of the compound or the presence of an appropriate control (e.g., a negative control, such as PBS).

The assays of the present invention can be performed using different incubation times. In a cell-free system, the cell-free extract or the purified tRNA splicing endonuclease and substrate for fungal tRNA splicing endonuclease can be incubated together before the addition of a compound or a member of a library of compounds. In certain embodiments, the cell-free extract or the purified fungal tRNA splicing endonuclease are incubated with a substrate for fungal tRNA splicing endonuclease before the addition of a compound or a member of a library of compounds for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day. In other embodiments, the cell-free extract or purified fungal tRNA splicing endonuclease, or a substrate for fungal tRNA splicing endonuclease is incubated with a compound or a member of a library of compounds before the addition of the substrate or the cell-free extract or purified fungal tRNA splicing endonuclease, respectively. In certain embodiments, a compound or a member of a library of compounds is incubated with a substrate for fungal tRNA splicing endonuclease or cell-free extract or purified fungal tRNA splicing endonuclease prior to the addition of the remaining component, i.e., cell-free extract, purified fungal tRNA splicing endonuclease, or substrate for fungal tRNA splicing endonuclease, for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day. Once the reaction vessel comprises the three components, i.e., a compound (or a member of a library of compounds), the cell-free extract (or the purified fungal tRNA splicing endonuclease), and substrate for fungal tRNA splicing endonuclease, the reaction may be further incubated for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day.

The progress of the reaction can be measured continuously. For example, if a substrate for a fungal tRNA splicing endonuclease or subunits of a fungal tRNA splicing endonuclease are labeled with fluorophore(s), the progress of the reaction can be monitored continuously using a fluorescence emission detector such as a Viewlux or Analyst. Alternatively, time-points may be taken at different times of the reaction to monitor the progress of the reaction.

Certain assays of the present invention, such as the tRNA endonuclease suppression assay and the cell-based assays, are indirect assays for compounds that affect fungal tRNA splicing endonuclease and may detect compounds that affect another aspect of the tRNA splicing pathway. In order to confirm or ensure that a compound is a modulator of a fungal tRNA splicing endonuclease, any additional assay that measures the direct effect of the compound on fungal tRNA splicing endonuclease activity can be performed. Such assays include assays using a purified fungal tRNA splicing endonuclease and are described below.

The compounds utilized in the assays described herein may be members of a library of compounds. In a specific embodiment, the compound is selected from a combinatorial library of compounds comprising peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small organic molecule libraries. In a preferred embodiment, the small organic molecule libraries are libraries of benzodiazepines, isoprenoids, thiazolidinones, metathiazanones, pyrrolidines, morpholino compounds, or diazepindiones.

In certain embodiments, the compounds are screened in pools. Once a positive pool has been identified, the individual compounds of that pool are tested separately. In certain embodiments, the pool size is at least 2, at least 5, at least 10, at least 25, at least 50, at least 75, at least 100, at least 150, at least 200, at least 250, or at least 500 compounds.

Once a compound that modulates the activity of a fungal tRNA splicing endonuclease is identified, the structure of the compound may be determined utilizing well-known techniques or by referring to a predetermined code. For example, the structure of the compound may be determined by mass spectroscopy, NMR, vibrational spectroscopy, or X-ray crystallography.

A compound identified in accordance with the methods of the invention may directly bind to the fungal tRNA splicing endonuclease. Alternatively, a compound identified in accordance with the methods of invention may bind to the intron. A compound identified in accordance with the methods of invention may also disrupt an interaction between a tRNA intron and a fungal tRNA splicing endonuclease. Further, a compound identified in accordance with the methods of the invention may disrupt the interaction between the tRNA mature domain and the fungal tRNA splicing endonuclease. Additionally, a compound identified in accordance with the methods of the invention may disrupt the interaction between subunits of the fungal tRNA splicing endonuclease. In a particular embodiment, a compound may be identified that specifically targets the loop 10 segment of each of the fungal 54 kd and 15 kd subunits of the fungal tRNA splicing endonuclease, disrupting the interaction between these particular subunits and thereby inhibiting tRNA splicing endonuclease activity.

In a preferred embodiment, a compound identified in accordance with the methods of the invention inhibits fungal tRNA splicing endonuclease activity. In another preferred embodiment, a compound identified in accordance with the methods of the invention exclusively inhibits fungal tRNA splicing endonuclease activity. To determine, ensure or confirm that a compound identified in accordance with the methods of the invention does not affect the activity of an animalia splicing endonuclease, assays similar to those conducted to identify the compound can be performed. Such methods are described, infra, in Section 5 of the present specification.

In certain embodiments of the invention, the compound identified using the assays described herein is a small molecule. In a preferred embodiment, the compound identified using the assays described herein is not known to affect the activity of non-fungal tRNA splicing endonuclease. In another preferred embodiment, the compound identified using the assays described herein has not been used as or suggested to be an antifungal agent.

A compound that modulates the activity of a tRNA splicing endonuclease described herein may be tested in in vitro assays or in vivo assays (e.g., cell-based assays or cell-free assays) well-known to one of skill in the art, or described herein, for the effect of the compound on mRNA translation. The compounds identified by the methods of the present invention can be screened as a control for their effect on the production of mature tRNA from any of the 28 intron containing human pre-tRNAs. In vitro and in vivo assays well-known to one of skill in the art or described herein may be used to determine the effect of a particular compound on fungal cells versus animalia cells (preferably, mammalian cells and, most preferably, human cells). Further, a particular compound identified utilizing the assays described herein may be tested in an animal model to determine the efficacy of the compound in the prevention, treatment, management or amelioration of fungal infection or a symptom thereof.

The invention provides for methods for preventing, treating, managing or ameliorating a fungal infection or a symptom thereof, said method comprising administering to a subject in need thereof a therapeutically or prophylactically effective amount of a compound, or a pharmaceutically acceptable salt thereof, identified according to the methods described herein. In a specific embodiment, the invention provides for a method of preventing, treating, managing or ameliorating a fungal infection or a symptom thereof, said method comprising administering to a subject in need thereof an effective amount of a compound, or a pharmaceutically acceptable salt thereof, identified according to the methods described herein. The invention also provides methods of disinfecting objects or rooms, said methods comprising applying or spraying a compound of the invention or a pharaceutically accpetable salt thereof, identified according to the methods descdribed herein, in an amount sufficient to inhibit or reduce the replication and/or viability of a fungus.

In a specific embodiment, the invention provides a method of identifying a prophylactic or therapeutic agent for the prevention, treatment or amelioration of a fungal infection or a symptom thereof, said method comprising: (a) contacting a member of a library of compounds with a fungal cell containing a nucleic acid comprising a reporter gene, wherein the reporter gene comprises a tRNA intron; and (b) detecting the expression of said reporter gene, wherein if a compound that reduces the expression of said reporter gene relative to a previously determined reference range or the expression of said reporter gene in the absence of said compound or the presence of an appropriate control (e.g., a negative control, such as PBS) is detected in (b), then (c) contacting the compound with a fungal cell and detecting the replication and/or viability of the fungal cell, so that if the compound reduces or inhibits the replication and/or viability of the fungal cell, the compound is identified as an antifungal compound. In accordance with this embodiment, the compound may be administered to an animal model and the efficacy of the compound evaluated by assessing the prevention, management and/or treatment of the fungal infection in the animal model.

In another specific embodiment that provides an additional method of identifying a prophylactic or therapeutic agent for the prevention, treatment or amelioration of a fungal infection or a symptom thereof, this method comprises: (a) microinjecting or transfecting a substrate of a tRNA splicing endonuclease into a fungal cell, wherein said substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety; (b) contacting a member of a library of compounds with the fungal cell; (c) measuring the activity of the tRNA splicing endonuclease, wherein if a compound that alters the fluorscence emission of the fluorescent acceptor moiety at the wavelength of the fluorsecent donor moiety in the presence of the compound relative to the fluorescence emission in the absence of the compound or the presence of an appropriate control (e.g., a negative control, such as PBS); then (d) contacting the compound with a fungal cell and detecting the replication and/or viability of the fungal cell, so that if the compound reduces or inhibits the replication and/or viability of the fungal cell, the compound is identified as an antifungal compound. The compound may be administered to an animal model and the efficacy of the compound evaluated by assessing the prevention, management and/or treatment of the fungal infection in the animal model, in accordance with the methods of the invention.

In an additional specific embodiment further providing a method of identifying a prophylactic or therapeutic agent for the prevention, treatment or amelioration of a fungal infection or a symptom thereof, this method utilizing a fluorescence polarization techniques and featuring steps comprising: (a) microinjecting or transfecting a substrate of a tRNA splicing endonuclease into a fungal cell, wherein the substrate is labeled on its 5' or 3' end such that cleavage by the fungal tRNA endonuclease results in a decrease of size of the labeled portion of the substrate and thus, in a change of fluorescence polarization; (b) a member of a library of coumpounds to be tested is contacted with the cell, wherein if a compound decreases the rotation of the substrate and results in the emitted light remaining polarized when compared to the light emitted by a negative control (for which relatively more light emitted is depolarized, indicating greater activity of the tRNA splicing endonuclease); then (c) contacting the compound with a fungal cell and detecting the replication and/or viability of the fungal cell, so that if the compound reduces or inhibits the replication and/or viability of the fungal cell, the compound is identified as an antifungal compound. As with other similar embodiments that accord with the methods of the invention, the compound may be also be administered to an animal model and the efficacy of the compound evaluated by assessing the prevention, management and/or treatment of the fungal infection in the animal model.

Without being bound by theory, compounds that target the fungal tRNA splicing endonuclease should only be toxic specifically to fungal cells, while allowing for normal cellular growth and metabolism in other eukaryotic cells, particularly human cells, because of differences in tRNA functionality between kingdoms and the fact that not all tRNAs require splicing and tRNA splicing occurs more frequently in proliferating cells. There are only a handful of tRNA species that require removal of intronic sequences (Trotta, C. R. and Abelson, J. N. tRNA Splicing: An RNA World Add-On or an Ancient Reaction? In RNA World II, Tom Cech, Ray Gesteland and John Atkins (eds.), Cold Spring Harbor Laboratory Press (1999)). The current version of the sequence of the human genome has identified 648 tRNA species. Of these, only 28 contain an intron that must be removed by the tRNA splicing endonuclease. The 28 intron containing tRNAs encode 8 different isoaccepting groups. Seven of these isoaccepting groups contain redundant, non-intron-containing versions or can be decoded due to wobble rules of the codon-anticodon interaction (Bjork, G. Biosynthesis and Function of modified Nucleoside in tRNA: Structure, Biosynthesis and Function, D. Soll and V. RayBhandary (eds.), American Society for Microbiology, Washington D.C. (1995). By targeting the fungal tRNA splicing endonuclease, an enzyme dedicated to removal of tRNA introns, the inhibition of tRNA production is fine-tuned to a very few essential tRNA molecules (potentially only a single tRNA). Thus, by inhibiting this process, a very mild toxicity, if any, to human cells will be produced, while the ability of fungal cells to grow, divide and proliferate will be reduced or ablated as a result of the loss of tRNA functionality.

3.1 Terminology

As used herein, the term "compound" refers to any agent or complex that is being tested for its ability to modulate tRNA splicing endonuclease or has been identified as modulating tRNA splicing endonuclease activity.

As used herein, the term "effective amount" refers to the amount (e.g., of therapy, of a compound, identified in accordance with the methods of the invention) which is sufficient to reduce or ameliorate the progression, severity, and/or duration of a fungal infection or one or more symptoms thereof, prevent the recurrence, development or onset of one or more symptoms thereof, or enhance or improve the therapeutic effect(s) of another therapy.

As used herein, the term "fluorescent acceptor moiety" refers to a fluorescent compound that absorbs energy from a fluorescent donor moiety and re-emits the transferred energy as fluorescence. Examples of fluorescent acceptor moieties include, but are not limited to, coumarins and related fluorophores, xanthenes (e.g., fluoresceins, rhodols, and rhodamines), resorufins, cyanines, difluoroboradiazindacenes and phthalocyanines.

As used herein, the term "fluorescent donor moiety" refers to a fluorescent compound that can absorb energy and is capable of transferring the energy to an acceptor, such as another fluorescent compound. Examples of fluorescent donor moieties include, but are not limited to, coumarins and related dyes, xanthene dyes (e.g., fluoresceins, rhodols and rhodamines), resorufins, cyanine dyes, bimanes, acridines, isoindoles, dansyl dyes, aminophthalic hydrazides (e.g., luminol and isoluminol derivatives), aminophthalimides, aminonaphthalimides, aminobenzofurans, aminoquinolines, dicyanohydroquinones, fluorescent europium, terbium complexes and related compounds.

As used herein, the term "fluorophore" refers to a chromophore that fluoresces.

As used herein, the term "host cell" includes a particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "in combination" refers to the use of more than one therapy (e.g., prophylactic and/or therapeutic agents). The use of the term "in combination" does not restrict the order in which therapies (e.g., prophylactic and/or therapeutic agents) are administered to a subject with a fungal infection. A first therapy (e.g., a prophylactic or therapeutic agent, such as a compound identified in accordance with the methods of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent, such as a polyene antifungal, an azole antifungal drug, an allylamine, or 5-fluorocytosine) to a subject with a fungal infection.

As used herein, the term "library" refers to a plurality of compounds. A library can be a combinatorial library, e.g., a collection of compounds synthesized using combinatorial chemistry techniques, or a collection of unique chemicals of low molecular weight (less than 1000 daltons) that each occupy a unique three-dimensional space.

As used herein, the term "ORF" refers to the open reading frame of a mRNA, i.e., the region of the mRNA that is translated into protein.

As used herein, the terms "manage," "managing" and "management" refer to the beneficial effects that a subject derives from a therapy (e.g., a prophylactic or therapeutic agent), which does not result in the eradication of the fungal infection. In certain embodiments, a subject is administered one or more therapies to manage a fungal infection so as to prevent the progression or worsening of the infection.

As used herein, the terms "non-responsive" and refractory" describe patients treated with a currently available therapy (e.g., a prophylactic or therapeutic agent) for a fungal infection, which is not clinically adequate to relieve one or more symptoms associated with such fungal infection. Typically, such patients suffer from severe, persistently active fungal infection and require additional therapy to ameliorate the symptoms associated with the infection.

As used herein, the phrase "pharmaceutically acceptable salt(s)," includes, but is not limited to, salts of acidic or basic groups that may be present in compounds identified using the methods of the present invention. Compounds that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate; gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

As used herein, the terms "prevent", "preventing" and "prevention" refer to the prevention of the development, recurrence or onset of a fungal infection or one or more symptoms thereof, resulting from the administration of one or more compounds identified in accordance the methods of the invention or the administration of a combination of such a compound and an established therapy for a fungal infection.

As used herein, the term "previously determined reference range" refers to a reference range for the readout of a particular assay. In a specific embodiment, the term refers to a reference range for the expression and/or the activity of a reporter gene by a particular cell or in a particular cell-free extract. Each laboratory will establish its own reference range for each particular assays, each cell type and each cell-free extract. In a preferred embodiment, at least one positive control and at least one negative control are included in each batch of compounds analyzed.

As used herein, the terms "prophylactic agent" and "prophylactic agents" refer to any agent(s) which can be used in the prevention of a fungal infection. In certain embodiments, the term "prophylactic agent" refers to a compound identified in the screening assays described herein. In certain other embodiments, the term "prophylactic agent" refers to an agent other than a compound identified in the screening assays described herein which is known to be useful for, or has been or is currently being used to prevent or impede the onset, development, progression and/or severity of a fungal infection or one or more symptoms thereof.

As used herein, the phrase "prophylactically effective amount" refers to the amount of a therapy (e.g., a prophylactic agent which is sufficient to result in the prevention of the development, recurrence or onset of a fungal infection or one or more symptoms thereof.

As used herein, the term "quencher" refers to a molecule or a part of a compound that is capable of reducing the emission from a fluorescent moiety. Such reduction includes reducing the light after the time when a photon is normally emitted from a fluorescent moiety.

As used herein, the term "purified," in the context of a compound, e.g., a compound identified in accordance with the method of the invention, refers to a compound that is substantially free of chemical precursors or other chemicals when chemically synthesized. In a specific embodiment, the compound is 60%, preferably 65%, 70%, 75%, 80%, 85%, 90%, or 99% free of other, different compounds. In a preferred embodiment, a compound identified in accordance with the methods of the invention is purified.

As used herein, the term "purified," in the context of a proteinaceous agent (e.g., a peptide, polypeptide, or protein, such as a tRNA splicing endonuclease or subunit thereof) refers to a proteinaceous agent which is substantially free of cellular material or contaminating proteins from the cell or tissue source from which it is derived, or substantially free of chemical precursors or other chemicals when chemically synthesized. The language "substantially free of cellular material" includes preparations of a proteinaceous agent in which the proteinaceous agent is separated from cellular components of the cells from which it is isolated or recombinantly produced. Thus, a proteinaceous agent that is substantially free of cellular material includes preparations of a proteinaceous agent having less than about 30%, 20%, 10%, or 5% (by dry weight) of heterologous protein, polypeptide, peptide, or antibody (also referred to as a "contaminating protein"). When the proteinaceous agent is recombinantly produced, it is also preferably substantially free of culture medium, i.e., culture medium represents less than about 20%, 10%, or 5% of the volume of the protein preparation. When the proteinaceous agent is produced by chemical synthesis, it is preferably substantially free of chemical precursors or other chemicals, i.e., it is separated from chemical precursors or other chemicals which are involved in the synthesis of the proteinaceous agent. Accordingly, such preparations of a proteinaceous agent have less than about 30%, 20%, 10%, 5% (by dry weight) of chemical precursors or compounds other than the proteinaceous agent of interest. Preferably, proteinaceous agents disclosed herein are isolated.

As used herein, the term "small molecules" and analogous terms include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, organic or inorganic compounds having a molecular weight less than about 100 grams per mole, and salts, esters, and other pharmaceutically acceptable forms of such compounds. Salts, esters, and other pharmaceutically acceptable forms of such compounds are also encompassed.

As used herein, the terms "subject" and "patient" are used interchangeably herein. The terms "subject" and "subjects" refer to an animal, preferably a mammal, including non-primates (e.g., cow, pig, horse, cat, dog, rat or mouse) and primates (e.g., monkey or human), and more preferably a human. In one embodiment, the subject is refractory or non-responsive to current therapies for a fungal infection. In another embodiment, the subject is a farm animal (e.g., horse, cow, pig) or a pet (e.g., dog or cat). In a preferred embodiment, the subject is a human.

As used herein, the phrase "a substrate for a tRNA splicing endonuclease" refers to any nucleotide sequence recognized and excised by a eukaryotic tRNA splicing endonuclease, in particular, a fungal tRNA splicing endonuclease. For example, a nucleotide sequence comprising a bulge-helix-bulge structure or a mature domain of a precursor tRNA may be utilized as a substrate for a fungal tRNA splicing endonuclease in an assay described herein. A nucleotide sequence recognized and excised by a eukaryotic (preferably, fungal) tRNA splicing endonuclease may comprise 10 nucleotides, 15 nucleotides, 20 nucleotides, 25 nucleotides, 25 nucleotides, 30 nucleotides, 40 nucleotides, 45 nucleotides, 50 nucleotides, 55 nucleotides, 60 nucleotides, 65 nucleotides, 75 nucleotides, 100 nucleotides, 125 nucleotides, 150 nucleotides, or more. In a specific embodiment, the substrates for a fungal tRNA splicing endonuclease utilized in the assays described herein comprise a tRNA intron. The substrate may comprise a mature domain or a bulge-helix-bulge conformation. In a specific embodiment, the substrate comprises a mature domain of a precursor tRNA. In another embodiment, wherein the assay being conducted is a FRET assay, the substrate comprises a tRNA intron and 5' and 3' ends of the intron are in close spatial proximity to allow for fluorescence resonance energy transfer.

A substrate for a fungal tRNA endonuclease may be produced by any method well-known to one of skill in the art. For example, the substrate may be chemically synthesized using phosphoramidite or other solution or solid-phase methods. Detailed descriptions of the chemistry used to form polynucleotides by the phosphoramidite method are well known (see, e.g., Caruthers et al., U.S. Pat. Nos. 4,458,066 and 4,415,732; Caruthers et al., 1982, Genetic Engineering 4:1-17; *Users Manual Model* 392 *and* 394 *Polynucleotide Synthesizers,* 1990, pages 6-1 through 6-22, Applied Biosystems, Part No. 901237; Ojwang, et al., 1997, Biochemistry, 36:6033-6045). After synthesis, the substrate can be purified using standard techniques known to those skilled in the art (see Hwang et al., 1999, Proc. Natl. Acad. Sci. USA 96(23): 12997-13002 and references cited therein). Depending on the length of the substrate and the method of its synthesis, such purification techniques include, but are not limited to, reverse-phase high-performance liquid chromatography ("reverse-phase HPLC"), fast performance liquid chromatography ("FPLC"), and gel purification.

In a specific embodiment, the substrate for a eukaryotic (preferably, a fungal) tRNA splicing endonuclease that is used in the in vitro screening assays is depicted in FIG. 1B or 1C. To generate the hybridized tRNA substrate, both strands of the hybridized tRNA substrate are transcribed separately and the two strands are subsequently hybridized by heating and cooling. For the synthesis of the circularly permuted tRNA substrate, the RNA is transcribed from the 5' end in the intron (see FIG. 1C) to the 3' end in the intron.

As used herein, the term "synergistic" refers to a combination of a compound identified using one of the methods described herein, and another therapy (e.g., a prophylactic or therapeutic agent) which has been or is currently being used to prevent, treat, manage or ameliorate a fungal infection or one or more symptoms thereof, which is more effective than the additive effects of the agents. A synergistic effect of a combination of therapies permits the use of lower dosages of one or more of the therapies and/or less frequent administration of the therapies to a subject with a fungal infection. The ability to utilize lower dosages of a therapy and/or to administer the therapy less frequently reduces the toxicity associated with the administration of the therapy to a subject without reducing the efficacy of the therapy in the prevention, treatment, management or amelioration of a fungal infection or one or more symptoms thereof. In addition, a synergistic effect can result in improved efficacy of therapies in the prevention, treatment, management or amelioration of a fungal infection or one or more symptoms thereof. Finally, a synergistic effect of a combination of therapies may avoid or reduce adverse or unwanted side effects associated with the use of either therapy alone.

As used herein, the terms "therapeutic agent" and "therapeutic agents" refer to any agent(s) which can be used in the prevention, treatment, management or amelioration of one or more symptoms of a fungal infection. In certain embodiments, the term "therapeutic agent" refers to a compound identified in the screening assays described herein. In other embodiments, the term "therapeutic agent" refers to an agent other than a compound identified in the screening assays described herein which is known to be useful for, or has been or is currently being used for the prevention, treatment, management or amelioration of a fungal infection or one or more symptoms thereof.

As used herein, the term "therapeutically effective amount" refers to that amount of the therapy (e.g., a therapeutic agent) sufficient to reduce the severity of a fungal infection, reduce the duration or a fungal infection, ameliorate one or more symptoms of a fungal infection, or prevent advancement of a fungal infection, or enhance or improve the therapeutic effect(s) of another therapy. In a specific embodiment, a therapeutically effective amount refers to the amount of a therapy (e.g., therapeutic agent) that inhibits or reduces the replication and/or viability of fungal cells, inhibits or reduces the onset, development or progression of a fungal infection or one or more symptoms thereof, inhibits or reduces the spread of a fungal infection from one tissue or organ to another tissue or organ, or inhibits or reduces the spread of a fungal infection from one subject to another. In another specific embodiment, a therapeutically effective amount of a therapy (e.g., a therapeutic agent) reduces the replication of a fungus by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%, relative to a negative control, such as PBS.

As used herein, the terms "therapy" and "therapies" refer to any protocol(s), method(s) and/or agent(s) that can be used in the prevention, treatment, management or amelioration of a fungal infection or one or more symptoms thereof. In certain embodiments, the terms "therapy" and "therapies" refer to antifungal therapy, supportive therapy and/or other therapies useful in the prevention, treatment, management or amelioration of a fungal infection or one or more symptoms thereof known to skilled medical personnel.

As used herein, the terms "treat," "treatment" and "treating" refer to the reduction or amelioration of the progression, severity and/or duration of a fungal infection or one or more symptoms thereof resulting from the administration of one or more therapies (e.g., one or more compounds identified in accordance the methods of the invention), or a combination of therapies. In specific embodiments, such terms refer to the inhibition or reduction in the replication and/or viability of fungal cells.

As used herein, the term "tRNA intron" refers to any nucleotide sequence recognized and excised by a fungal tRNA splicing endonuclease. In particular, the term "tRNA intron" refers to an intron typically found in a precursor tRNA.

As used herein, the term "tRNA splicing endonuclease" refers to the enzyme that is responsible for the recognition of the splice sites contained in precursor tRNA and the cleavage of the introns present in precursor tRNA. The archaeal tRNA splicing endonuclease recognizes the bulge-helix-bulge motif in archaeal precursor tRNA. The eukaryotic tRNA splicing endonuclease recognizes the splice sites contained in precursor tRNA by measuring the distance from the mature domain to the splice sites. The eukaryotic tRNA splicing endonuclease also has the capacity to recognize a bulge-helix-bulge motif contained in precursor tRNA. The yeast tRNA endonuclease is a heterotetramer comprising subunits having the molecular masses of 54 kDa (SEN54; accession number YPL083c), 44 kDa (SEN2; accession number M32336), 34 kDa (SEN 34; YAR008w), and 15 kDa (SEN 15; accession number YMR059w). The human homologs of the SEN2 and SEN34 subunits have been identified and the amino acid sequences can be found in GenBank under accession numbers NP_079541 and XP_085899, respectively. The tRNA splicing endonuclease utilized in the assays described herein can be from any fungal species, including, but not limited to *Absidia* spp., *Actinomadura madurae*, *Actinomyces* spp., *Allescheria boydii*, *Altemaria* spp., *Anthopsis deltoidea*, *Apophysomyces elegans*, *Arnium leoporinum*, *Aspergillus* spp., *Aureobasidium pullulans*, *Basidiobolus ranarum*, *Bipolaris* spp., *Blastomyces dermatitidis*, *Candida* spp., *Cephalosporium* spp., *Chaetoconidium* spp., *Chaetomium* spp., *Cladosporium* spp., *Coccidioides immitis*, *Conidiobolus* spp., *Corynebacterium tenuis*, *Cryptococcus* spp., *Cunninghamella bertholletiae*, *Curvularia* spp., *Dactylaria* spp., *Epidermophyton* spp., *Epidermophyton floccosum*, *Exserophilum* spp., *Exophiala* spp., *Fonsecaea* spp., *Fusarium* spp., *Geotrichum* spp., *Helminthosporium* spp., *Histoplasma* spp., *Lecythophora* spp., *Madurella* spp., *Malassezia furfur*, *Microsporum* spp., *Mucor* spp., *Mycocentrospora acerina*, *Nocardia* spp., *Paracoccidioides brasiliensis*, *Penicillium* spp., *Phaeosclera dematioides*, *Phaeoannellomyces* spp., *Phialemonium obovatum*, *Phialophora* spp., *Phoma* spp., *Piedraia hortai*, *Pneumocystis carinii*, *Pythium insidiosum*, *Rhinocladiella aquaspersa*, *Rhizomucor pusillus*, *Rhizopus* spp., *Saksenaea vasiformis*, *Sarcinomyces phaeomuriformis*, *Sporothrix schenckii*, *Syncephalastrum racemosum*, *Taeniolella boppii*, *Torulopsosis* spp., *Trichophyton* spp., *Trichosporon* spp., *Ulocladium chartarum*, *Wangiella dermatitidis*, and *Xylohypha* spp. In a specific embodiment, the tRNA splicing endonuclease utilized in the assays described herein is derived from or encodes the yeast tRNA splicing endonuclease.

As used herein, the term "tRNA splicing endonuclease extract" refers to an extract from a cell containing tRNA splicing endonuclease activity. In certain embodiments, a tRNA splicing endonuclease extract is a cell-extract containing tRNA splicing endonuclease activity and the components necessary for the transcription and translation of a gene.

Abbreviation

| HTS | High-throughput Screen |
|---|---|
| FP | fluorescence polarization |
| FRET | Fluorescence Resonance Energy Transfer |
| HPLC | high-performance liquid chromatography |
| FPLC | fast performance liquid chromatography |
| FACS | Fluorescence activated cell sorter |

4. BRIEF DESCRIPTION OF THE DRAWINGS

FIG. 1: Substrates for HTS Fluorescent screening. The endogenous tRNA is shown in panel A; the hybridized tRNA substrate is shown in panel B; and the circularly permuted tRNA substrate is shown in panel C. The 5' ss designates the 5' splice site and 3' ss designates the 3' splice site.

5. DETAILED DESCRIPTION OF THE INVENTION

The present invention provides methods for identifying compounds that modulate fungal tRNA splicing endonuclease. In particular, the invention provides simple, rapid and sensitive methods for identifying compounds that inhibit fungal tRNA splicing endonuclease. The cell-based and cell-free assays described herein can be utilized in a high-throughput format to screen libraries of compounds to identify those compounds that inhibit fungal tRNA splicing endonuclease.

Reporter gene-based assays can be utilized to identify a compound that modulates the activity of a fungal tRNA splicing endonuclease. The reporter gene-based assays described herein may be conducted by contacting a compound with a cell genetically engineered to express a nucleic acid comprising a reporter gene, wherein said reporter gene comprises a tRNA intron, and measuring the expression of said reporter gene. Alternatively, the reporter gene-based assays may be conducted by contacting a compound with a fungal cell-free extract and a nucleic acid comprising a reporter gene, wherein said reporter gene comprises a tRNA intron, and measuring the expression of said reporter gene. The alteration in reporter gene expression relative to a previously determined reference range, or to the expression in the absence of the compound or the presence of an appropriate control (e.g., a negative control, such as PBS) in such reporter-gene based assays indicates that a particular compound modulates the activity of a fungal tRNA splicing endonuclease.

FRET assays can be utilized to identify a compound that modulates the activity of a fungal tRNA splicing endonuclease. The FRET cell-based assays described herein may be conducted by microinjecting or transfecting (e.g., using liposomes or electroporation) a substrate for a fungal tRNA splicing endonuclease into a cell and contacting the cell with a compound, wherein the substrate is labeled at the 5' end with a fluorophore and labeled at the 3' end with a quencher, or, alternatively, the substrate is labeled at the 5' end with a quencher and labeled at the 3' end with a fluorophore, and measuring the fluorescence of the substrate by, e.g., fluorescence microscopy or a fluorescence emission detector such as a Viewlux or Analyst. The endogenous tRNA splicing endonuclease will cleave the substrate and result in the production of a detectable fluorescent signal. A compound that inhibits or reduces the activity of the endogenous tRNA splicing endonuclease will prevent or reduce the production of a detectable fluorescent signal. A compound that enhances the activity of the endogenous tRNA splicing endonuclease will increase the production of a detectable fluorescent signal. Alternatively, the FRET cell-based assays may be conducted by microinjecting or transfecting a substrate for a fungal tRNA splicing endonuclease into a fungal cell and contacting the cell with a compound, wherein the substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety, and measuring the fluorescence of the substrate by, e.g., fluorescence microscopy or a fluorescence emission detector such as a Viewlux or Analyst. The endogenous tRNA splicing endonuclease will cleave the substrate and result in a fluorescent emission signal by the fluorescent acceptor moiety at the wavelength of the fluorescent donor moiety. A compound that inhibits or reduces the activity of the endogenous tRNA splicing endonuclease will increase the fluorescence emission of the fluorescent acceptor moiety at the wavelength of the fluorescent donor moiety. A compound that enhances the activity of the endogenous tRNA splicing endonuclease will reduce the fluorescence emission of the fluorescence acceptor moiety at the wavelength of the fluorescent donor moiety.

The FRET cell-free assays may be conducted by contacting a substrate for a fungal tRNA splicing endonuclease with a fungal cell-free extract or a purified fungal tRNA splicing endonuclease and a compound, wherein the substrate is labeled at the 5' end with a fluorophore and labeled at the 3' end with a quencher, or, alternatively, the substrate is labeled at the 5' end with a quencher and labeled at the 3' end with fluorophore, and measuring the fluorescence of the substrate by, e.g., a fluorescence emission detector such as a Viewlux or Analyst. The tRNA splicing endonuclease will cleave the substrate and result in the production of a detectable fluorescent signal. A compound that enhances the activity of the tRNA splicing endonuclease will result in increased production of a detectable fluorescent signal. A compound that inhibits or reduces the activity of the tRNA splicing endonuclease, however, will prevent or reduce the production of a detectable fluorescent signal. Alternatively, the FRET cell-free assays may be conducted by contacting a substrate for a fungal tRNA splicing endonuclease with a fungal cell-free extract or a purified fungal tRNA splicing endonuclease and a compound, wherein the substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety, and measuring the fluorescence of the substrate by, e.g., a fluorescence emission detector such as a Viewlux or Analyst. The tRNA splicing endonuclease will cleave the substrate and result in fluorescence emission by the fluorescent donor moiety and fluorescent acceptor moiety at the wavelength of the fluorescent donor moiety. A compound that inhibits or reduces the activity of the tRNA splicing endonuclease will increase the fluorescence emission of the fluorescent acceptor moiety at the wavelength of the fluorescent donor moiety. In contrast, a compound that enhances the activity of the tRNA splicing endonuclease will reduce the fluorescence emission of the fluorescent acceptor at the wavelength of the fluorescent donor moiety.

A compound may be tested for its ability to enhance or inhibit the activity of a fungal tRNA endonuclease using a cell-free fluorescence polarization assay. A substrate of the fungal tRNA endonuclease is labeled on its 5' or 3' end such that cleavage by the fungal tRNA endonuclease results in a decrease of size of the labeled portion of the substrate and thus, in a change of fluorescence polarization. The labeled substrate of the fungal tRNA endonuclease is incubated with a fungal cell-free extract or a purified fungal tRNA splicing endonuclease and a compound to be tested. A compound that enhances the activity of the tRNA splicing endonuclease activity will increase the rotation of the substrate relative to a negative control or the absence of the compound, which will result in more of the light emitted being depolarized. In contrast, a compound that reduces the activity of the tRNA splicing endonuclease activity will decrease the rotation of the substrate relative to a negative control or the absence of the compound which will result in the emitted light remaining polarized.

Further, a compound may be tested for its ability to enhance or inhibit the activity of a fungal tRNA endonuclease using a tRNA endonuclease suppression assay or FISH assay. See, e.g., Sections 5.4.5 and 5.4.6 of the specification for further description of such assays.

The compounds identified in assays described herein that modulate fungal tRNA splicing endonuclease activity may be tested in in vitro assays (e.g., cell-based assays or cell-free assays) or in vivo assays well-known to one of skill in the art or described herein for the effect of said compounds on tRNA processing and ultimately mRNA translation. In particular, in vitro and in vivo assays well-known to one of skill in the art or described herein may be used to determine the effect of a particular compound on fungal cells versus animalia cells (preferably mammalian cells and, most preferably, human cells). Further, a particular compound identified utilizing the assays described herein may be tested in an animal model for fungal infection to determine the efficacy of the compound in the prevention, treatment or amelioration of fungal infection or a symptom thereof. In addition, the effect of a compound identified utilizing the assays described herein may be tested for its effect on an animalia tRNA splicing endonuclease.

The structure of the compounds identified in the assays described herein that modulate fungal tRNA splicing endonuclease activity can be determined utilizing assays well-known to one of skill in the art or described herein. The methods used will depend, in part, on the nature of the library screened. For example, assays or microarrays of compounds, each having an address or identifier, may be deconvoluted, e.g., by cross-referencing the positive sample to an original compound list that was applied to the individual test assays. Alternatively, the structure of the compounds identified herein may be determined using mass spectrometry, nuclear magnetic resonance ("NMR"), X-ray crystallography, or vibrational spectroscopy.

The invention encompasses the use of the compounds that inhibit or reduce the activity of a fungal tRNA splicing endonuclease which were identified in accordance with the methods described herein for the prevention, management, treatment or amelioration of a fungal infection or one or more symptoms thereof. In a specific embodiment, the invention encompasses the use of the compounds that inhibit or reduce the activity of a fungal tRNA splicing endonuclease which were identified in accordance with the methods described herein for the prevention, management, treatment or amelioration of a fungal infection or one or more symptoms thereof. The invention also encompasses the use of the compounds that inhibit or reduce the activity of a fungal tRNA splicing endonuclease which were identified in accordance with the methods described herein for disinfecting objects or rooms.

5.1 Reporter Gene Constructs, Transfected Cells and Cell Extracts

The invention provides for specific vectors comprising a reporter gene comprising a tRNA intron operably linked to one or more regulatory elements and host cells transfected with the vectors. The invention also provides for the in vitro translation of a reporter gene flanked by one or more regulatory elements. Techniques for practicing this specific aspect of this invention will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning, Volumes I and II (Glover, Ed. 1985); Oligonucleotide Synthesis (Gait, Ed. 1984); Nucleic Acid Hybridization (Hames & Higgins, Eds. 1984); Transcription and Translation (Hames & Higgins, Eds. 1984); Animal Cell Culture (Freshney, Ed. 1986); Immobilized Cells and Enzymes (IRL Press, 1986); Perbal, A Practical Guide to Molecular Cloning (1984); Gene Transfer Vectors for Mammalian Cells (Miller & Calos, Eds. 1987, Cold Spring Harbor Laboratory); Methods in Enzymology, Volumes 154 and 155 (Wu & Grossman, and Wu, Eds., respectively), (Mayer & Walker, Eds., 1987); Immunochemical Methods in Cell and Molecular Biology (Academic Press, London, Scopes, 1987), Expression of Proteins in Mammalian Cells Using Vaccinia Viral Vectors in Current Protocols in Molecular Biology, Volume 2 (Ausubel et al., Eds., 1991).

5.1.1 Reporter Genes

Any reporter gene well-known to one of skill in the art may be used in reporter gene constructs to ascertain the effect of a compound on a eukaryotic tRNA splicing endonuclease (in particular, a fungal tRNA splicing endonuclease). Reporter genes refer to a nucleotide sequence encoding a protein that is readily detectable either by its presence or activity. Reporter genes may be obtained and the nucleotide sequence of the genes determined by any method well-known to one of skill in the art. The nucleotide sequence of a reporter gene can be obtained, e.g., from the literature or a database such as GenBank. Alternatively, a polynucleotide encoding a reporter gene may be generated from nucleic acid from a suitable source. If a clone containing a nucleic acid encoding a particular reporter gene is not available, but the sequence of the reporter gene is known, a nucleic acid encoding the reporter gene may be chemically synthesized or obtained from a suitable source (e.g., a cDNA library, or a cDNA library generated from, or nucleic acid, preferably poly A+ RNA, isolated from, any tissue or cells expressing the reporter gene) by PCR amplification. Once the nucleotide sequence of a reporter gene is determined, the nucleotide sequence of the reporter gene may be manipulated using methods well-known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate reporter genes having a different amino acid sequence, for example, to create amino acid substitutions, deletions, and/or insertions.

Examples of reporter genes include, but are not limited to, luciferase (e.g., firefly luciferase, *renilla* luciferase, and click beetle luciferase), green fluorescent protein ("GFP") (e.g., green fluorescent protein, yellow fluorescent protein, red fluorescent protein, cyan fluorescent protein, and blue fluorescent protein), beta-galactosidase ("β-gal"), beta-glucoronidase, beta-lactamase, chloramphenicol acetyltransferase ("CAT"), and alkaline phosphatase ("AP"). Table 1 below lists various reporter genes and the properties of the products of the reporter genes that can be assayed. In a preferred embodiment, a reporter gene utilized in the reporter constructs is easily assayed and has an activity which is not normally found in the cell or organism of interest.

TABLE 1

Reporter Genes and the Properties of the Reporter Gene Products

| Reporter Gene | Protein Activity & Measurement |
|---|---|
| CAT (chloramphenicol acetyltransferase) | Transfers radioactive acetyl groups to chloramphenicol or detection by thin layer chromatography and autoradiography |
| GAL (b-galactosidase) | Hydrolyzes colorless galactosides to yield colored products. |
| GUS (b-glucuronidase) | Hydrolyzes colorless glucuronides to yield colored products. |
| LUC (luciferase) | Oxidizes luciferin, emitting photons |
| GFP (green fluorescent protein) | Fluorescent protein without substrate |
| SEAP (secreted alkaline phosphatase) | Luminescence reaction with suitable substrates or with substrates that generate chromophores |
| HRP (horseradish peroxidase) | In the presence of hydrogen oxide, oxidation of 3,3',5,5'-tetramethylbenzidine to form a colored complex |
| AP (alkaline phosphatase) | Luminescence reaction with suitable substrates or with substrates that generate chromophores |

5.1.1.1 Luciferase

Luciferases are enzymes that emit light in the presence of oxygen and a substrate (luciferin) and which have been used for real-time, low-light imaging of gene expression in cell cultures, individual cells, whole organisms, and transgenic organisms (reviewed by Greer & Szalay, 2002, Luminescence 17(1):43-74).

As used herein, the term "luciferase" is intended to embrace all luciferases, or recombinant enzymes derived from luciferases which have luciferase activity. The luciferase genes from fireflies have been well characterized, for example, from the *Photinus* and *Luciola* species (see, e.g., International Publication No. WO 95/25798 for *Photinus pyralis*, European Patent Application No. EP 0 524 448 for *Luciola cruciata* and *Luciola laterals*, and Devine et al., 1993, Biochim. Biophys. Acta 1173(2):121-132 for *Luciola mingrelica*). Other eucaryotic luciferase genes include, but are not limited to, the click beetle (*Photinus plagiophthalamus*, see, e.g., Wood et al., 1989, Science 244:700-702), the sea panzy (*Renilla reniformis*, see, e.g., Lorenz et al., 1991, Proc Natl Acad Sci USA 88(10):4438-4442), and the glow worm (*Lampyris noctiluca*, see e.g., Sula-Newby et al., 1996, Biochem J. 313:761-767). The click beetle is unusual in that different members of the species emit bioluminescence of different colors, e.g., beetles may emit light at 546 nm (green), 560 nm (yellow-green), 578 nm (yellow) and 593 nm (orange) (see, e.g, U.S. Pat. Nos. 6,475,719; 6,342,379; and 6,217,847, the disclosures of which are incorporated by reference in their entireties). Bacterial luciferin-luciferase systems include, but are not limited to, the bacterial lux genes of terrestrial *Photorhabdus luminescens* (see, e.g., Manukhov et al., 2000, Genetika 36(3):322-30) and marine bacteria *Vibrio fischeri* and *Vibrio harveyi* (see, e.g., Miyamoto et al., 1988, J Biol Chem. 263(26):13393-9, and Cohn et al., 1983, Proc Natl Acad Sci USA., 80(1):120-3, respectively). The luciferases encompassed by the present invention also includes the mutant luciferases described in U.S. Pat. No. 6,265,177 to Squirrell et al., which is hereby incorporated by reference in its entirety.

In a preferred embodiment, the luciferase is a firefly luciferase, a *renilla* luciferase, or a click beetle luciferase, as described in any one of the references listed supra, the disclosures of which are incorporated by reference in their entireties.

5.1.1.2 Green Fluorescent Protein

Green fluorescent protein ("GFP") is a 238 amino acid protein with amino acid residues 65 to 67 involved in the formation of the chromophore which does not require additional substrates or cofactors to fluoresce (see, e.g., Prasher et al., 1992, Gene 111:229-233; Yang et al., 1996, Nature Biotechnol. 14:1252-1256; and Cody et al., 1993, Biochemistry 32:1212-1218).

As used herein, the term "green fluorescent protein" or "GFP" is intended to embrace all GFPs (including the various forms of GFPs which exhibit colors other than green), or recombinant enzymes derived from GFPs which have GFP activity. In a preferred embodiment, GFP includes green fluorescent protein, yellow fluorescent protein, red fluorescent protein, cyan fluorescent protein, and blue fluorescent protein. The native gene for GFP was cloned from the bioluminescent jellyfish *Aequorea victoria* (see, e.g., Morin et al., 1972, J. Cell Physiol. 77:313-318). Wild-type GFP has a major excitation peak at 395 nm and a minor excitation peak at 470 nm. The absorption peak at 470 nm allows the monitoring of GFP levels using standard fluorescein isothiocyanate (FITC) filter sets. Mutants of the GFP gene have been found useful to enhance expression and to modify excitation and fluorescence. For example, mutant GFPs with alanine, glycine, isoleucine, or threonine substituted for serine at position 65 result in mutant GFPs with shifts in excitation maxima and greater fluorescence than wild type protein when excited at 488 nm (see, e.g., Heim et al., 1995, Nature 373:663-664; U.S. Pat. No. 5,625,048; Delagrave et al., 1995, Biotechnology 13:151-154; Cormack et al., 1996, Gene 173:33-38; and Cramer et al., 1996, Nature Biotechnol. 14:315-319). The ability to excite GFP at 488 nm permits the use of GFP with standard fluorescence activated cell sorting ("FACS") equipment. In another embodiment, GFPs are isolated from organisms other than the jellyfish, such as, but not limited to, the sea pansy, *Renilla reriformis*.

Techniques for labeling cells with GFP in general are described in U.S. Pat. Nos. 5,491,084 and 5,804,387, which are incorporated by reference in their entireties; Chalfie et al., 1994, Science 263:802-805; Heim et al., 1994, Proc. Natl. Acad. Sci. USA 91:12501-12504; Morise et al., 1974, Biochemistry 13:2656-2662; Ward et al: 1980, Photochem. Photobiol. 31:611-615; Rizzuto et al., 1995, Curr. Biology 5:635-642; and Kaether & Gerdes, 1995, FEBS Lett 369:267-271. The expression of GFPs in *E. coli* and *C. elegans* are described in U.S. Pat. No. 6,251,384 to Tan et al., which is incorporated by reference in its entirety. The expression of GFP in plant cells is discussed in Hu & Cheng, 1995, FEBS Lett 369:331-33, and GFP expression in *Drosophila* is described in Davis et al., 1995, Dev. Biology 170:726-729.

5.1.1.3 Beta-galactosidase

Beta galactosidase ("β-gal") is an enzyme that catalyzes the hydrolysis of β-galactosides, including lactose, and the galactoside analogs o-nitrophenyl-b-D-galactopyranoside ("ONPG") and chlorophenol red-b-D-galactopyranoside ("CPRG") (see, e.g., Nielsen et al., 1983 Proc Natl Acad Sci USA 80(17):5198-5202; Eustice et al., 1991, Biotechniques 11:739-742; and Henderson et al., 1986, Clin. Chem. 32:1637-1641). The β-gal gene functions well as a reporter gene because the protein product is extremely stable, resistant to proteolytic degradation in cellular lysates, and easily assayed. When ONPG is used as the substrate, β-gal activity can be quantitated with a spectrophotometer or microplate reader.

As used herein, the term "beta galactosidase" or "β-gal" is intended to embrace all β-gals, including lacZ gene products, or recombinant enzymes derived from β-gals which have β-gal activity. The β-gal gene functions well as a reporter gene because the protein product is extremely stable, resistant to proteolytic degradation in cellular lysates, and easily assayed. In an embodiment where ONPG is the substrate, β-gal activity can be quantified with a spectrophotometer or microplate reader to determine the amount of ONPG converted at 420 nm. In an embodiment when CPRG is the substrate, β-gal activity can be quantitated with a spectrophotometer or microplate reader to determine the amount of CPRG converted at 570 to 595 nm. In yet another embodiment, the β-gal activity can be visually ascertained by plating bacterial cells transformed with a β-gal construct onto plates containing Xgal and IPTG. Bacterial colonies that are dark blue indicate the presence of high β-gal activity and colonies that are varying shades of blue indicate varying levels of β-gal activity.

5.1.1.4 Beta-glucoronidase

Beta-glucuronidase ("GUS") catalyzes the hydrolysis of a very wide variety of β-glucuronides, and, with much lower efficiency, hydrolyzes some β-galacturonides. GUS is very stable, will tolerate many detergents and widely varying ionic conditions, has no cofactors, nor any ionic requirements, can be assayed at any physiological pH, with an optimum between 5.0 and 7.8, and is reasonably resistant to thermal inactivation (see, e.g., U.S. Pat. No. 5,268,463, which is incorporated by reference in its entirety).

In one embodiment, the GUS is derived from the *Esherichia coli* β-glucuronidase gene. In alternate embodiments of the invention, the β-glucuronidase encoding nucleic acid is homologous to the *E. coli* β-glucuronidase gene and/or may be derived from another organism or species.

GUS activity can be assayed either by fluorescence or spectrometry, or any other method described in U.S. Pat. No. 5,268,463, the disclosure of which is incorporated by reference in its entirety. For a fluorescent assay, 4-trifluoromethylumbelliferyl β-D-glucuronide is a very sensitive substrate for GUS. The fluorescence maximum is close to 500 nm—bluish green, where very few plant compounds fluoresce or absorb. 4-trifluoromethylumbelliferyl β-D-glucuronide also fluoresces much more strongly near neutral pH, allowing continuous assays to be performed more readily than with MUG. 4-trifluoromethylumbelliferyl β-D-glucuronide can be used as a fluorescent indicator in vivo. The spectrophotometric assay is very straightforward and moderately sensitive (Jefferson et al., 1986, Proc. Natl. Acad. Sci. USA 86:8447-8451). A preferred substrate for spectrophotometric measurement is p-nitrophenyl β-D-glucuronide, which when cleaved by GUS releases the chromophore p-nitrophenol. At a pH greater than its $pK_a$ (around 7.15) the ionized chromophore absorbs light at 400-420 nm, giving a yellow color.

5.1.1.5 Beta-lactamase

Beta-lactamases are nearly optimal enzymes in respect to their almost diffusion-controlled catalysis of β-lactam hydrolysis, making them suited to the task of an intracellular reporter enzyme (see, e.g., Christensen et al., 1990, Biochem. J. 266: 853-861). They cleave the β-lactam ring of β-lactam antibiotics, such as penicillins and cephalosporins, generating new charged moieties in the process (see, e.g., O'Callaghan et al., 1968, Antimicrob. Agents. Chemother. 8: 57-63 and Stratton, 1988, J. Antimicrob. Chemother. 22, Suppl. A: 23-35). A large number of β-lactamases have been isolated and characterized, all of which would be suitable for use in accordance with the present invention (see, e.g., Richmond & Sykes, 1978, Adv. Microb. Physiol. 9:31-88 and Ambler, 1980, Phil. Trans. R. Soc. Lond. [Ser.B.] 289: 321-331, the disclosures of which are incorporated by reference in their entireties).

The coding region of an exemplary β-lactamase employed has been described in U.S. Pat. No. 6,472,205, Kadonaga et al., 1984, J. Biol. Chem. 259: 2149-2154, and Sutcliffe, 1978, Proc. Natl. Acad. Sci. USA 75: 3737-3741, the disclosures of which are incorporated by reference in their entireties. As would be readily apparent to those skilled in the field, this and other comparable sequences for peptides having β-lactamase activity would be equally suitable for use in accordance with the present invention. The combination of a fluorogenic substrate described in U.S. Pat. Nos. 6,472,205, 5,955,604, and 5,741,657, the disclosures of which are incorporated by reference in their entireties, and a suitable β-lactamase can be employed in a wide variety of different assay systems, such as are described in U.S. Pat. No. 4,740,459, which is hereby incorporated by reference in its entirety.

5.1.1.6 Chloramphenicol Acetyltransferase

Although suitable for a variety of wide-ranging applications, Chloramphenicol acetyl transferase ("CAT") is most commonly used as a reporter gene in mammalian cell systems because mammalian cells do not have detectable levels of CAT activity. While CAT, as a reporter gene, may be of limited benefit in tests of fungal tRNA splicing endonuclease activity, CAT as a reporter gene may be beneficial when investigating differential effects on fungal tRNA splicing endonuclease activity compared to effects on animalia (particularly, mammalian, and more particularly, human) tRNA splicing endonuclease, e.g., in attempts to assess potential severity of side effects of antifungal therapies. The assay for CAT involves incubating cellular extracts with radiolabeled chloramphenicol and appropriate co-factors, separating the starting materials from the product by, for example, thin layer chromatography ("TLC"), followed by scintillation counting (see, e.g., U.S. Pat. No. 5,726,041, which is hereby incorporated by reference in its entirety).

As used herein, the term "chloramphenicol acetyltransferase" or "CAT" is intended to embrace all CATs, or recombinant enzymes derived from CAT which have CAT activity. While it would be preferable that a reporter system be used which does not require cell processing, radioisotopes, and chromatographic separations as more amenable to high-throughput screening, CAT as a reporter gene may be preferable in situations when stability of the reporter gene is important. For example, the CAT reporter protein has an in vivo half life of about 50 hours, which is advantageous when an accumulative versus a dynamic change type of result is desired.

5.1.1.7 Secreted Alkaline Phosphatase

The secreted alkaline phosphatase ("SEAP") enzyme is a truncated form of alkaline phosphatase, in which the cleavage of the transmembrane domain of the protein allows it to be secreted from the cells into the surrounding media. In a preferred embodiment, the alkaline phosphatase is isolated from human placenta.

As used herein, the term "secreted alkaline phosphatase" or "SEAP" is intended to embrace all SEAP or recombinant enzymes derived from SEAP which have alkaline phosphatase activity. SEAP activity can be detected by a variety of methods including, but not limited to, measurement of catalysis of a fluorescent substrate, immunoprecipitation, HPLC, and radiometric detection. The luminescent method is preferred due to its increased sensitivity over calorimetric detection methods. The advantages of using SEAP is that a cell lysis step is not required since the SEAP protein is secreted out of the cell, which facilitates the automation of sampling and assay procedures. A cell-based assay using SEAP for use in cell-based assessment of inhibitors of the Hepatitis C virus protease is described in U.S. Pat. No. 6,280,940 to Potts et al. which is hereby incorporated by reference in its entirety.

5.1.2 tRNA Introns

Any nucleotide sequence recognized and excised by a eukaryotic (in particular, a fungal) tRNA splicing endonuclease may be inserted into the coding region of a reporter gene such that the mRNA coding the reporter gene is out of frame. Well-known molecular biology techniques can be utilized to insert such a nucleotide sequence into the coding region of the reporter gene. For example, a nucleotide sequence comprising a bulge-helix-bulge structure or a mature domain of a precursor tRNA may be inserted into the coding region of a reporter gene such that the mRNA coding the reporter gene is out of frame. Alternatively, a nucleotide sequence recognized and excised by a eukaryotic (in particular, a fungal) tRNA splicing endonuclease may be inserted into the 5' untranslated region, 3' untranslated region or both the 5' and 3' untranslated regions of a reporter gene construct. A nucleotide sequence recognized and excised by a eukaryotic (in particular, a fungal) tRNA splicing endonuclease may comprise 10 nucleotides, 15 nucleotides, 20 nucleotides, 25 nucleotides, 25 nucleotides, 30 nucleotides, 40 nucleotides, 45 nucleotides, 50 nucleotides, 55 nucleotides, 60 nucleotides, 65 nucleotides, 75 nucleotides, 100 nucleotides, 125 nucleotides, 150 nucleotides, or more. In certain embodiments, the nucleotide sequence is at least 10 nucleotides in length.

In a specific embodiment, a tRNA intron is inserted within the open reading frame of a reporter gene. In another embodiment, two, three, four, five or more tRNA introns are inserted within the open reading frame of a reporter gene. In an alternative embodiment, a tRNA intron is inserted within the 5' untranslated region, 3' untranslated region or both the 5' and 3' untranslated region of a reporter gene construct. In an alternative embodiment, two, three, four, five or more tRNA introns are inserted within the 5' untranslated region, 3' untranslated region or both the 5' and 3' untranslated region of a reporter gene construct. The tRNA intron may comprise a bulge-helix-bulge conformation.

A reporter gene containing a tRNA intron may be produced by any method well-known to one of skill in the art. For example, the reporter gene containing a tRNA intron may be chemically synthesized using phosphoramidite or other solution or solid-phase methods. Detailed descriptions of the chemistry used to form polynucleotides by the phosphoramidite method are well known (see, e.g., Caruthers et al, U.S. Pat. Nos. 4,458,066 and 4,415,732; Caruthers et al., 1982, Genetic Engineering 4:1-17; *Users Manual Model* 392 *and* 394 *Polynucleotide Synthesizers,* 1990, pages 6-1 through 6-22, Applied Biosystems, Part No. 901237; Ojwang et al., 1997, Biochemistry, 36:6033-6045). After synthesis, the reporter gene containing a tRNA intron can be purified using standard techniques known to those skilled in the art (see Hwang et al., 1999, Proc. Natl. Acad. Sci. USA 96(23): 12997-13002 and references cited therein). Depending on the length of the reporter gene containing a tRNA intron and the method of its synthesis, such purification techniques include, but are not limited to, reverse-phase high-performance liquid chromatography ("reverse-phase HPLC"), fast performance liquid chromatography ("FPLC"), and gel purification. Methods for labeling the substrate with a fluorescent acceptor moiety, a fluorescent donor moiety and/or quencher are well-known in the art (see, e.g., U.S. Pat. Nos. 6,472,156, 6,451,543, 6,348,322, 6,342,379, 6,323,039, 6,297,018, 6,291,201, 6,280,981, 5,843,658, and 5,439,797, the disclosures of which are incorporated by reference in their entirety).

5.1.3 Vectors

The nucleotide sequence coding for a reporter gene and the nucleotide sequence coding for a tRNA intron can be inserted into an appropriate expression vector, i.e., a vector which contains the necessary elements for the transcription and translation of the inserted protein-coding sequence. The necessary transcriptional and translational signals can also be supplied by the reporter gene. A variety of host-vector systems may be utilized to express the reporter gene, and particular systems may be especially amenable for conducting control comparisons between effects of putative antifungal compounds on fungal systems compared to those of other eukaryotes, particularly mammals. This is an especially important consideration, as an ideal antifungal will have demonstrable potency against fungal cells while possessing no or little adverse impact on cells of other eukaryotes. Such relevant host-vector systems include, but are not limited to, mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA; and stable cell lines generated by transformation using a selectable marker. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric nucleic acid consisting of appropriate transcriptional/translational control signals and the protein coding sequences. These methods may include in vitro recombinant DNA and synthetic techniques and in vivo recombinants (genetic recombination). Expression of the reporter gene construct may be regulated by a second nucleic acid sequence so that the reporter gene is expressed in a host transformed with the recombinant DNA molecule. For example, expression of a reporter gene construct may be controlled by any promoter/enhancer element known in the art, such as a constitutive promoter, a tissue-specific promoter, or an inducible promoter. Specific examples of promoters which may be used to control gene expression include, but are not limited to, the SV40 early promoter region (Bernoist & Chambon, 1981, Nature 290: 304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region, which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region, which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region, which is active in testicular, breast, lymphoid and mast cells (Leder et al., 1986, Cell 45:485-495), albumin gene control region, which is active in liver (Pinkert et al., 1987, Genes and Devel. 1:268-276), alpha-fetoprotein gene control region, which is active in liver (Krumlauf et al., 1985, Mol. Cell. Biol. 5:1639-1648; Hammer et al., 1987, Science 235:53-58; alpha 1-antitrypsin gene control region, which is active in the liver (Kelsey et al., 1987, Genes and Devel. 1:161-171), beta-globin gene control region, which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, a vector is used that comprises a promoter operably linked to a reporter gene, one or more origins of replication, and, optionally, one or more selectable markers (e.g., an antibiotic resistance gene). In a preferred embodiment, the vectors are CMV vectors, T7 vectors, lac vectors, pCEP4 vectors, 5.0/F vectors, or vectors with a tetracycline-regulated promoter (e.g., pcDNA™5/FRT/TO from Invitrogen).

Expression vectors containing the reporter gene construct of the present invention can be identified by three general approaches: (a) nucleic acid hybridization, (b) presence or absence of "marker" nucleic acid functions, (c) expression of inserted sequences, and (d) sequencing. In the first approach, the presence of the reporter gene inserted in an expression vector can be detected by nucleic acid hybridization using probes comprising sequences that are homologous to the inserted reporter gene. In the second approach, the recombinant vector/host system can be identified and selected based upon the presence or absence of certain "marker" nucleic acid functions (e.g., thymidine kinase activity, resistance to antibiotics, transformation phenotype, occlusion body formation in baculovirus, etc.) caused by the insertion of the nucleic acid of interest, i.e., the reporter gene construct, in the vector. For example, if the nucleic acid of interest is inserted within the marker nucleic acid sequence of the vector, recombinants containing the insert can be identified by the absence of the marker nucleic acid function. In the third approach, recombinant expression vectors can be identified by assaying the reporter gene product expressed by the recombinant. Such assays can be based, for example, on the physical or functional properties of the particular reporter gene.

In a preferred embodiment, the reporter gene constructs are cloned into stable cell line expression vectors. In a specifically preferred embodiment, the stable cell line expression vector contains a site-specific genomic integration site.

5.1.4 Transfection

Once a vector encoding the appropriate gene has been synthesized, a host cell is transformed or transfected with the vector of interest. The use of stable transformants is preferred. In a particular embodiment, the host cells are primary cells isolated from a tissue or other biological sample of interest. In a preferred embodiment, the host cells are fungal cells; however, other host cell systems may be used, particularly in determining the specificity of a specific compound for a fungal tRNA splicing endonuclease as opposed to an animalia tRNA splicing endonuclease. Host cells that can be used in the methods of the present invention include, but are not limited to, animalia cells, such as hybridomas, pre-B cells, 293 cells, 293T cells, HeLa cells, HepG2 cells, K562 cells, 3T3 cells, and fungal cells. Fungal cells that may be used in the methods of the present invention include, but are not limited to, such examples as yeast (*Saccharomyces*) HA1, HA2, HA12, HB1, HB2, HB12, and cells from such fungal species as *Aspergillus, Neurospora, Fusarium, Nectria, Neurospora*, among a multitude of other fungal species. In a specific embodiment, the host cells are immortalized cell lines derived from a source, e.g., a tissue. Other host cells that can be used in the present invention include, but are not limited to, virally-infected cells.

Transformation may be accomplished by any known method for introducing polynucleotides into a host cell, including, for example, packaging the polynucleotide in a virus and transducing a host cell with the virus, and by direct uptake of the polynucleotide. The transformation procedure used depends upon the host to be transformed. Mammalian transformations by direct uptake may be conducted using the calcium phosphate precipitation method of Graham & Van der Eb, 1978, Virol. 52:546, or the various known modifications thereof. Other methods for introducing recombinant polynucleotides into cells, particularly into mammalian cells, include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei. Such methods are well known to one of skill in the art.

In a preferred embodiment, stable cell lines containing the constructs of interest are generated for high-throughput screening. Such stable cells lines may be generated by introducing a reporter gene construct comprising a selectable marker, allowing the cells to grow for 1-2 days in an enriched medium, and then growing the cells on a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, anti-metabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

5.1.5 Cell-free Extracts

The invention provides for the translation of the reporter gene constructs in a cell-free system. In a preferred embodiment, the cell-free extracts are fungal cell-free extracts. Techniques for practicing this specific aspect of this invention will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning, Volumes I and II (Glover, Ed. 1985); and Transcription and Translation (Hames & Higgins, Eds. 1984).

Any technique well-known to one of skill in the art may be used to generate cell-free extracts for translation in vitro. For example, the cell-free extracts for in vitro translation reactions can be generated by centrifuging cells and clarifying the supernatant. In particular, a cell extract utilized in accordance with the invention may be an S1 extract (i.e., the supernatant from a 1,000×g spin) to an S500 extract (i.e., the supernatant from a 500,000×g spin), preferably an S10 extract (i.e., the supernatant from a 10,000×g spin) to an S250 extract (i.e., the supernatant from a 250,000×g spin). In a specific embodiment, a cell extract utilized in accordance with the invention is an S50 extract (i.e., the supernatant from a 50,000×g spin) to an S100 extract (i.e., the supernatant from a 100,000×g spin).

The cell-free translation extract may be isolated from cells of any species origin. For example, the cell-free translation extract may be isolated from human cells, cultured mouse cells, cultured rat cells, Chinese hamster ovary (CHO) cells, *Xenopus* oocytes, rabbit reticulocytes, wheat germ, or rye embryo (see, e.g., Krieg & Melton, 1984, Nature 308:203 and Dignam et al., 1990 Methods Enzymol. 182:194-203). Alternatively, the cell-free translation extract, e.g., rabbit reticulocyte lysates and wheat germ extract, can be purchased from, e.g., Promega, (Madison, Wis.). Fungal extract that may be used in the methods of the present invention include, but are not limited to, extracts from yeast (*Saccharomyces*) HA1, HA2, HA12, HB1, HB2, HB12, and such fungal species as *Aspergillus, Neurospora, Fusarium, Nectria, Sordaria* and a disparate variety of other fungal species.

5.2 Purification of tRNA Splicing Endonuclease

Eukaryotic (in particular, fungal) tRNA splicing endonuclease subunits and eukaryotic (in particular, fungal) tRNA splicing endonuclease can be expressed and purified by any method known to the skilled artisan. A eukaryotic tRNA splicing endonuclease subunit or the eukaryotic tRNA splicing endonuclease can be expressed by recombinant DNA technology. In specific embodiments, a eukaryotic tRNA splicing endonuclease subunit is fused to a peptide tag to facilitate purification of the subunit or the tRNA splicing endonuclease. In other embodiments, the endogenous eukaryotic tRNA splicing endonuclease is purified.

In a specific embodiment, the procedure described in Trotta et al., 1997, Cell 89:849-858 is used to purify a fungal (in particular, yeast) tRNA splicing endonuclease. In specific embodiments, recombinant fungal tRNA splicing endonuclease is purified and used in accordance with the methods of the invention. In other embodiments, partially purified fungal tRNA splicing endonuclease from any fungus is used in the methods of the invention.

In certain embodiments, recombinant human tRNA splicing endonuclease is purified and used with the methods of the invention. In other embodiments, partially purified human tRNA splicing endonuclease from any human cell source is used with the methods of the invention.

5.2.1 Recombinant DNA

In various embodiments, a eukaryotic tRNA splicing endonuclease subunit is encoded by a specific nucleotide sequence which is to be transcribed and translated. The nucleotide sequence is inserted into an expression vector for propagation and expression in recombinant cells. Eukaryotic tRNA splicing endonuclease is a heterotetramer, each of the four subunits may be expressed together in the same cell or separately in different cells; the subunits isolated and then combined to produce tRNA splicing endonuclease. Preferably, the tRNA splicing endonuclease subunits are expressed in the same cell and the functional tRNA splicing endonuclease is isolated or purified from the cell.

An expression construct, as used herein, refers to a nucleotide sequence encoding one, two, three or four eukaryotic tRNA splicing endonuclease subunits (preferably, fungal tRNA splicing endonuclease subunits) operably linked to one or more regulatory regions or enhancer/promoter sequences which enables the expression of fungal tRNA splicing endonuclease subunits in an appropriate host cell. "Operably linked" refers to an association in which the regulatory regions and the nucleotide sequence encoding a eukaryotic tRNA splicing endonuclease subunit that is to be expressed are joined and positioned in such a way as to permit transcription, and ultimately, translation.

The regulatory regions necessary for transcription of a eukaryotic tRNA splicing endonuclease subunit can be provided by the expression vector. In a compatible host-construct system, cellular transcriptional factors, such as RNA polymerase, will bind to the regulatory regions on the expression construct to effect transcription of a eukaryotic tRNA splicing endonuclease subunit in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5'-non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

Constitutive, tissue-specific and/or inducible regulatory regions may be used for expression of a eukaryotic tRNA splicing endonuclease subunit. It may be desirable to use inducible promoters when the conditions optimal for growth of the host cells and the conditions for high level expression of the eukaryotic tRNA splicing endonuclease subunit are different. Examples of useful regulatory regions are provided below.

In order to attach DNA sequences with regulatory functions, such as promoters, to the sequence encoding a eukaryotic tRNA splicing endonuclease subunit or to insert the sequence encoding a fungal tRNA splicing endonuclease subunit into the cloning site of a vector, linkers or adapters providing the appropriate compatible restriction sites may be ligated to the ends of the cDNAs by techniques well known in the art (Wu et al., 1987, Methods in Enzymol 152:343-349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

An expression construct comprising a sequence encoding a eukaryotic tRNA splicing endonuclease subunit operably linked to regulatory regions (enhancer/promoter sequences) can be directly introduced into appropriate host cells for expression and production of a eukaryotic tRNA splicing endonuclease subunit without further cloning. The expression constructs can also contain DNA sequences that facilitate integration of the sequence encoding a eukaryotic tRNA splicing endonuclease subunit into the genome of the host cell, e.g., via homologous recombination. In this instance, it is not necessary to employ an expression vector comprising a replication origin suitable for appropriate host cells in order to propagate and express a eukaryotic tRNA splicing endonuclease subunit in the host cells.

A variety of expression vectors may be used in the present invention which include, but are not limited to, plasmids, cosmids, phage, phagemids, or modified viruses. Typically, such expression vectors comprise a functional origin of replication for propagation of the vector in an appropriate host cell, one or more restriction endonuclease sites for insertion of the sequence encoding the eukaryotic tRNA splicing endonuclease subunit, and one or more selection markers. The expression vector must be used with a compatible host cell which may be derived from a prokaryotic or an eukaryotic organism including, but not limited to bacteria, yeasts, insects, mammals, and humans.

Vectors based on $E.$ $coli$ are the most popular and versatile systems for high-level expression of foreign proteins (Makrides, 1996, Microbiol Rev, 60:512-538). Non-limiting examples of regulatory regions that can be used for expression in $E.$ $coli$ may include, but not limited to lac, trp, lpp, phoA, recA, tac, T3, T7 and $\lambda P_L$ (Makrides, 1996, Microbiol Rev, 60:512-538). Non-limiting examples of prokaryotic expression vectors may include the $\lambda$gt vector series such as $\lambda$gt11 (Huynh et al., 1984 in "DNA Cloning Techniques", Vol. I: A Practical Approach (D. Glover, ed.), pp. 49-78, IRL Press, Oxford), and the pET vector series (Studier et al., 1990, Methods Enzymol., 185:60-89). However, a potential drawback of a prokaryotic host-vector system is the inability to perform many of the post-translational processing of eukaryotic cells. Thus, a eukaryotic host-vector system is preferred, and a fungal host-vector system is more preferred.

For expression of a eukaryotic tRNA splicing endonuclease subunit in mammalian host cells, a variety of regulatory regions can be used, for example, the SV40 early and late promoters, the cytomegalovirus (CMV) immediate early promoter, and the Rous sarcoma virus long terminal repeat (RSV-LTR) promoter. Inducible promoters that may be useful in mammalian cells include, but are not limited to, those associated with the metallothionein II gene, mouse mammary tumor virus glucocorticoid responsive long terminal repeats (MMTV-LTR), β-interferon gene, and hsp70 gene (Williams et al., 1989, Fungal infection Res. 49:2735-42; Taylor et al., 1990, Mol. Cell Biol., 10:165-75). It may be advantageous to use heat shock promoters or stress promoters to drive expression of a eukaryotic tRNA splicing endonuclease subunit in recombinant host cells.

In addition, the expression vector may contain selectable or screenable marker genes for initially isolating, identifying or tracking host cells that contain DNA encoding the elected eukaryotic tRNA splicing endonuclease subunit. For long term, high-yield production of a eukaryotic tRNA splicing endonuclease subunit, stable expression in cells is preferred. A number of selection systems may be used under proper conditions, including, but not limited to the Herpes simplex virus thymidine kinase (Wigler et al., 1977, Cell 11:223), hypoxanthine-guanine phosphoribosyltransferase (Szybalski and Szybalski, 1962, Proc. Natl. Acad. Sci. USA 48:2026), and adenine phosphoribosyltransferase (Lowy et al., 1980, Cell 22:817) genes can be employed in tk⁻, hgprt⁻ or aprt⁻ cells, respectively. Also, antimetabolite resistance can be used as the basis of selection for dihydrofolate reductase (dhfr), which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neomycin phosphotransferase (neo), which confers resistance to the aminoglycoside G-418 (Colberre-Garapin et al., 1981, J. Mol. Biol. 150:1); and hygromycin phosphotransferase (hyg), which confers resistance to hygromycin (Santerre et al., 1984, Gene 30:147). Other selectable markers, such as but not limited to histidinol and Zeocin™ can also be used.

5.2.2 Production of Recombinant Proteins 5.2.2.1 Peptide Tagging

Generating a fusion protein comprising a peptide tag and a eukaryotic tRNA splicing endonuclease subunit (preferably, a fungal tRNA splicing endonuclease subunit) can aid the purification of the eukaryotic tRNA splicing endonuclease subunit. A fusion protein comprising a peptide and a eukaryotic tRNA splicing endonuclease subunit can be made by ligating the nucleotide sequence encoding the eukaryotic tRNA splicing endonuclease subunit to the sequence encoding the peptide tag in the proper reading frame. Care should be taken to ensure that the modified gene remains within the same translational reading frame, uninterrupted by translational stop signals and/or spurious messenger RNA splicing signals.

The peptide tag may be fused to the amino terminal or to the carboxyl terminal of a fungal tRNA splicing endonuclease subunit. The precise site at which the fusion is made is not critical. The optimal site can be determined by routine experimentation.

A variety of peptide tags known in the art may be conjugated to a eukaryotic tRNA splicing endonuclease subunit including, but not limited to the immunoglobulin constant regions, polyhistidine sequence (Petty, 1996, Metal-chelate affinity chromatography, in Current Protocols in Molecular Biology, Vol. 2, Ed. Ausubel et al., Greene Publish. Assoc. & Wiley Interscience), glutathione S-transferase (GST; Smith, 1993, Methods Mol. Cell Bio. 4:220-229), the E. coli maltose binding protein (Guan et al., 1987, Gene 67:21-30), various cellulose binding domains (U.S. Pat. Nos. 5,496,934; 5,202,247; 5,137,819; Tomme et al., 1994, Protein Eng. 7:117-123), and the FLAG epitope (Short Protocols in Molecular Biology, 1999, Ed. Ausubel et al., John Wiley & Sons, Inc., Unit 10.11). Other peptide tags that are well-known to one of skill in the art that are recognized by specific binding partners and thus facilitate isolation by affinity binding to the binding partner (which is preferably immobilized and/or on a solid support) may be conjugated to a eukaryotic tRNA splicing endonuclease subunit. As will be appreciated by those skilled in the art, many methods can be used to obtain the coding region of the above-mentioned peptide tags, including but not limited to, DNA cloning, DNA amplification, and synthetic methods. Some of the peptide tags and reagents for their detection and isolation are available commercially.

In a specific embodiment, the polyhistidine tag conjugated to a eukaryotic tRNA splicing endonuclease subunit has at least 6, at least 8, at least 10 or at least 10 histidines. In a preferred embodiment, the polyhistidine tag conjugated to a eukaryotic tRNA splicing endonuclease subunit has 8 histidines. In another embodiment, two or more different peptide tags can be used to label a eukaryotic tRNA splicing endonuclease subunit. In a preferred embodiment, a eukaryotic tRNA splicing endonuclease subunit is labeled with both a polyhistidine tag and a FLAG epitope tag. In another embodiment, one eukaryotic tRNA splicing endonuclease subunit is labeled with a first peptide tag and a second, different tRNA splicing endonuclease is labeled with a second, different peptide tag. In a preferred embodiment, a polyhistidine tag with 8 histidines is conjugated to a selected eukaryotic tRNA splicing endonuclease subunit, while a FLAG epitope tag is conjugated to another, different eukaryotic tRNA splicing endonuclease subunit.

5.2.2.2 Expression Systems and Host Cells

In fungi, a number of vectors containing constitutive or inducible promoters may be used with Saccharomyces cerevisiae (baker's yeast), Schizosaccharomyces pombe (fission yeast), Pichia pastoris, and Hansenula polymorpha (methylotropic yeasts). For a review, see Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast Saccharomyces, 1982, Eds. Strathern et al., Cold Spring Harbor Press, Vols. I and II.

Other useful eukaryotic host-vector system may include mammalian and insect systems. Mammalian host cells include but are not limited to those derived from humans, monkeys and rodents (see, e.g., Kriegler M. in "Gene Transfer and Expression: A Laboratory Manual", New York, Freeman & Co. 1990), such as monkey kidney cell line transformed by SV40 (COS-7, ATCC Accession No. CRL 1651); human embryonic kidney cell lines (293, 293-EBNA, or 293 cells subcloned for growth in suspension culture, Graham et al., J. Gen. Virol., 36:59, 1977); baby hamster kidney cells (BHK, ATCC Accession No. CCL 10); chinese hamster ovary-cells-DHFR (CHO, Urlaub and Chasin. Proc. Natl. Acad. Sci. 77:4216, 1980); mouse sertoli cells (Mather, Biol. Reprod. 23:243-251, 1980); mouse fibroblast cells (NIH-3T3), monkey kidney cells (CVI ATCC Accession No. CCL 70); african green monkey kidney cells (VERO-76, ATCC Accession No. CRL-1587); human cervical carcinoma cells (HELA, ATCC Accession No. CCL 2); canine kidney cells (MDCK, ATCC Accession No. CCL 34); buffalo rat liver cells (BRL 3A, ATCC Accession No. CRL 1442); human lung cells (W138, ATCC Accession No. CCL 75); human liver cells (Hep G2, HB 8065); and mouse mammary tumor cells (MMT 060562, ATCC Accession No. CCL51).

A number of viral-based expression systems may also be utilized with mammalian cells to produce a eukaryotic tRNA splicing endonuclease subunit (preferably, a fungal tRNA splicing endonuclease). Vectors using DNA virus backbones have been derived from simian virus 40 (SV40) (Hamer et al., 1979, Cell 17:725), adenovirus (Van Doren et al., 1984, Mol Cell Biol 4:1653), adeno-associated virus (McLaughlin et al., 1988, J Virol 62:1963), and bovine papillomas virus (Zinn et al., 1982, Proc Natl Acad Sci 79:4897). In cases where an adenovirus is used as an expression vector, the donor DNA sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing heterologous products in infected hosts. (See e.g., Logan and Shenk, 1984, Proc. Natl. Acad. Sci. (USA) 81:3655-3659).

In an insect system, *Autographa californica* nuclear polyhidrosis virus (AcNPV), a baculovirus, can be used as a vector to express the human tRNA splicing endonuclease subunit in *Spodoptera frugiperda* cells. The sequences encoding a eukaryotic tRNA splicing endonuclease subunit may be cloned into non-essential regions (for example, the polyhedrin gene) of the virus and placed under control of an AcNPV promoter (for example, the polyhedrin promoter). These recombinant viruses are then used to infect host cells in which the inserted DNA is expressed. (See e.g., Smith et al., 1983, J Virol 46:584; Smith, U.S. Pat. No. 4,215,051.)

Any of the cloning and expression vectors described herein may be synthesized and assembled from known DNA sequences by well-known techniques in the art. The regulatory regions and enhancer elements can be of a variety of origins, both natural and synthetic. Some vectors and host cells may be obtained commercially. Non-limiting examples of useful vectors are described in Appendix 5 of Current Protocols in Molecular Biology, 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

Expression constructs containing a cloned nucleotide sequence encoding a eukaryotic tRNA splicing endonuclease subunit can be introduced into the host cell by a variety of techniques known in the art, including but not limited to, bacterial transformation for prokaryotic cells (Hanahan, 1985, in DNA Cloning, A Practical Approach, 1:109-136), and, for eukaryotic cells, calcium phosphate mediated transfection (Wigler et al., 1977, Cell 11:223-232), liposome-mediated transfection (Schaefer-Ridder et al., 1982; Science 215:166-168), electroporation (Wolff et al., 1987, Proc Natl Acad Sci 84:3344), and microinjection (Cappechi, 1980, Cell 22:479-488).

For long term, high-yield production of a properly processed eukaryotic tRNA splicing endonuclease subunit, stable expression in eukaryotic cells of the same species is preferred. Cell lines that stably express a eukaryotic tRNA splicing endonuclease subunit may be engineered by using a vector that contains a selectable marker. By way of example but not limitation, following the introduction of the expression constructs, engineered cells may be allowed to grow for 1-2 days in an enriched media, and then are switched to a selective media. The selectable marker in the expression construct confers resistance to the selection and optimally allows cells to stably integrate the expression construct into their chromosomes and to grow in culture and to be expanded into cell lines. Such cells can be cultured for a long period of time while a eukaryotic tRNA splicing endonuclease subunit is expressed continuously.

5.2.2.3 Protein Purification

Generally, a eukaryotic tRNA splicing endonuclease subunit (preferably, a fungal tRNA splicing endonuclease subunit) or the eukaryotic tRNA splicing endonuclease (preferably, a fungal tRNA splicing endonuclease) can be recovered and purified from recombinant cell cultures by known methods, including ammonium sulfate precipitation, acid extraction, anion or cation exchange chromatography, phosphocellulose chromatography, immunoaffinity chromatography, hydroxyapatite chromatography, and lectin chromatography. In a preferred embodiment, the eukaryotic tRNA splicing endonuclease subunit or eukaryotic tRNA splicing endonuclease is a fungal tRNA splicing endonuclease subunit or a fungal tRNA splicing endonuclease, respectively. In another preferred embodiment, the fungal tRNA splicing endonuclease subunit or fungal tRNA splicing endonuclease is a yeast tRNA splicing endonuclease subunit or a yeast tRNA splicing endonuclease, respectively. Before the eukaryotic tRNA splicing endonuclease subunit can be purified, total protein has to be prepared from the cell culture. This procedure comprises collection, washing and lysis of said cells and is well known to the skilled artisan.

In particular, a recombinant eukaryotic tRNA splicing endonuclease subunit fused to a peptide tag may be purified based on the properties of the peptide tag. One approach is based on specific molecular interactions between a tag and its binding partner. The other approach relies on the immuno-specific binding of an antibody to an epitope present on the tag or on the protein which is to be purified. The principle of affinity chromatography well known in the art is generally applicable to both of these approaches. Once the eukaryotic tRNA splicing endonuclease subunit-peptide tag fusion protein is eluted, fractions can be collected and tested for the presence of the eukaryotic tRNA splicing endonuclease and/or for the presence of the peptide tag. In a specific embodiment, the fractions are tested for tRNA splicing endonuclease activity. Subsequently, the fractions with tRNA splicing endonuclease activity levels over a certain threshold level can be pooled.

Described below are several methods based on specific molecular interactions of a tag and its binding partner.

A method that is generally applicable to purifying a eukaryotic tRNA splicing endonuclease subunit fused to the constant regions of immunoglobulin is protein A affinity chromatography, a technique that is well-known in the art. *Staphylococcus* protein A is a 42 kD polypeptide that binds specifically to a region located between the second and third constant regions of heavy chain immunoglobulins. Because of the Fc domains of different classes, subclasses and species of immunoglobulins, affinity of protein A for human Fc regions is strong, but may vary among species. Subclasses that are less preferred include human IgG-3, and most rat subclasses. For certain subclasses, protein G (of Streptococci) may be used in place of protein A in the purification. Protein-A sepharose (Pharmacia or Biorad) is a commonly used solid phase for affinity purification of antibodies, and can be used essentially in the same manner for the purification of a eukaryotic tRNA splicing endonuclease subunit fused to an immunoglobulin Fc fragment. Bound fungal tRNA splicing endonuclease subunit-Fc fusion protein can be eluted by various buffer systems known in the art, including a succession of citrate, acetate and glycine-HCl buffers which gradually lowers the pH. This method is less preferred if the recombinant cells also produce antibodies which will be co-purified with the tRNA splicing endonuclease subunit. See, e.g., Langone, 1982, J. Immunol. Meth. 51:3; Wilchek et al., 1982, Biochem. Intl. 4:629; Sjobring et al., 1991, J. Biol. Chem. 26:399; Antibodies: A Laboratory Manual, edited by Harlow and Lane, Cold Spring Harbor laboratory, 1988, pp. 617-618.

Alternatively, a polyhistidine tag may be used, in which case, a eukaryotic tRNA splicing endonuclease subunit can be purified by metal chelate chromatography. The polyhistidine tag, usually a sequence of six histidines, has a high affinity for divalent metal ions, such as nickel ions ($Ni^{2+}$), which can be immobilized on a solid phase, such as nitrilotriacetic acid-matrices. Polyhistidine has a well-characterized affinity for $Ni^{2+}$-NTA-agarose, and can be eluted with either of two mild treatments: imidazole (0.1-0.2 M) will effectively compete with the resin for binding sites; or lowering the pH just below 6.0 will protonate the histidine sidechains and disrupt the binding. The purification method comprises loading the cell culture lysate onto the $Ni^{2+}$-NTA-agarose column, washing the contaminants through, and eluting the fungal tRNA splicing endonuclease subunit with imidazole or weak acid. $Ni^{2+}$-NTA-agarose can be obtained from commercial suppliers such as Sigma (St. Louis) and Qiagen. Antibodies that recognize the polyhistidine tag are also available which can be used to detect and quantify the eukaryotic tRNA splicing endonuclease subunit.

Another exemplary peptide tag that can be used is the glutathione-S-transferase (GST) sequence, originally cloned from the helminth, *Schistosoma japonicum*. In general, a eukaryotic tRNA splicing endonuclease subunit-GST fusion protein expressed in a prokaryotic host cell, such as *E. coli*, can be purified from the cell culture lysate by absorption with glutathione agarose beads, followed by elution in the presence of free reduced glutathione at neutral pH. Since GST is known to form dimers under certain conditions, dimeric eukaryotic tRNA splicing endonuclease subunit may be obtained. See Smith, 1993, Methods Mol. Cell Bio. 4:220-229.

Another useful peptide tag that can be used is the maltose binding protein (MBP) of *E. coli*, which is encoded by the nale gene. A eukaryotic tRNA splicing endonuclease subunit fused to MBP binds to amylose resin while contaminants are washed away. The bound fungal tRNA splicing endonuclease subunit-MBP fusion is eluted from the amylose resin by maltose. See, for example, Guan et al., 1987, Gene 67:21-30.

The second approach for purifying a eukaryotic tRNA splicing endonuclease subunit or eukaryotic tRNA splicing endonuclease is applicable to peptide tags that contain an epitope for which polyclonal or monoclonal antibodies are available. It is also applicable if polyclonal or monoclonal antibodies specific to a eukaryotic tRNA splicing endonuclease subunit or the eukaryotic tRNA splicing endonuclease are available. Various methods known in the art for purification of protein by immunospecific binding, such as immunoaffinity chromatography, and immunoprecipitation, can be used. See, for example, Chapter 13 in Antibodies A Laboratory Manual, edited by Harlow and Lane, Cold Spring Harbor laboratory, 1988; and Chapter 8, Sections I and II, in Current Protocols in Immunology, ed. by Coligan et al., John Wiley, 1991; the disclosure of which are both incorporated by reference herein.

In particular the invention relates to the expression and purification of the Sen2p and Sen34p subunits of a eukaryotic (preferably, fungal) tRNA splicing endonuclease.

Oligonucleotides complementary to the 5' and 3' ends of the open reading frames of the eukaryotic tRNA splicing endonuclease subunits can be used to PCR amplify the open reading frames encoding the eukaryotic tRNA splicing endonuclease.

5.3 Compounds

Libraries screened using the methods of the present invention can comprise a variety of types of compounds. Examples of libraries that can be screened in accordance with the methods of the invention include, but are not limited to: peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small molecule libraries (preferably, small organic molecule libraries). In some embodiments, the compounds in the libraries screened are nucleic acid or peptide molecules. In a non-limiting example, peptide molecules can exist in a phage display library. In other embodiments, the types of compounds include, but are not limited to, peptide analogs including peptides comprising non-naturally occurring amino acids, e.g., D-amino acids, phosphorous analogs of amino acids, such as α-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used in the assays of the invention.

In a preferred embodiment, the combinatorial libraries are small organic molecule libraries including, but not limited to, benzodiazepines, isoprenoids, thiazolidinones, metathiazanones, pyrrolidines, morpholino compounds, and benzodiazepines. In another embodiment, the combinatorial libraries comprise peptoids; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available (see, e.g., ComGenex, Princeton, N.J.; Asinex, Moscow, Russia, Tripos, Inc., St. Louis, Mo.; ChemStar, Ltd., Moscow, Russia; 3D Pharmaceuticals, Exton, Pa.; Martek Biosciences, Columbia, Md.).

In a preferred embodiment, the library is preselected so that the compounds of the library are more amenable for cellular uptake. For example, compounds are selected based on specific parameters such as, but not limited to, size, lipophilicity, hydrophilicity, and hydrogen bonding, which enhance the likelihood of compounds getting into the cells. In another embodiment, the compounds are analyzed by three-dimensional or four-dimensional computer computation programs.

The combinatorial compound library for use in accordance with the methods of the present invention may be synthesized. There is a great interest in synthetic methods directed toward the creation of large collections of small organic compounds, or libraries, which could be screened for pharmacological, biological or other activity. The synthetic methods applied to create vast combinatorial libraries are performed in solution or in the solid phase, i.e., on a solid support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry.

Combinatorial compound libraries of the present invention may be synthesized using the apparatus described in U.S. Pat. No. 6,190,619 to Kilcoin et al., which is hereby incorporated by reference in its entirety. U.S. Pat. No. 6,190,619 discloses a synthesis apparatus capable of holding a plurality of reaction vessels for parallel synthesis of multiple discrete compounds or for combinatorial libraries of compounds.

In one embodiment, the combinatorial compound library can be synthesized in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non-peptides or peptides. In contrast to solid phase synthesis of combinatorial compound libraries, liquid phase synthesis does not require the use of specialized protocols for monitoring the individual steps of a multistep solid phase synthesis (Egner et al., 1995, J. Org. Chem. 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun. Mass Spect. 8:77; Chu et al., 1995, J. Am. Chem. Soc. 117:5419; Brummel et al., 1994, Science 264:399; and Stevanovic et al., 1993, Bioorg. Med. Chem. Lett. 3:431).

Combinatorial compound libraries useful for the methods of the present invention can be synthesized on solid supports. In one embodiment, a split synthesis method, a protocol of separating and mixing solid supports during the synthesis, is used to synthesize a library of compounds on solid supports (see e.g., Lam et al., 1997, Chem. Rev. 97:41-448; Ohlmeyer et al., 1993, Proc. Natl. Acad. Sci. USA 90:10922-10926 and references cited therein). Each solid support in the final library has substantially one type of compound attached to its surface. Other methods for synthesizing combinatorial libraries on solid supports, wherein one product is attached to each support, will be known to those of skill in the art (see, e.g., Nefzi et al., 1997, Chem. Rev. 97:449-472).

As used herein, the term, "solid support" is not limited to a specific type of solid support. Rather a large number of supports are available and are known to one skilled in the art. Solid supports include silica gels, resins, derivatized plastic films, glass beads, cotton, plastic beads, polystyrene beads, alumina gels, and polysaccharides. A suitable solid support may be selected on the basis of desired end use and suitability for various synthetic protocols. For example, for peptide synthesis, a solid support can be a resin such as p-methylbenzhydrylamine (pMBHA) resin (Peptides International, Louisville, Ky.), polystyrenes (e.g., PAM-resin obtained from Bachem Inc., Peninsula Laboratories), including chloromethylpolystyrene, hydroxymethylpolystyrene and aminomethylpolystyrene, poly(dimethylacrylamide)-grafted styrene co-divinyl-benzene (e.g., POLYHIPE resin, obtained from Aminotech, Canada), polyamide resin (obtained from Peninsula Laboratories), polystyrene resin grafted with polyethylene glycol (e.g., TENTAGEL or ARGOGEL, Bayer, Tubingen, Germany) polydimethylacrylamide resin (obtained from Milligen/Biosearch, California), or Sepharose (Pharmacia, Sweden).

In some embodiments of the present invention, compounds can be attached to solid supports via linkers. Linkers can be integral and part of the solid support, or they may be nonintegral that are either synthesized on the solid support or attached thereto after synthesis. Linkers are useful not only for providing points of compound attachment to the solid support, but also for allowing different groups of molecules to be cleaved from the solid support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions. In a preferred embodiment, the compounds are cleaved from the solid support prior to high-throughput screening of the compounds.

In certain embodiments of the invention, the compound is a small molecule.

5.4 In Vitro Screening Assays

Various in vitro assays can be used to identify and verify the ability of a compound to modulate the activity of a tRNA splicing endonuclease. Multiple in vitro assays can be performed simultaneously or sequentially to assess the affect of a compound on the activity of a fungal tRNA splicing endonuclease. In a preferred embodiment, the in vitro assays described herein are performed in a high-throughput format. In another preferred embodiment, the fungal tRNA splicing endonuclease utilized in the assays described herein is a yeast tRNA splicing endonuclease.

5.4.1 Reporter Gene-Based Assays 5.4.1.1 Cell-Based Assays

After a vector containing the reporter gene construct is transformed or transfected into a host cell and a compound library is synthesized or purchased or both, the cells are used to screen the library to identify compounds that modulate the activity of a fungal tRNA splicing endonuclease. The reporter gene-based assays may be conducted by contacting a compound or a member of a library of compounds with a cell genetically engineered to contain a reporter gene construct comprising a reporter gene and a tRNA intron within the open reading frame of the reporter gene, or within the 5' untranslated region, 3' untranslated region or both the 5' and 3' untranslated regions of the reporter gene construct, or within a mRNA splice site of the reporter gene; and measuring the expression of said reporter gene. The alteration in reporter gene expression relative to a previously determined reference range, the absence of the compound or presence of an appropriate control (e.g. a negative control, such as PBS) in such reporter-gene based assays indicates that a particular compound modulates the activity of a fungal tRNA splicing endonuclease. A decrease in reporter gene expression relative to a previously determined reference range, the absence of the compound or presence of an appropriate control (e.g., a negative control, such as PBS) in such reporter-gene based assays indicates that a particular compound reduces or inhibits the activity of a fungal tRNA splicing endonuclease (e.g., the recognition or cleavage of a tRNA intron). An increase in reporter gene expression relative to a previously determined reference range, the absence of the compound or the presence of an appropriate control (e.g., a negative control, such as PBS) in such reporter-gene based assays indicates that a particular compound enhances the activity of a fungal tRNA splicing endonuclease. In a preferred embodiment, a negative control (e.g., PBS or another agent that is known to have no effect on the expression of the reporter gene) and a positive control (e.g., an agent that is known to have an effect on the expression of the reporter gene, preferably an agent that effects the activity of a fungal tRNA splicing endonuclease) are included in the cell-based assays described herein.

The step of contacting a compound or a member of a library of compounds with a fungal cell genetically engineered to contain a reporter gene construct comprising a reporter gene and a tRNA intron within the open reading frame of the reporter gene, within the 5' untranslated region, 3' untranslated region or both the 5' and 3' untranslated regions of the reporter gene construct, or within a mRNA splice site, may be conducted under physiologic conditions. In specific embodiment, a compound or a member of a library of compounds is added to the cells in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but are not limited to, KCl, NaCl, and/or $MgCl_2$. The optimal concentration of each salt used in the aqueous solution is dependent on the cells and compounds used and can be determined using routine experimentation. The step of contacting a compound or a member of a library of compounds with a fungal cell genetically engineered to contain the reporter gene construct may be performed for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day.

In one embodiment, the invention provides a method for identifying a compound that modulates fungal tRNA splicing endonuclease activity, said method comprising: (a) expressing a nucleic acid comprising a reporter gene in a cell, wherein the reporter gene comprises a tRNA intron; (b) contacting said cell with a member of a library of compounds; and (c) detecting the expression of said reporter gene, wherein a compound that modulates tRNA splicing endonuclease activity is identified if the expression of said reporter gene in the presence of a compound is altered relative to a previously determined reference range or the expression of said reporter gene in the absence of the compound or the presence of an appropriate control (e.g., a negative control, such as PBS). In another embodiment, the invention provides a method for identifying a compound that modulates fungal tRNA splicing endonuclease activity, said method comprising: (a) contacting a member of a library of compounds with a cell containing a nucleic acid comprising a reporter gene, wherein the reporter gene comprises a tRNA intron; and (b) detecting the expression of said reporter gene, wherein a compound that modulates tRNA splicing endonuclease activity is identified if the expression of said reporter gene in the presence of a compound is altered relative to a previously determined reference range, the expression of said reporter gene in the absence of the compound or the presence of an appropriate control (e.g., a negative control, such as PBS).

The expression of a reporter gene in the cell-based reporter-gene assays may be detected by any technique well-known to one of skill in the art. The expression of a reporter gene can be detected by assessing protein and/or RNA expression of the reporter gene and/or the activity of the expressed reporter gene. The expression of a reporter gene can be readily detected, e.g., by quantifying the protein and/or RNA encoded by said gene. Many methods standard in the art can be thus employed, including, but not limited to, immunoassays to detect and/or visualize gene expression (e.g., Western blot, immunoprecipitation followed by sodium dodecyl sulfate polyacrylamide gel electrophoresis (SDS-PAGE), immunocytochemistry) and/or hybridization assays to detect gene expression by detecting and/or visualizing respectively mRNA encoding a gene (e.g., Northern assays, dot blots, in situ hybridization), etc. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended as limiting in any way).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody to immunoprecipitate a particular antigen (e.g., a reporter) can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current. Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (which recognizes the antigen) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$ diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding a primary antibody (which recognizes the antigen) conjugated to a detectable compound such as an enzymatic substrate (e.g., horseradish peroxidase or alkaline phosphatase) to the well and incubating for a period of time, and detecting the presence of the antigen. In ELISAs the primary antibody does not have to be conjugated to a detectable compound; instead, a second antibody (which recognizes the primary antibody) conjugated to a detectable compound may be added to the well. Further, instead of coating the well with the antigen, the antibody may be coated to the well. In this case, a second antibody conjugated to a detectable compound may be added following the addition of the antigen to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

Methods for detecting the activity of a protein encoded by a reporter gene expression will vary with the reporter gene used. Assays for the activity of the various reporter genes are well-known to one of skill in the art. For example, as described in Section 5.1.1., luciferase, beta-galactosidase ("β-gal"), beta-glucoronidase ("GUS"), beta-lactamase, chloramphenicol acetyltransferase ("CAT"); and alkaline phosphatase ("AP") are enzymes that can be analyzed in the presence of a substrate and could be amenable to high-throughput screening. For example, the reaction products of luciferase, beta-galactosidase ("β-gal"), and alkaline phosphatase ("AP") are assayed by changes in light imaging (e.g., luciferase), spectrophotometric absorbance (e.g., β-gal), or fluorescence (e.g., AP). Assays for changes in light output, absorbance, and/or fluorescence are easily adapted for high-throughput screening. For example, b-gal activity can be measured with a microplate reader. Green fluorescent protein ("GFP") activity can be measured by changes in fluorescence.

For example, in the case of mutant GFPs that fluoresce at 488 nm, standard fluorescence activated cell sorting ("FACS") equipment can be used to separate cells based upon GFP activity.

Alterations in the expression of a reporter gene may be determined by comparing the level of expression of the reporter gene to a negative control (e.g., PBS or another agent that is known to have no effect on the expression of the reporter gene) and optionally, a positive control (e.g., an agent that is known to have an effect on the expression of the reporter gene, preferably an agent that effects the activity of a fungal tRNA splicing endonuclease). Alternatively, alterations in the expression of a reporter gene may be determined by comparing the level of expression of the reporter gene to a previously determined reference range.

5.4.1.2 Cell-Free Assays

After a vector containing the reporter gene construct is produced, a cell-free translation extract is generated or purchased, and a compound library is synthesized or purchased or both, the cell-free translation extract and nucleic acid are used to screen the library to identify compounds that modulate the activity of a fungal tRNA splicing endonuclease. The reporter gene-based assays may be conducted in a cell-free manner by contacting a compound with a fungal cell-free extract and a reporter gene construct comprising a reporter gene and a tRNA intron within the open reading frame of the reporter gene or within the 5' untranslated region, 3' untranslated region or both the 5' and 3' untranslated regions of the reporter gene construct, or in a mRNA splicing site of the reporter gene, and measuring the expression of said reporter gene. The alteration in reporter gene expression relative to a previously determined reference range, the absence of the compound or presence of an appropriate control (e.g., a negative control, such as PBS) in such reporter-gene based assays indicates that a particular compound modulates the activity of a fungal tRNA splicing endonuclease. A decrease in reporter gene expression relative to a previously determined reference range, the absence of the compound or presence of a control in such reporter-gene based assays indicates that a particular compound reduces or inhibits the activity of a fungal tRNA splicing endonuclease (e.g., the recognition or cleavage of a tRNA intron). An increase in reporter gene expression relative to a previously determined reference range, the absence of the compound or presence of a control in such reporter-gene based assays indicates that a particular compound enhances the activity of a fungal tRNA splicing endonuclease. In a preferred embodiment, a negative control (e.g., PBS or another agent that is known to have no effect on the expression of the reporter gene) and a positive control (e.g., an agent that is known to have an effect on the expression of the reporter gene, preferably an agent that effects the activity of a fungal tRNA splicing endonuclease) are included in the cell-free assays described herein.

In a specific embodiment, the invention provides a method for identifying a compound that modulates fungal tRNA splicing endonuclease activity, said method comprising: (a) contacting a member of a library of compounds with a fungal cell-free extract and a nucleic acid comprising a reporter gene, wherein the reporter gene comprises a tRNA intron; and (b) detecting the expression of said reporter gene, wherein a compound that modulates the tRNA splicing endonuclease activity is identified if the expression of said reporter gene in the presence of a compound is altered relative to the expression of said reporter gene in the absence of said compound or the presence of an appropriate control.

The activity of a compound in the cell-free extract can be determined by assaying the activity of a reporter protein encoded by a reporter gene, or alternatively, by quantifying the expression of the reporter gene by, for example, labeling the in vitro translated protein (e.g., with $^{35}$S-labeled methionine), northern blot analysis, RT-PCR or by immunological methods, such as western blot analysis or immunoprecipitation. Such methods are well-known to one of skill in the art.

5.4.2 FRET Assays

Fluorescence resonance energy transfer ("FRET") can be used to detect alterations in the activity of a fungal tRNA splicing endonuclease. In the FRET assays described herein, the subunits of a fungal tRNA splicing endonuclease or a substrate for a fungal tRNA splicing endonuclease may be labeled with fluorophores. Methods for labeling substrate, as well as methods for labeling the fungal tRNA splicing endonuclease, may be readily practiced by one of skill in the art. See, e.g., Qin & Pyle, 1999, "Site-Specific Labeling of RNA with Fluorophores and Other Structural Probes," in Methods: A Companion to Methods in Enzymology 18:60-70, which is hereby incorporated by reference in its entirety. In circumstances where a subunit(s) of a fungal tRNA splicing endonuclease has not been determined or isolated, the substrate for the fungal TRNA splicing endonuclease is labeled with fluorophores.

In order to obtain FRET between the fluorescent donor moiety and the fluorescent acceptor moiety or a quencher, the two moieties have to be in spatial proximity with each other. Thus, in certain embodiments, a substrate for a fungal tRNA splicing endonuclease is labeled such that the fluorescent donor moiety and the fluorescent acceptor moiety or a quencher are at most 0.5 nm, at most 1 nm, at most 5 nm, at most 10 nm, at most 20 nm, at most 30 nm, at most 40 nm, at most 50 nm or at most 100 nm apart from each other.

5.4.2.1 Fungal Cell-Based Assays with a Labeled Substrate

The FRET cell-based assays may be conducted by microinjecting or transfecting a substrate for a fungal tRNA splicing endonuclease into a fungal cell and contacting the fungal cell with a compound, wherein the substrate is labeled at the 5' end with a fluorophore and labeled at the 3' end with a quencher, or, alternatively, the substrate is labeled at the 5' end with a quencher and labeled at the 3' end with a fluorophore, and measuring the fluorescence of the substrate by, e.g., a fluorescence emission detector such as a Viewlux or Analyst. The endogenous tRNA splicing endonuclease will cleave the substrate and result in the production of a detectable fluorescent signal. A compound that inhibits the activity of the endogenous tRNA splicing endonuclease will inhibit or reduce the cleavage of the substrate and thus, inhibit or reduce the production of a detectable fluorescent signal relative to a negative control (e.g., PBS). A compound that enhances the activity of the endogenous endonuclease will enhance the cleavage of the substrate and thus, increase the production of a detectable fluorescent signal relative to a negative control (e.g., PBS).

Alternatively, the FRET cell-based assays may be conducted by microinjecting or transfecting a substrate for a fungal tRNA splicing endonuclease into a fungal cell and contacting the fungal cell with a compound, wherein the substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety, and measuring the fluorescence of the substrate by, e.g., a fluorescence emission detector such as a Viewlux or Analyst. The endogenous tRNA splicing endonuclease will cleave the substrate and result in the production of a detectable fluorescent signal by the fluorescent donor moiety and fluorescent acceptor moiety at the wavelength of the fluorescent donor moiety. A compound that inhibits the activity of the endogenous tRNA splicing endonuclease will inhibit or reduce cleavage of the substrate and thus, increase the fluorescence emission of the fluorescent acceptor moiety at the wavelength of the fluorescent donor moiety relative to a negative control (e.g., PBS). A compound that enhances the activity of the endogenous tRNA splicing endonuclease will enhance the cleavage of the substrate and thus, reduce the fluorescence emission of the fluorescent acceptor at the wavelength of the fluorescent donor relative to a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET fungal cell-based assays described herein.

Any nucleotide sequence recognized and excised by a fungal tRNA splicing endonuclease may be utilized as a substrate for a fungal tRNA splicing endonuclease in a FRET assay described herein. For example, a nucleotide sequence comprising a bulge-helix-bulge structure or a mature domain of a precursor tRNA may be utilized as a substrate for a fungal tRNA splicing endonuclease in a FRET assay described herein. A nucleotide sequence recognized and excised by a fungal tRNA splicing endonuclease may comprise 10 nucleotides, 15 nucleotides, 20 nucleotides, 25 nucleotides, 25 nucleotides, 30 nucleotides, 40 nucleotides, 45 nucleotides, 50 nucleotides, 55 nucleotides, 60 nucleotides, 65 nucleotides, 75 nucleotides, 100 nucleotides, 125 nucleotides, 150 nucleotides, or more. In a specific embodiment, the substrates for a tRNA splicing endonuclease utilized in the FRET assays described herein comprise a tRNA intron. The intron may have a bulge-helix-bulge conformation. In a preferred embodiment, the nucleotide sequence comprises a mature domain of a precursor tRNA that contains an intron.

In a specific embodiment, the hybridized tRNA substrate or circularly permuted tRNA substrate depicted in FIG. 1B and FIG. 1C, respectively, are utilized in the FRET assay. In accordance with this embodiment, the free 5' end of the intron is labeled with a fluorescent donor moiety and the free 3' end is labeled with a fluorescent acceptor moiety, or the free 5' end of the intron is labeled with a fluorescent acceptor moiety and the free 3; end is labeled with a fluorescent donor moiety. Alternatively, in accordance with this embodiment, either the free 5' or 3' end is labeled with a fluorophore and the other end is labeled with a quencher.

In accordance with the invention, the tRNA substrate may be labeled with a single pair of fluorescent donor and acceptor compounds. The substrate can be labeled with different pairs of fluorescent donor moieties and fluorescent acceptor moieties. For example, two, three, four, five or more pairs of fluorescent donor moieties and fluorescent acceptor moieties can be used. In this situation, preferably, at least one of the pairs comprise a fluorescent acceptor moiety that has a different emission spectrum from the fluorescent acceptor moiety of at least one of the other pairs. Alternatively, when at least three pairs are used, the fluorescent acceptor moiety of the first pair, second pair and third pair have a different emission spectrum than the fluorescent acceptor moiety of the other two. Methods for labeling the substrate with a fluorescent acceptor moiety, a fluorescent donor moiety and/or quencher are well-known in the art (see, e.g., U.S. Pat. Nos. 6,472,156, 6,451,543, 6,348,322, 6,342,379, 6,323,039, 6,297,018, 6,291,201, 6,280,981, 5,843,658, and 5,439,797, the disclosures of which are incorporated by reference in their entirety). The labeled substrate can be microinjected or transfected into fungal cells (preferably, yeast) utilizing techniques well-known to one of skill in the art.

The cell-based assays can be conducted in any buffer system that provides conditions conducive to the tRNA endonuclease reaction. Such buffer systems are well known to the skilled artisan. In a specific embodiment, the buffer is the medium in which the cell culture is kept. Care should be taken that magnesium ions are present in the medium.

In certain embodiments, the assay is conducted for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day.

Optionally, an agent known to inhibit or reduce the activity of a fungal tRNA splicing ligase, such as an antibody that specifically binds to the ligase, is included in the contacting step of the FRET cell-based assays to exclude the possibility that the compound is functioning solely by inhibiting or reducing the activity of the ligase. In some embodiments, the activity of a tRNA splicing ligase is inhibited or reduced by excluding ATP from the reaction mixture. Although not intending to be bound by a particular mechanism of action, since the activity of tRNA splicing ligase is dependent on the presence of ATP, excluding ATP from the reaction effectively reduces the activity of the tRNA splicing ligase. Alternatively, the fungal cells used in the FRET cell-based assays may be deficient in fungal tRNA splicing ligase or the activity of the fungal tRNA splicing ligase in the fungal cells may be impaired.

In a specific embodiment, the invention provides a method of identifying an antifungal compound that inhibits or reduces fungal tRNA splicing endonuclease activity, said method comprising: (a) microinjecting or transfecting a substrate of a tRNA splicing endonuclease into a fungal cell, wherein the substrate is labeled at the 5' end with a fluorophore and at the 3' end with a quencher, or, alternatively, the substrate is labeled at the 5' end with a quencher and labeled at the 3' end with a fluorophore; (b) contacting the cell with a member of a library of compounds; and (c) measuring the activity of the tRNA splicing endonuclease, wherein an antifungal compound that inhibits or reduces the tRNA splicing activity is identified if a fluorescent signal is not detectable or reduced in the presence of the compound relative to the absence of the compound or the presence of an appropriate control.

In another embodiment, the invention provides a method of identifying an antifungal compound that inhibits or reduces fungal tRNA splicing endonuclease activity, said method comprising: (a) contacting a fungal cell containing a substrate of a tRNA splicing endonuclease with a member of a library of compounds, wherein the substrate is labeled at the 5' end with a fluorophore and at the 3' end with a quencher, or, alternatively, the substrate is labeled at the 5' end with a quencher and labeled at the 3' end with fluorophore; and (b) measuring the activity of the tRNA splicing endonuclease, wherein an antifungal compound that inhibits or reduces the tRNA splicing activity is identified if a fluorescent signal is not detectable or reduced in the presence of the compound relative to the absence of the compound or the presence of an appropriate control.

In another embodiment, the invention provides a method of identifying an antifungal compound that inhibits or reduces fungal tRNA splicing endonuclease activity, said method comprising: (a) microinjecting or transfecting a substrate of a tRNA splicing endonuclease into a fungal cell, wherein said substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety; (b) contacting the cell with a member of a library of compounds; and (c) measuring the activity of the tRNA splicing endonuclease, wherein an antifungal compound that inhibits or reduces tRNA splicing endonuclease activity is identified if the fluorescent emission of the fluorescent acceptor moiety at the wavelength of the fluorescent donor moiety in the presence of the compound is increased relative to the absence of the compound or the presence of an appropriate control. In another embodiment, the invention provides a method of identifying an antifungal compound that inhibits or reduces fungal tRNA splicing endonuclease activity, said method comprising: (a) contacting a fungal cell containing substrate of a tRNA splicing endonuclease with a member of a library of compounds, wherein said substrate is labeled at the 5' end with a fluorescent donor moiety and labeled at the 3' end with a fluorescent acceptor moiety, or, alternatively, the substrate is labeled at the 5' end with a fluorescent acceptor moiety, and labeled at the 3' end with a fluorescent donor moiety; and (b) measuring the activity of the tRNA splicing endonuclease, wherein an antifungal compound that inhibits or reduces tRNA splicing endonuclease activity is identified if the fluorescence emission of the fluorescent acceptor moiety at the wavelength of the fluorescent donor moiety in the presence of the compound is increased relative to the absence of the compound or the presence of an appropriate control.

Any nucleotide sequence recognized and excised by a fungal tRNA splicing endonuclease may be utilized as a substrate for a fungal tRNA splicing endonuclease in a FRET assay described herein. For example, a nucleotide sequence comprising a bulge-helix-bulge structure or a mature domain of a precursor tRNA may be utilized as a substrate for a fungal tRNA splicing endonuclease in a FRET assay described herein. A nucleotide sequence recognized and excised by a fungal tRNA splicing endonuclease may comprise 10 nucleotides, 15 nucleotides, 20 nucleotides, 25 nucleotides, 25 nucleotides, 30 nucleotides, 40 nucleotides, 45 nucleotides, 50 nucleotides, 55 nucleotides, 60 nucleotides, 65 nucleotides, 75 nucleotides, 100 nucleotides, 125 nucleotides, 150 nucleotides, or more. In a specific embodiment, the substrates for a tRNA splicing endonuclease utilized in the FRET assays described herein comprise a tRNA intron. The substrate may comprise a bulge-helix-bulge conformation. In a preferred embodiment, the substrate comprises a mature domain of tRNA precursor that contains an intron.

In accordance with the invention, the substrate can be labeled with a single pair of fluorescent donor and acceptor moieties. The substrate can be labeled with different pairs of fluorescent donor moieties and fluorescent acceptor moieties. For example, two, three, four, five or more pairs of fluorescent donor moieties and fluorescent acceptor moieties can be used. In this situation, preferably, at least one of the pairs comprise a fluorescent acceptor moiety that has a different emission spectrum from the fluorescent acceptor moiety of at least one of the other pairs. Alternatively, when at least three pairs are used, the fluorescent acceptor moiety of the first pair, second pair and third pair have a different emission spectrum than the fluorescent acceptor moiety of the other two. Methods for labeling the substrate with a fluorescent acceptor moiety, a fluorescent donor moiety and/or quencher are well-known in the art (see, e.g., U.S. Pat. Nos. 6,472,156, 6,451,543, 6,348,322, 6,342,379, 6,323,039, 6,297,018, 6,291,201, 6,280,981, 5,843,658, and 5,439,797, the disclosures of which are incorporated by reference in their entirety). The labeled substrate can be microinjected or transfected into fungal cells (preferably, mammalian cells and more preferably, human cells) utilizing techniques well-known to one of skill in the art (see, e.g., Adams et al., 1991, Nature 349:694-697).

The activity of a compound on a fungal tRNA splicing endonuclease in the FRET cell-based assays can be determined by measuring the fluorescent emission spectra of the substrate utilizing techniques well-known to one of skill in the art. The fluorescent emission spectra measured depends, in part, on the fluorophore used.

5.4.2.2 Fungal Extract Assays with a Labeled Substrate

The FRET cell-free assays may be conducted by contacting a substrate for a fungal tRNA splicing endonuclease with a fungal extract (e.g., a yeast extract) or a purified fungal tRNA splicing endonuclease and a compound, wherein the substrate is labeled at the 5' end with a fluorophore and labeled at the 3' end with a quencher, or, alternatively, the substrate is labeled at the 5' end with a quencher and labeled at the 3' end with a fluorophore; and measuring the fluorescence of the substrate by, e.g., a fluorescence emission detector such as a Viewlux or Analyst. The tRNA splicing endonuclease will cleave the substrate and result in the production of a detectable fluorescent signal. A compound that inhibits or reduces the activity of the endogenous tRNA splicing endonuclease will inhibit or reduce the cleavage of the substrate and thus, inhibit or reduce the production of a detectable fluorescent signal relative to a negative control (e.g., PBS). A compound that enhances the activity of the tRNA splicing endonuclease will enhance the cleavage of the substrate and thus, increase the production of a detectable fluorescent signal relative to a negative control (e.g., PBS).

Alternatively, the FRET cell-free assays may be conducted by contacting a substrate for a fungal tRNA splicing endonuclease with a fungal extract (e.g., a yeast extract) or a purified fungal tRNA splicing endonuclease and a compound, wherein the substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety; and measuring the fluorescence of the substrate by, e.g., a fluorescence emission detector such as a Viewlux or Analyst. The tRNA splicing endonuclease in the fungal extract will cleave the substrate and result in the production of a detectable fluorescent signal by the fluorescent donor moiety and fluorescent acceptor moiety at the wavelength of the fluorescent donor moiety. A compound that inhibits or reduces the activity of the tRNA splicing endonuclease will inhibit or reduce cleavage of the substrate and thus increase the fluorescence emission of the fluorescent acceptor moiety at the wavelength of the fluorescent donor moiety relative to a negative control (e.g., PBS). A compound that enhances the activity of the tRNA splicing endonuclease will enhance the cleavage of the substrate and thus reduce the fluorescence emission of the fluorescent acceptor moiety at the wavelength of the fluorescent donor moiety relative to a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET fungal extract assays described herein.

In accordance with the invention, the tRNA substrate may be labeled with a single pair of fluorescent donor and acceptor moieties. The substrate can be labeled with different pairs of fluorescent donor moieties and fluorescent acceptor moieties. For example, two, three, four, five or more pairs of fluorescent donor moieties and fluorescent acceptor moieties can be used. In this situation, preferably, at least one of the pairs comprise a fluorescent acceptor moiety that has a different emission spectrum from the fluorescent acceptor moiety of at least one of the other pairs. Alternatively, when at least three pairs are used, the fluorescent acceptor moiety of the first pair, second pair and third pair have a different emission spectrum than the fluorescent acceptor moiety of the other two. Methods for labeling the substrate with a fluorescent acceptor moiety, a fluorescent donor moiety and/or quencher are well-known in the art (see, e.g., U.S. Pat. Nos. 6,472,156, 6,451,543, 6,348,322, 6,342,379, 6,323,039, 6,297,018, 6,291,201, 6,280,981, 5,843,658, and 5,439,797, the disclosures of which are incorporated by reference in their entirety).

The activity of a compound on a fungal tRNA splicing endonuclease in the FRET fungal extract assays can be determined by measuring the fluorescent emission spectra of the substrate utilizing techniques well-known to one of skill in the art. The fluorescent emission spectra measured depends, in part, on the fluorophore used.

The assay can be conducted in any buffer system that provides conditions conducive to the tRNA endonuclease reaction. Such buffer systems are well known to the skilled artisan. In a specific embodiment, the buffer comprises 20 mM Tris at a pH of 7.0, 50 mM KCl, 0.1 mM DTT, 5 mM $MgCl_2$, and 0.4% Triton X100. Care should be taken that pH, salt concentration, detergent concentration, etc., of the buffer system do not interfere with FRET.

In certain embodiments, the assay is conducted for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day.

Optionally, an agent known to inhibit or reduce the activity of a fungal tRNA splicing ligase, such as an antibody that specifically binds to the ligase, is included in the contacting step of the FRET cell-free assays to exclude the possibility that the compound is functioning solely by inhibiting or reducing the activity of the ligase. In some embodiments, the activity of a tRNA splicing ligase is inhibited or reduced by excluding ATP from the reaction mixture. Although not intending to be bound by a particular mechanism of action, since the activity of tRNA splicing ligase is dependent on the presence of ATP, excluding ATP from the reaction effectively reduces the activity of the tRNA splicing ligase. Alternatively, the extracts used in the assay may be from fungal cells deficient in fungal tRNA splicing ligase or the activity of the fungal tRNA splicing ligase in the extract may be impaired.

In one embodiment, the invention provides a method of identifying an antifungal compound that inhibits or reduces fungal tRNA splicing endonuclease activity, said method comprising: (a) contacting a fungal cell-free extract (preferably, a tRNA splicing endonuclease extract) or a purified fungal tRNA splicing endonuclease with a substrate of a tRNA splicing endonuclease and a member of a library of compounds, wherein the substrate is labeled at the 5' end with a fluorophore and at the 3' end with a quencher, or, alternatively, the substrate is labeled at the 5' end with a quencher and the 3' end is labeled with a fluorophore; and (b) measuring the activity of the tRNA splicing endonuclease, wherein an antifungal compound that inhibits tRNA splicing endonuclease activity is identified if a fluorescent signal is less detectable (or not detectable) in the presence of the compound relative to the signal in the absence of the compound or the presence of a negative control. In another embodiment, the invention provides a method of identifying an antifungal compound that inhibits or reduces fungal tRNA splicing endonuclease activity, the method comprising: (a) contacting a fungal cell-free extract (preferably, a tRNA splicing endonuclease extract) or a purified fungal tRNA splicing endonuclease with a substrate of a tRNA splicing endonuclease and a member of a library of compounds, wherein said substrate is labeled at the 5' end with a fluorescent donor moiety and labeled at the 3' end with a fluorescent acceptor moiety, or, alternatively, the substrate is labeled at the 5' end with a fluorescent acceptor moiety and labeled at the 3' end with a fluorescent donor moiety; and (b) measuring the activity of the tRNA splicing endonuclease, wherein an antifungal compound that inhibits or reduces tRNA endonuclease splicing activity is identified if the fluorescent emission of the fluorescent acceptor moiety at the wavelength of the fluorescent donor moiety in the presence of the compound is increased relative to the absence of the compound or the presence of a negative control.

The activity of a compound on a fungal tRNA splicing endonuclease in the FRET cell-free assays can be determined by measuring the fluorescent emission spectra of the substrate utilizing techniques well-known to one of skill in the art. The fluorescent emission spectra measured depends, in part, on the fluorophore used.

5.4.2.3 Fungal Cell-Based Assays with Labeled Enzyme

A FRET cell-based assay may be conducted by microinjecting or transfecting a first subunit of a fungal tRNA splicing endonuclease (e.g., SEN2) labeled with a fluorophore and a second, different subunit of a fungal tRNA splicing endonuclease (e.g., SEN34) labeled with a quencher into a fungal cell and contacting the fungal cell with a compound, and measuring the fluorescence of the fungal tRNA splicing endonuclease by, e.g., a fluorescence emission detector such as a Viewlux or Analyst. Preferably, the cell microinjected or transfected is deficient in one or more of the subunits of the fungal tRNA splicing endonuclease. The formation of the fungal tRNA splicing endonuclease from the labeled subunits will result in a reduction in the detectable fluorescence. A compound that inhibits or reduces the formation of the fungal tRNA splicing endonuclease will enhance the production of detectable fluorescent signal relative to a negative control (e.g., PBS). A compound that enhances the formation of the fungal tRNA splicing endonuclease will reduce or inhibit the fluorescence detectable relative to a negative control (e.g., PBS).

Alternatively, a FRET cell-based assay may be conducted by microinjecting or transfecting a first subunit of a fungal tRNA splicing endonuclease (e.g., SEN2) labeled with a fluorescent donor moiety and a second, different subunit of a fungal tRNA splicing endonuclease (e.g., SEN34) labeled with a fluorescent acceptor moiety into a fungal cell and contacting the fungal cell with a compound, and measuring the fluorescence of the fungal tRNA splicing endonuclease by, e.g., a fluorescence emission detector such as a Viewlux or Analyst. The formation of the fungal tRNA splicing endonuclease will result in the production of a detectable fluorescent signal by the fluorescent donor moiety and fluorescent acceptor moiety at the wavelength of the fluorescent donor moiety. A compound that inhibits or reduces the formation of the fungal tRNA splicing endonuclease will reduce the fluorescence emission of the fluorescent acceptor moiety at the wavelength of the fluorescent donor moiety relative to a negative control (e.g., PBS). A compound that enhances the formation of the fungal tRNA splicing endonuclease will increase the fluorescence emission of the fluorescent acceptor moiety at the wavelength of the fluorescent donor moiety relative to a negative control (e.g., PBS). In a preferred embodiment, a negative control (e.g., PBS or another agent that is known to have no effect on the cleavage of the substrate) and a positive control (e.g., an agent that is known to have an effect on the cleavage of the substrate) are included in the FRET fungal cell-based assays described herein.

Methods for labeling a subunit of a fungal tRNA splicing endonuclease with a fluorescent acceptor moiety, a fluorescent donor moiety and/or quencher are well-known in the art (see, e.g., U.S. Pat. Nos. 6,472,156, 6,451,543, 6,348,322, 6,342,379, 6,323,039, 6,297,018, 6,291,201, 6,280,981, 5,843,658, and 5,439,797, the disclosures of which are incorporated by reference in their entirety).

5.4.2.4 Cell-Free Assays with Labeled Enzyme

A FRET assay may be conducted by contacting a first subunit of a fungal tRNA splicing endonuclease (e.g., SEN2) labeled with a fluorophore and a second subunit of a fungal tRNA splicing endonuclease (e.g., SEN34) labeled with a quencher with a compound in vitro under conditions conducive to the formation of the endonuclease, and measuring the fluorescence of the fungal tRNA splicing endonuclease by, e.g., a fluorescence emission detector such as a Viewlux or Analyst. The formation of the fungal tRNA splicing endonuclease from the labeled subunits will result in a reduction in the fluorescence detectable. A compound that inhibits or reduces the formation of the fungal tRNA splicing endonuclease will enhance the production of detectable fluorescent signal relative to a negative control (e.g., PBS). A compound that enhances the formation of the fungal tRNA splicing endonuclease will reduce or inhibit the fluorescence detectable relative to a negative control (e.g., PBS).

Alternatively, a FRET fungal assay may be conducted by contacting a first subunit of a fungal tRNA splicing endonuclease (e.g., SEN2) labeled with a fluorescent donor moiety and a second, different subunit of a fungal tRNA splicing endonuclease (e.g., SEN34) labeled with a fluorescent acceptor moiety with a compound in vitro under conditions conducive to the formation of the endonuclease, and measuring the fluorescence of the fungal tRNA splicing endonuclease by, e.g., a fluorescence emission detector such as a Viewlux or Analyst. The formation of the fungal tRNA splicing endonuclease will result in the production of a detectable fluorescent signal by the fluorescent donor moiety and fluorescent acceptor moiety at the wavelength of the fluorescent donor moiety. A compound that inhibits or reduces the formation of the fungal tRNA splicing endonuclease will reduce the fluorescence emission of the fluorescent acceptor moiety at the wavelength of the fluorescent donor moiety relative to a negative control (e.g., PBS). A compound that enhances the formation of the fungal tRNA splicing endonuclease will increase the fluorescence emission of the fluorescent acceptor moiety at the wavelength of the fluorescent donor moiety relative to a negative control (e.g., PBS). In a preferred embodiment, a negative control (e.g., PBS or another agent that is known to have no effect on the cleavage of the substrate) and a positive control (e.g. an agent that is known to have an effect on the cleavage of the substrate) are included in the FRET fungal assays described herein.

5.4.3 Direct Binding Assays

Compounds that modulate the activity of a fungal tRNA splicing endonuclease can be identified by direct binding assays. In particular, compounds that inhibit the activity of a fungal tRNA splicing endonuclease by directly or indirectly reducing or inhibiting the interaction between a substrate for a fungal tRNA splicing endonuclease and a fungal tRNA splicing endonuclease. Such assays are described in International Patent Publication Nos. WO 02/083837 and WO 02/083953, the disclosures of which are hereby incorporated by reference in their entireties. Briefly, direct binding assays may be conducted by attaching a library of compounds to solid supports, e.g., polymer beads, with each solid support having substantially one type of compound attached to its surface. The plurality of solid supports of the library is exposed in aqueous solution to a substrate for a fungal tRNA splicing endonuclease having a detectable label, forming a dye-labeled substrate:support-attached compound complex. Binding of a substrate to a particular compound labels the solid support, e.g., bead, comprising the compound, which can be physically separated from other, unlabeled solid supports. Once labeled solid supports are identified, the chemical structures of the compounds thereon can be determined by, e.g., reading a code on the solid support that correlates with the structure of the attached compound.

Alternatively, direct binding assays may be conducted by contacting a substrate for a fungal tRNA splicing endonuclease having a detectable label with a member of a library of compounds free in solution, in labeled tubes or microtiter wells, or a microarray. Compounds in the library that bind to the labeled substrate of a fungal tRNA splicing endonuclease will form a detectably labeled complex that can be identified and removed from the uncomplexed, unlabeled compounds in the library, and from uncomplexed, labeled substrate of a fungal tRNA splicing endonuclease, by a variety of methods including, but not limited to, methods that differentiate changes in the electrophoretic, chromatographic, or thermostable properties of the complexed substrate.

5.4.4 Fluorescence Polarization Assay

The effect of a compound on the activity of a fungal tRNA splicing endonuclease may be determined utilizing a fluorescence polarization-based assay. In such an assay, a fluorescently labeled substrate for a fungal tRNA splicing endonuclease is contacted with a fungal cell-free extract (preferably, a fungal tRNA splicing endonuclease extract) or a purified fungal tRNA splicing endonuclease and a compound or a member of a library of compounds; and the fluorescently polarized light emitted is measured. An important aspect of this assay is that the size of the substrate used in the assay is large enough to distinguish a change in fluorescent polarized light emitted following cleavage of the substrate. The fungal tRNA splicing endonuclease in the cell-free extract or the purified fungal tRNA splicing endonuclease will cleave the substrate and result in a change in intensity of emitted polarized light. Fluorescently labeled substrates when excited with plane polarized light will emit light in a fixed plane only if they do not rotate during the period between excitation and emission. The extent of depolarization of the emitted light depends upon the amount of rotation of the substrate, which is dependent on the size of the substrate. Small substrates rotate more than larger substrates between the time they are excited and the time they emit fluorescent light. A small fluorescently labeled substrate rotates rapidly and the emitted light is depolarized. A large fluorescently labeled substrate rotates more slowly and results in the emitted light remaining polarized. A compound that inhibits or reduces the activity of the fungal tRNA splicing endonuclease will inhibit or reduce the cleavage of the substrate and thus, decrease the rotation of the substrate relative to a negative control (e.g., PBS), which will result in the emitted light remaining polarized. A compound that enhances the activity of the fungal tRNA splicing endonuclease will enhance the cleavage of the substrate and thus, increase the rotation of the substrate relative to a negative control (e.g., PBS), which will result in more of the emitted light being depolarized.

The light intensities are measured in planes 90° apart and are conventionally designated the horizontal and vertical intensities. In some instruments the excitation filter is moveable while the emission filter is fixed. In certain other machines the horizontal and vertical intensities are measured simultaneously via fiber optics. Research grade fluorescence polarization instruments are commercially available from, e.g., PanVera, BMG Lab Technologies, and LJL Biosystems. Abbott provides clinical laboratory instrumentation. The value of fluorescence polarization is determined by the following equation:

$$polarization = \frac{intensity_{vertical} - intensity_{horizontal}}{intensity_{vertical} + intensity_{horizontal}}$$

Fluorescence polarization values are most often divided by 1000 and expressed as millipolarization units (mP).

5.4.5 tRNA Endonuclease Suppression Assay

The effect of a compound or a member of a library of compounds on the activity of a fungal tRNA splicing endonuclease may be determined using a tRNA endonuclease suppression assay. In such an assay, a host cell is engineered to contain a first reporter gene construct and a suppressor tRNA; the expression of the suppressor tRNA is induced; the host cell is contacted with a compound or a member of a library of compounds; and the expression of the reporter gene and/or the activity of the protein encoded by the reporter gene is measured. The first reporter gene construct comprises a reporter gene with a nonsense codon in its open reading frame such that the open reading frame is interrupted. Standard mutagenesis techniques as described, e.g., in Sambrook (Sambrook, 1989, Molecular Cloning, A Laboratory Manual, Second Edition; DNA Cloning, Volumes I and II (Glover, Ed. 1985)) may be used to introduce a nonsense codon into the open reading frame of any reporter gene well-known to one of skill in the art. The first reporter gene construct is transfected into a host cell engineered to contain a suppressor tRNA. Alternatively, the first reporter gene is cotransfected into a host cell with a suppressor tRNA. The suppressor tRNA's expression is regulated by a controllable regulatory element; such as by a tetracycline regulated regulatory element (see, e.g., Buvoli et al., 2000, Molecular and Cellular Biology 20:3116-3124; Park and RajBhandary, 1998, Molecular and Cellular Biology 18:4418-4425) and the suppressor tRNA contains a tRNA intron in the anticodon stem such that only properly spliced suppressor tRNA is functional. Expression of functional suppressor tRNA is dependent on (i) the transcription of the suppressor tRNA, and (ii) tRNA splicing. The expression of functional suppressor tRNA suppresses the nonsense codon in the reporter gene and results in full length, functional reporter gene expression. Accordingly, the expression of full length, functional reporter gene correlates with the expression of functional suppressor tRNA, which in turn correlates with the level of transcription of the suppressor TRNA and tRNA splicing. The expression of full-length reporter gene and the activity of the protein encoded by the reporter gene can be assayed by any method well known to the skilled artisan or as described herein.

A compound that inhibits or reduces the activity of a fungal tRNA splicing endonuclease will inhibit or reduce the production of functional suppressor tRNA and thus, reduce the expression of the reporter gene relative to a previously determined reference range or an appropriate control (e.g., a negative control, such as PBS). A compound that enhances the activity of a fungal tRNA splicing endonuclease will enhance the production of functional suppressor tRNA and thus, enhance the production of the reporter gene relative to a previously determined reference range or an appropriate control (e.g., a negative control, such as PBS).

The step of inducing the expression of the suppressor tRNA may be conducted simultaneously with the step of contacting the host cell with a compound or at least 5 minutes, at least 15 minutes, at least 0.5 hours, at least 1 hour, at least 1.5 hours, at least 2 hours, at least 3 hours, at least 4 hours, at least 5 hours, at least 6 hours, at least 8 hours, at least 10 hours or at least 12 hours before the step of contacting the compound with the host cell. In certain embodiments, the expression of the suppressor tRNA is induced by incubating the host cell with an agent such as, e.g., tetracycline, for approximately 5 minutes, approximately 15 minutes, approximately 0.5 hours, approximately 1 hour, approximately 1.5 hours, approximately 2 hours, approximately 3 hours, approximately 4 hours, approximately 5 hours, approximately 6 hours, approximately 8 hours, approximately 10 hours or approximately 12 hours. In other embodiments, the host cell is contacted with the compound for approximately 5 minutes, approximately 15 minutes, approximately 0.5 hours, approximately 1 hour, approximately 1.5 hours, approximately 2 hours, approximately 3 hours, approximately 4 hours, approximately 5 hours, 6 approximately hours, 8 approximately hours, approximately 10 hours or approximately 12 hours.

Optionally, the host cell is engineered to contain a second reporter gene construct comprising a reporter gene different from the first reporter gene that does not contain a nonsense codon. In a specific embodiment, the reporter genes used in the tRNA endonuclease suppression assay are Red and Green Click Beetle luciferase, wherein the Red luciferase contains the nonsense codon. A host cell may be engineered to stably express the two luciferase genes and the suppressor tRNA whose expression is regulated by a controlled regulatory element (such as a tetracycline-controlled regulatory element). In the absence of an agent such as tetracycline, the suppressor tRNA is not expressed and thus the red-to-green ratio is low. In the presence of an agent such as tetracycline, the suppressor tRNA is expressed and thus the red-to-green ratio increases. For a high-throughput screening, cells are plated in the presence of a compound. After a certain time period, media containing an agent, such as tetracycline, are added to induce suppressor tRNA expression.

Compounds that inhibit or reduce the activity of fungal tRNA splicing endonuclease will decrease the red-to-green ration compared to a control without the compound. Once compounds are identified in this assay that modulate the activity of fungal tRNA splicing endonuclease, they may be tested using one or more of the assays described above to confirm their activity.

5.4.6 FISH Assay

The activity of a fungal tRNA splicing endonuclease may be determined in an assay in which the persistence and quantity of tRNA intron is detected in a fungal cell. The amount of tRNA intron is quantified at different time points after or during the incubation of the cell with the compound. The tRNA intron can be detected by means of fluorescence in situ hybridization (FISH) using a tRNA intron-specific probe. In certain embodiments, a control experiment is conducted in parallel wherein the fungal cell is not contacted with a compound.

In the absence of an inhibitor of a fungal tRNA splicing endonuclease, the splicing reaction is fast and the concentration of intron in the cell is low. Without being bound by theory, because the spliced intron is normally degraded the concentration of tRNA intron in the fungal cell is below the detection threshold. In the presence of an inhibitor of fungal tRNA splicing endonuclease, the splicing reaction is slowed down and the amount of tRNA intron increases. Thus, a compound that inhibits or reduces fungal tRNA splicing endonuclease can be identified by its ability to increase the level of tRNA intron in the fungal cell.

Methods for conducting FISH are well-known to the skilled artisan and can be used with the invention. Exemplary methods for FISH are described in Sarkar and Hopper, 1998 (Mol. Biol. Cell 9:3041-3055), which is incorporated herein in its entirety.

In certain embodiments, a FISH assay is used to determine the effect of a compound on the activity of a fungal tRNA splicing endonuclease in a high-throughput screen. In particular a 96-lens microscope can be used for a high-throughput screen based on FISH. In a specific embodiment, 96 cell cultures are incubated in a 96-well plate with different compounds. Subsequently, the cells are subjected to a FISH analysis using a tRNA intron specific probe and analyzed using the 96-lens microscope. The presence of a signal or the presence of a significantly stronger signal demonstrates that tRNA intron was present in the cells at elevated levels and thus the compound is a candidate inhibitor of tRNA splicing endonuclease.

Without being bound by a particular theory, the FISH assay identifies the compound as inhibitor of the tRNA splicing endonuclease directly. Thus, in certain embodiments, a compound that was identified in a FISH assay as an inhibitor of tRNA splicing is a prima facie candidate for an inhibitor of tRNA splicing endonuclease.

5.4.7 Other Screening Assays

The activity of a fungal tRNA splicing endonuclease may be determined in an assay in which the amount of substrate for a tRNA splicing endonuclease cleaved by the endonuclease in the presence of a compound relative to a control (preferably, a negative control and more preferably, a negative control and a positive control) is detected. Such an assay may be conducted by contacting or incubating a compound with a labeled substrate for a fungal tRNA splicing endonuclease and a fungal cell-free extract or purified fungal tRNA splicing endonuclease under conditions conducive for tRNA splicing endonuclease activity, and measuring the amount of cleaved substrate. The substrate for the fungal tRNA splicing endonuclease can be labeled with any detectable agent. Useful labels in the present invention can include, but are not limited to, spectroscopic labels such as fluorescent dyes (e.g., fluorescein and derivatives such as fluorescein isothiocyanate (FITC) and Oregon Green™), rhodamine and derivatives (e.g., Texas red, tetramethylrhodimine isothiocynate (TRITC), bora-3a,4a-diaza-s-indacene (BODIPY®) and derivatives), digoxigenin, biotin, phycoerythrin, AMCA, CyDye™, and the like, radiolabels (e.g., $^3$H, $^{125}$I, $^{35}$S, $^{14}$C, $^{32}$P, $^{33}$P), enzymes (e.g., horseradish peroxidase, alkaline phosphatase), spectroscopic colorimetric labels such as colloidal gold or colored glass or plastic (e.g., polystyrene, polypropylene, latex) beads, or nanoparticles—nanoclusters of inorganic ions with defined dimension from 0.1 to 1000 nm) utilizing techniques known to one of skill in the art. In certain embodiments, a compound is contacted or incubated with a labeled substrate for a fungal tRNA splicing endonuclease and a fungal cell-free extract or purified fungal tRNA splicing endonuclease for at least 5 minutes, at least 10 minutes, at least 15 minutes, at least 30 minutes, at least 1 hour, at least 2 hours, or more. The amount of cleaved substrate is proportional to the activity of the tRNA splicing endonuclease. The amount of cleaved tRNA splicing endonuclease can be measured by any technique known to one skilled in the art.

In certain embodiments, the cleaved tRNA splicing endonuclease substrate is separated from the uncleaved tRNA splicing endonuclease substrate by gel-electrophoresis. The amount of cleaved tRNA splicing endonuclease substrate can be quantified by measuring the intensity of the signal of the cleaved tRNA splicing endonuclease substrate. The stronger the signal produced by the cleaved tRNA splicing endonuclease substrate relative to the uncleaved tRNA splicing endonuclease substrate the more active is the tRNA splicing endonuclease. The signal intensity can be quantified using autoradiography or a phosphoimager. If the activity of the tRNA splicing endonuclease is decreased in the presence of a compound, i.e., if the signal of the cleaved tRNA splicing endonuclease substrate relative to the uncleaved tRNA splicing endonuclease substrate is decreased compared to the reaction without the compound or in the presence of a negative control, the compound is identified as an inhibitor of the tRNA splicing endonuclease.

In other embodiments, the amount of cleaved tRNA is determined using mass spectrometry.

5.5 Characterization of the Structure of Compounds

If the library comprises arrays or microarrays of compounds, wherein each compound has an address or identifier, the compound can be deconvoluted, e.g., by cross-referencing the positive sample to original compound list that was applied to the individual test assays.

If the library is a peptide or nucleic acid library, the sequence of the compound can be determined by direct sequencing of the peptide or nucleic acid. Such methods are well known to one of skill in the art.

A number of physico-chemical techniques can be used for the de novo characterization of compounds bound to the target RNA. Examples of such techniques include, but are not limited to, mass spectrometry, NMR spectroscopy, X-ray crytallography and vibrational spectroscopy.

5.5.1 Mass Spectrometry

Mass spectrometry (e.g., electrospray ionization ("ESI"), matrix-assisted laser desorption-ionization ("MALDI"), and Fourier-transform ion cyclotron resonance ("FT-ICR") can be used for elucidating the structure of a compound.

MALDI uses a pulsed laser for desorption of the ions and a time-of-flight analyzer, and has been used for the detection of noncovalent tRNA:amino-acyl-tRNA synthetase complexes (Gruic-Sovulj et al., 1997, J. Biol. Chem. 272:32084-32091). However, covalent cross-linking between the target nucleic acid and the compound is required for detection, since a non-covalently bound complex may dissociate during the MALDI process.

ESI mass spectrometry ("ESI-MS") has been of greater utility for studying non-covalent molecular interactions because, unlike the MALDI process, ESI-MS generates molecular ions with little to no fragmentation (Xavier et al., 2000, Trends Biotechnol. 18(8):349-356). ESI-MS has been used to study the complexes formed by HIV Tat peptide and protein with the TAR RNA (Sannes-Lowery et al, 1997, Anal. Chem. 69:5130-5135).

Fourier-transform ion cyclotron resonance ("FT-ICR") mass spectrometry provides high-resolution spectra, isotope-resolved precursor ion selection, and accurate mass assignments (Xavier et al., 2000, Trends Biotechnol. 18(8):349-356). FT-ICR has been used to study the interaction of aminoglycoside antibiotics with cognate and non-cognate RNAs (Hofstadler et al, 1999, Anal. Chem. 71:3436-3440; and Griffey et al., 1999, Proc. Natl. Acad. Sci. USA 96:10129-10133). As true for all of the mass spectrometry methods discussed herein, FT-ICR does not require labeling a compound.

An advantage of mass spectroscopy is not only the elucidation of the structure of the compound, but also the determination of the structure of the compound bound to an RNA. Such information can enable the discovery of a consensus structure of a compound that specifically binds to an RNA.

5.5.2. NMR Spectroscopy

NMR spectroscopy is a valuable technique for identifying complexed target nucleic acids by qualitatively determining changes in chemical shift, specifically from distances measured using relaxation effects, and NMR-based approaches have been used in the identification of small molecule binders of protein drug targets (Xavier et al., 2000, Trends Biotechnol. 18(8):349-356). The determination of structure-activity relationships ("SAR") by NMR is the first method for NMR described in which small molecules that bind adjacent subsites are identified by two-dimensional 1H-15N spectra of the target protein (Shuker et al., 1996, Science 274:1531-1534). The signal from the bound molecule is monitored by employing line broadening, transferred NOEs and pulsed field gradient diffusion measurements (Moore, 1999, Curr. Opin. Biotechnol. 10:54-58). A strategy for lead generation by NMR using a library of small molecules has been recently described (Fejzo et al., 1999, Chem. Biol. 6:755-769).

SAR by NMR can be used to elucidate the structure of a compound.

As described above, NMR spectroscopy is a technique for identifying binding sites in target nucleic acids by qualitatively determining changes in chemical shift, specifically from distances measured using relaxation effects. Examples of NMR that can be used for the invention include, but are not limited to, one-dimensional NMR, two-dimensional NMR, correlation spectroscopy ("COSY"), and nuclear Overhauser effect ("NOE") spectroscopy. Such methods of structure determination of compounds are well-known to one of skill in the art.

Similar to mass spectroscopy, an advantage of NMR is the not only the elucidation of the structure of the compound, but also the determination of the structure of the compound bound to the RNA. Such information can enable the discovery of a consensus structure of a compound that specifically binds to an RNA.

5.5.3 X-ray Crystallography

X-ray crystallography can be used to elucidate the structure of a compound. For a review of x-ray crystallography see, e.g., Blundell et al. 2002, Nat Rev Drug Discov 1(1):45-54. The first step in x-ray crystallography is the formation of crystals. The formation of crystals begins with the preparation of highly purified and soluble samples. The conditions for crystallization is then determined by optimizing several solution variables known to induce nucleation, such as pH, ionic strength, temperature, and specific concentrations of organic additives, salts and detergent. Techniques for automating the crystallization process have been developed to automate the production of high-quality protein crystals. Once crystals have been formed, the crystals are harvested and prepared for data collection. The crystals are then analyzed by diffraction (such as multi-circle diffractometers, high-speed CCD detectors, and detector off-set). Generally, multiple crystals must be screened for structure determinations.

5.5.4 Vibrational Spectroscopy

Vibrational spectroscopy (e.g., infrared (IR) spectroscopy or Raman spectroscopy) can be used for elucidating the structure of a compound.

Infrared spectroscopy measures the frequencies of infrared light (wavelengths from 100 to 10,000 nm) absorbed by the compound as a result of excitation of vibrational modes according to quantum mechanical selection rules which require that absorption of light cause a change in the electric dipole moment of the molecule. The infrared spectrum of any molecule is a unique pattern of absorption wavelengths of varying intensity that can be considered as a molecular fingerprint to identify any compound.

Infrared spectra can be measured in a scanning mode by measuring the absorption of individual frequencies of light, produced by a grating which separates frequencies from a mixed-frequency infrared light source, by the compound relative to a standard intensity (double-beam instrument) or pre-measured ("blank") intensity (single-beam instrument). In a preferred embodiment, infrared spectra are measured in a pulsed mode ("FT-IR") where a mixed beam, produced by an interferometer, of all infrared light frequencies is passed through or reflected off the compound. The resulting interferogram, which may or may not be added with the resulting interferograms from subsequent pulses to increase the signal strength while averaging random noise in the electronic signal, is mathematically transformed into a spectrum using Fourier Transform or Fast Fourier Transform algorithms.

Raman spectroscopy measures the difference in frequency due to absorption of infrared frequencies of scattered visible or ultraviolet light relative to the incident beam. The incident monochromatic light beam, usually a single laser frequency, is not truly absorbed by the compound but interacts with the electric field transiently. Most of the light scattered off the sample will be unchanged (Rayleigh scattering) but a portion of the scatter light will have frequencies that are the sum or difference of the incident and molecular vibrational frequencies. The selection rules for Raman (inelastic) scattering require a change in polarizability of the molecule. While some vibrational transitions are observable in both infrared and Raman spectrometry, must are observable only with one or the other technique. The Raman spectrum of any molecule is a unique pattern of absorption wavelengths of varying intensity that can be considered as a molecular fingerprint to identify any compound.

Raman spectra are measured by submitting monochromatic light to the sample, either passed through or preferably reflected off, filtering the Rayleigh scattered light, and detecting the frequency of the Raman scattered light. An improved Raman spectrometer is described in U.S. Pat. No. 5,786,893 to Fink et al., which is hereby incorporated by reference.

Vibrational microscopy can be measured in a spatially resolved fashion to address single beads by integration of a visible microscope and spectrometer. A microscopic infrared spectrometer is described in U.S. Pat. No. 5,581,085 to Reffner et al., which is hereby incorporated by reference in its entirety. An instrument that simultaneously performs a microscopic infrared and microscopic Raman analysis on a sample is described in U.S. Pat. No. 5,841,139 to Sostek et al., which is hereby incorporated by reference in its entirety.

In one embodiment of the method, compounds are synthesized on polystyrene beads doped with chemically modified styrene monomers such that each resulting bead has a characteristic pattern of absorption lines in the vibrational (IR or Raman) spectrum, by methods including but not limited to those described by Fenniri et al., 2000, J. Am. Chem. Soc. 123:8151-8152. Using methods of split-pool synthesis familiar to one of skill in the art, the library of compounds is prepared so that the spectroscopic pattern of the bead identifies one of the components of the compound on the bead. Beads that have been separated according to their ability to bind target RNA can be identified by their vibrational spectrum. In one embodiment of the method, appropriate sorting and binning of the beads during synthesis then allows identification of one or more further components of the compound on any one bead. In another embodiment of the method, partial identification of the compound on a bead is possible through use of the spectroscopic pattern of the bead with or without the aid of further sorting during synthesis, followed by partial resynthesis of the possible compounds aided by doped beads and appropriate sorting during synthesis.

In another embodiment, the IR or Raman spectra of compounds are examined while the compound is still on a bead, preferably, or after cleavage from a bead, using methods including but not limited to photochemical, acid, or heat treatment. The compound can be identified by comparison of the IR or Raman spectral pattern to spectra previously acquired for each compound in the combinatorial library.

5.6 Secondary Assays

The compounds identified in the assays described supra that modulate the activity of a fungal tRNA splicing endonuclease (for convenience referred to herein as a "lead" compound) can be further tested for both direct binding to RNA and biological activity. In one embodiment, the compounds are tested for biological activity in further assays and/or animal models. In another embodiment, the lead compound is used to design congeners or analogs. In another embodiment, the lead compound is used to assess the effect on animalia tRNA splicing endonuclease and animalia cell proliferation. In yet another embodiment, mutagenesis studies can be conducted to assess the mechanism by which a lead compound is modulating the activity of a fungal tRNA splicing endonuclease.

5.6.1 Phenotypic or Physiological Readout

The compounds identified in the assays described supra (for convenience referred to herein as a "lead" compounds) can be tested for biological activity using host cells containing or engineered to contain a fungal tRNA splicing endonuclease coupled to a functional readout system. For example, a phenotypic or physiological readout can be used to assess activity of a fungal tRNA splicing endonuclease in the presence and absence of the lead compound.

The anti-fungal effect of a lead compound can be further assessed using numerous techniques well-known to one of skill in the art. The invention encompasses methods of anti-fungal susceptibility testing as recommended by the National Committee for Clinical Laboratories (NCCLS) (See National Committee for Clinical Laboratories Standards., 1995, Proposed Standard M27T, Villanova, Pa., all of which is incorporated herein by reference in its entirety) and other methods known to those skilled in the art (Pfaller et al., 1993, Infectious Dis. Clin. N. Am. 7: 435-444) The invention encompasses determining anti-fungal activities of the lead compounds of the invention using macrodilution methods and/or microdilution methods using protocols known to those skilled in the art (See Clancy et al., 1997, J. Clinical Microbiology, 35(11): 2878-2882; Ryder et al., 1998, Antimicrobial Agents and Chemotherapy, 42(5): 1057-1061; U.S. Pat. No. 5,521,153; U.S. Pat. No. 5,883,120, U.S. Pat. No. 5,521, 169, all of which are incorporated by reference in their entireties). Briefly, a fungal strain is cultured in an appropriate liquid media, and grown at an appropriate temperature, depending on the particular fungal strain used, for a determined amount of time, which also depends on the particular fungal strain used. An innoculum is then prepared photometrically and the turbidity of the suspension is matched to that of a standard, e.g., a McFarland standard. The effect of the lead compound on the turbidity of the inoculum is determined visually or spectrophotometrically. The minimal inhibitory concentration of the lead compound (MIC) is determined, which is defined as the lowest concentration of the lead compound which prevents visible growth of an inoculum as measured by determining the culture turbidity.

The invention also encompasses colorimetric based assays for determining the anti-fungal activity of the lead compounds of the invention. One exemplary calorimetric assay for use in the methods of the invention is described by Pfaller et al., 1994, J Clinical Microbiology, 32(8):1993-1996, which is incorporated herein by reference in its entirety; also see Tiballi et al., 1995, J Clinical Microbiology, 33(4): 915-917). This assay employs a colorimetric endpoint using an oxidation-reduction indicator (Alamar Biosciences, Inc., Sacramento Calif.).

The invention encompasses photometric assays for determining the anti-fungal activity of the lead compounds of the invention using previously described methodology (See Clancy et al., 1997, J Clinical Microbiology, 35(11): 2878-2882; Jahn et al., 1995, J Clinical Microbiology, 33(3): 661-667, each of which is incorporated herein by reference in its entirety). This photometric assay is based on quantifying mitochondrial respiration by viable fungi through the reduction of 3-(4,5-dimethyl-2thiazolyl)-2,5,-diphenyl-2H-tetrazolium bromide (MTT) to formazan. MIC's: determined by this assay are defined as the highest concentration of the lead compound associated with the first precipitous drop in optical density. In some embodiments, the compounds of the invention are assayed for anti-fungal activity using macrodilution, microdilution and MTT assays in parallel.

The antifungal properties of the lead compounds of the present invention may be determined from a fungal lysis assay, as well as by other methods, including, inter alia, growth inhibition assays, fluorescence-based fungal viability assays, flow cytometry analyses, and other standard assays known to those skilled in the art. The fungi tested in accordance with the invention include, but are not limited to fungi in the genus *Blastomyces*, including *Blastomyces dermatitidis; Paracoccidiodes*, including *Paracoccidioides brasiliensis; Sporothrix*, including *Sporothrix schenckii; Cryptococcus; Candida*, including *Candida albicans, Candida tropicalis* and *Candida glabrala; Aspergillus*, including *Aspergillus fumigarus* and *Aspergillus flavus; Histoplasma*, including *Histoplasma capsulatum; Cryptococcus*, including *Cryptococcus neoformans; Bipolaris; Cladophialophora; Cladosporium; Drechslera; Exophiala; Fonsecaea; Phialophora; Xylohypha; Ochroconis; Rhinocladiella; Scolecobasidium*; and *Wangiella*.

5.6.2 Specificity Assays

Various assays, using animalia cells, animalia cell extracts, and animalia tRNA splicing endonuclease can be conducted to determine the specificity of a lead compound for a fungal tRNA splicing endonuclease. Any of the assays described above with respect to fungal tRNA splicing endonuclease can be used to assess the effect of a compound on animalia tRNA splicing endonuclease (preferably, mammalian tRNA splicing endonuclease and, more preferably, human tRNA splicing endonuclease). Compounds that affect both animalia tRNA splicing endonuclease and fungal tRNA splicing endonuclease are not preferred for use to treat, prevent, manage or ameliorate a fungal infection or one or more symptoms thereof. Rather, such compounds may be better indicated for use to treat, prevent, manage or ameliorate proliferative disorders, such as cancer and psoriasis.

Further, assays to detect the effect of a lead compound on animalia cells can be conducted to assess utility of the compound as an antifungal agent. Many assays well-known in the art can be used to assess the survival and/or growth of an animalia cell or cell line following exposure to a lead compound; for example, cell proliferation can be assayed by measuring Bromodeoxyuridine (BrdU) incorporation (see, e.g., Hoshino et al., 1986, Int. J. Fungal infection 38, 369; Campana et al., 1988, J. Immunol. Meth. 107:79) or ($^3$H)-thymidine incorporation (see, e.g., Chen, J., 1996, Oncogene 13:1395-403; Jeoung, J., 1995, J. Biol. Chem. 270:18367-73), by direct cell count, by detecting changes in transcription, translation or activity of known genes such as proto-oncogenes (e.g., fos, nyc) or cell cycle markers (Rb, cdc2, cyclin A, D1, D2, D3, E, etc). The levels of such protein and mRNA and activity can be determined by any method well known in the art. For example, protein can be quantified by known immunodiagnostic methods such as Western blotting or immunoprecipitation using commercially available antibodies. mRNA can be quantified using methods that are well known and routine in the art, for example, using northern analysis, RNase protection, the polymerase chain reaction in connection with the reverse transcription. Cell viability can be assessed by using trypan-blue staining or other cell death or viability markers known in the art. In a specific embodiment, the level of cellular ATP is measured to determined cell viability. Differentiation can be assessed, for example, visually, based on changes in morphology.

5.6.3 Animal Models

The lead compounds identified in the assays described herein can be tested for biological activity using animal models for a fungal infection. Such animal model systems include, but are not limited to, rats, mice, chicken, cows, monkeys, pigs, dogs, rabbits, etc. In a specific embodiment of the invention, a compound identified in accordance with the methods of the invention is tested in a mouse model system. Such model systems are widely used and well-known to the skilled artisan, such as the SCID mouse model or transgenic mice.

Animal models for fungal infections, such as *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pnuemocystis carinii* pneumonia, cryptococcal meningitis, coccidioidal meningoencephalitis and cerebrospinal vasculitis, *Aspergillus niger* infection, *Fusarium* keratitis, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis have been developed (see, e.g., Arendrup et al., 2002, Infection 30(5):286-291; Kamie, 2001, Mycopathologia 152(1):5-13; Guhad et al., 200, FEMS Microbiol Lett. 192(1):27-31; Yamagata et al., 200, J Clin Microbiol. 38(9):32606; Andrutis et al., 2000, J Clin Microbiol. 38(6):2317-2323; Cock et al., 2000, Rev Inst Med Trop Sao Paulo-42(2):59-66; Shibuya et al, 1999, Microb Pathog. 27(3):123-131; Beers et al., 1999, J Lab Clin Med. 133(5):423-433; Najvar et al., 1999, Antimicrob Agents Chemother. 43(2):413-414; Williams et al., 1988, J Infect Dis. 178(4):1217-1221; Yoshida, 1988, Kansenshogaku Zasshi 72(6):621-630; Alexandrakis et al., 1998, Br J Ophthalmol. 82(3):306-311; Chakrabarti et al., 1997, J Med Vet Mycol. 35(4):295-297; Martin et al., 1997, Antimicrob Agents Chemother. 41(1):13-16; Chu et al., 1996, Avian Dis. 40(3):715-719; Fidel et al., 1996, J Infect Dis. 173(2):425-431; Cole et al., 1995, FEMS Microbiol Lett. 15; 126(2):177-180; Pollock et al., 1995, Nat Genet. 9(2):202-209; Uchida et al., 1994, Jpn J Antibiot. 47(10):1407-1412; Maebashi et al., 1994, J Med Vet Mycol. 32(5):349-359; Jensen & Schonheyder, 1993, J Exp Anim Sci. 35(4):155-160; Goksalan & Anaissie, 1992, Infect Immun. 60(8):3339-3344; Kurup et al., 1992, J Immunol. 148(12):3783-3788; Singh et al., 1990, Mycopatholgia 112(3):127-137; Salkowski & Balish, 1990, Infect Immun. 58(10):3300-3306; Ahmad et al., 1985, Am J Kidney Dis. 7(2):153-156; Alture-Werber E, Edberg S C, 1985, Mycopathologia 89(2):69-73; Kane et al., 1981, Antimicrob Agents Chemother. 20(5):595-599; Barbee et al., 1977, Am J Pathol. 86(1):281-284; and Maestrone et al., 1973, Am J Vet Res. 34(6):833-836.

The toxicity and/or efficacy of a compound identified in accordance with the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. A compound identified in accordance with the invention that exhibits large therapeutic indices is preferred. While a compound identified in accordance with the invention that exhibits toxic side effects may be used, care should be taken to design a delivery system that targets such agents to the site of effected tissue in order to minimize potential damage to uninfected cells and, thereby, reduce side effects.

The data obtained from the cell culture assays and animal studies can be used in formulating a range of dosage of a compound identified in accordance with the invention for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography.

5.6.4 Design of Congeners or Analogs

The compounds which display the desired biological activity can be used as lead compounds for the development or design of congeners or analogs having useful pharmacological activity. For example, once a lead compound is identified, molecular modeling techniques can be used to design variants of the compound that can be more effective. Examples of molecular modeling systems are the CHARM and QUANTA programs (Polygen Corporation, Waltham, Mass.). CHARM performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen et al., 1988, Acta Pharmaceutical Fennica 97:159-166; Ripka, 1998, New Scientist 54-57; McKinaly & Rossmann, 1989, Annu. Rev. Pharmacol. Toxiciol. 29:111-122; Perry & Davies, OSAR: Quantitative Structure-Activity Relationships in Drug Design pp. 189-193 (Alan R. Liss, Inc. 1989); Lewis & Dean, 1989, Proc. R. Soc. Lond. 236:125-140 and 141-162; Askew et al., 1989, J. Am. Chem. Soc. 111:1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to any identified region. The analogs and congeners can be tested for binding to a fungal tRNA splicing endonuclease using the above-described screens for biologic activity. Alternatively, lead compounds with little or no biologic activity, as ascertained in the screen, can also be used to design analogs and congeners of the compound that have biologic activity.

5.6.5 Mutagenesis Studies

The subunit(s) of a fungal tRNA splicing endonuclease and/or the nucleotide sequence of a substrate for a fungal tRNA splicing endonuclease that are necessary for a compound identified in accordance with the methods of the invention to modulate the activity of a fungal tRNA splicing endonuclease can be determined utilizing standard mutagenesis techniques well-known to one of skill in the art. One or more mutations (e.g., deletions, additions and/or substitutions) may be introduced into a fungal tRNA splicing endonuclease subunit and the effect of the mutations on the activity of the fungal tRNA splicing endonuclease in the presence or absence of a compound can be determined using an assay described herein. In particular, one or more mutations (e.g., deletions, additions, and/or substitutions) may also be introduced into a substrate for fungal tRNA endonuclease and the effect of the mutations on the activity of the fungal tRNA splicing endonuclease in the presence or absence of a compound can be determined using an assay described herein. For example, one or more mutations (e.g., deletions, additions and/or substitutions) may be introduced into the nucleotide sequence for a tRNA intron within the open frame reading of a reporter gene and the effect on the expression of a reporter gene in a reporter gene-based assay described herein can be determined. If the mutation in the tRNA intron affects the ability of the compound to modulate the expression of the reporter gene, then the mutated sequence plays a role in the activity of the tRNA splicing endonuclease.

Standard techniques known to those of skill in the art can be used to introduce mutations in the nucleotide sequence of a fungal tRNA splicing endonuclease subunit(s) and/or the nucleotide sequence of a substrate for a fungal tRNA splicing endonuclease, including, for example, site-directed mutagenesis and PCR-mediated mutagenesis. In a specific embodiment, less than 75 nucleic acid residue substitutions, less than 50 nucleic acid residue substitutions, less than 45 nucleic acid residue substitutions, less than 40 nucleic acid residue substitutions, less than 35 nucleic acid residue substitutions, less than 30 nucleic acid residue substitutions, less than 25 nucleic acid residue substitutions, less than 20 nucleic acid residue substitutions, less than 15 nucleic acid residue substitutions, less than 10 nucleic acid residue substitutions, or less than 5 nucleic acid residue substitutions are introduced into the nucleotide sequence of a fungal tRNA splicing endonuclease subunit(s) and/or the nucleotide sequence of a substrate for a fungal tRNA splicing endonuclease.

5.7 Use of Identified Compounds to Treat/Prevent a Fungal Infection

The present invention provides methods of preventing, treating, managing or ameliorating a fungal infection or one or more symptoms thereof, said methods comprising administering to a subject in need thereof one or more compounds identified in accordance with the methods of the invention. In one embodiment, the invention provides a method of preventing, treating, managing or ameliorating a fungal infection or one or more symptoms thereof, said method comprising administering to a subject in need thereof a dose of a prophylactically or therapeutically effective amount of one or more compounds identified in accordance with the methods of the invention. In another embodiment, a compound identified in accordance with the methods of the invention is not administered to prevent, treat, manage or ameliorate a fungal infection or one or more symptoms thereof, if such compound has been used previously to prevent, treat, manage or ameliorate said fungal infection.

The invention also provides methods of preventing, treating, managing or ameliorating a fungal infection or one or more symptoms thereof, said methods comprising administering to a subject in need thereof one or more of the compounds identified utilizing the screening methods described herein, and one or more therapies (e.g., prophylactic or therapeutic agents), which therapies are currently being used, have been used or are known to be useful in the prevention, treatment, management or amelioration of a fungal infection or one or more symptoms thereof (including, but not limited to conventional antifungal agents, such as listed in Section 2.2, "Current Therapies"). The therapies comprising the combination therapies of the invention can be administered sequentially or concurrently. In a specific embodiment, the combination therapies of the invention comprise a compound identified in accordance with the methods of the invention and at least one other therapy which has the same mechanism of action. In another embodiment, the combination therapies of the invention comprise a compound identified in accordance with the methods of the invention and at least one other therapy which has a different mechanism of action than the compound. The combination therapies of the present invention improve the prophylactic or therapeutic effect of a compound of the invention by functioning together with the compound to have an additive or synergistic effect. The combination therapies of the present invention reduce the side effects associated with each therapy taken alone.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

In specific embodiment, a pharmaceutical composition comprising one or more compounds identified in a screening assay described herein is administered to a subject, preferably a human, to prevent, treat, manage or ameliorate a fungal infection or one or more symptoms thereof. In accordance with the invention, the pharmaceutical compositions may also comprise one or more prophylactic or therapeutic agents which are currently being used, have been used or are known to be useful in the prevention, treatment, management or amelioration of a fungal infection or one or more symptoms thereof A compound identified in accordance with the methods of the invention may be used as a first, second, third, fourth or fifth line therapy for a fungal infection. The invention provides methods for treating, managing or ameliorating a fungal infection, or one or more symptoms therof, in a subject refractory to conventional therapies for such infections, the methods comprising administering to said subject a dose of a prophylactically or therapeutically effective amount of a compound identified in accordance with the methods of the invention. An infection may be determined to be refractory to a therapy means when at least some significant portion of the fungal cells are not killed or their cell division arrested in response to the therapy. Such a determination can be made either in vivo or in vitro by any method known in the art for assaying the effectiveness of treatment on fungal cells, using the art-accepted meanings of "refractory" in such a context.

Examples of fungal infections that can be prevented, treated, managed or ameliorated include, but are not limited to infections such as Aspergillosis, Black piedra, Candidiasis, Chromomycosis, Cryptococcosis, Onychomycosis, or Otitis externa (otomycosis), Phaeohyphomycosis, Phycomycosis, Pityriasis versicolor, ringworm, *Tinea barbae, Tinea capitis, Tinea corporis, Tinea cruris, Tinea favosa, Tinea imbricata, Tinea manuum, Tinea nigra* (palmaris), *Tinea pedis, Tinea unguium, Torulopsosis*, Trichomycosis axillaris , White piedra; Actinomycosis, Aspergillosis, Candidiasis, Chromomycosis, Coccidioidomycosis, Cryptococcosis, Entomophthoramycosis, Geotrichosis, Histoplasmosis, Mucormycosis, Mycetoma, Nocardiosis, North American Blastomycosis, Paracoccidioidomycosis, Phaeohyphomycosis, Phycomycosis, pneumocystic pneumonia, Pythiosis, Sporotrichosis, and *Torulopsosis*.

Compounds identified in accordance with the invention to evince antifungal activity are particularly useful in immunocompromised subjects who are suceptible to fungal infections. Immunocompromised patients include, for example, those infected with HIV, those undergoing chemotherapy, transplant recipients, or cancer patients receiving immunosuppressive medications. Fungal organisms which attack immunocompromised patients are often called opportunistic fungi and include, but are not limited to, *Candida*, trichosporon, and *cryptococcus*. The antifungal compounds identified in accordance with the invention are also useful in subjects whose immune system is compromised due to therapy with broad-spectrum antibacterial agents, chemotherapeutic agents, or radiation; or those subjects who have been subject to invasive procedures and devices (e.g., surgery, implants, catheters, stents, prosthetic devices).

5.8 Compositions and Methods of Administering Compounds

Biologically active compounds identified using the methods of the invention, or pharmaceutically acceptable salts thereof, can be administered to a patient, preferably a mammal, more preferably a human, suffering from a fungal infection. In a specific embodiment, a compound or a pharmaceutically acceptable salt thereof is administered to a patient, preferably a mammal, more preferably a human, as a preventative measure against a fungal infection.

When administered to a patient, the compound or a pharmaceutically acceptable salt thereof is preferably administered as component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to administer the compound and pharmaceutically acceptable salts thereof.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of the compound or a pharmaceutically acceptable salt thereof into the bloodstream.

In specific embodiments, it may be desirable to administer the compound or a pharmaceutically acceptable salt thereof locally. This may be achieved, for example, and not by way of limitation, by local infusion during surgery, topical application, e.g. in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce the compound or a pharmaceutically acceptable salt thereof into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound and pharmaceutically acceptable salts thereof can be formulated as a suppository, with traditional binders and vehicles such as triglycerides.

In another embodiment, the compound and pharmaceutically acceptable salts thereof can be delivered in a vesicle, in particular a liposome (see Langer, 1990, Science 249:1527-1533; Treat et al., in Liposomes in the Therapy of Infectious Disease and Fungal infection, Lopez-Berestein and Fidler (eds.), Liss, New York, pp. 353-365 (1989); Lopez-Berestein, ibid., pp. 317-327; see generally ibid.).

In yet another embodiment, the compound and pharmaceutically acceptable salts thereof can be delivered in a controlled release system (see, e.g., Goodson, in Medical Applications of Controlled Release, supra, vol. 2, pp. 115-138 (1984)). Other controlled-release systems discussed in the review by Langer, 1990, Science 249:1527-1533 may be used. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of a target RNA of the compound or a pharmaceutically acceptable salt thereof, thus requiring only a fraction of the systemic dose.

Compositions comprising the compound or a pharmaceutically acceptable salt thereof ("compound compositions") can additionally comprise a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, mammals, and, more particularly, in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Compound compositions, if desired, can also contain minor amounts of wetting or emulsifying agents, or pH buffering agents.

Compound compositions can take the form of solutions, suspensions, emulsions, tablets, pills, pellets, capsules, capsules containing liquids, powders, sustained-release formulations, suppositories, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Pharmaceutical Sciences, Alfonso R. Gennaro, ed., Mack Publishing Co. Easton, Pa., 19th ed., 1995, pp. 1447 to 1676, incorporated herein by reference.

In a preferred embodiment, the compound or a pharmaceutically acceptable salt thereof is formulated in accordance with routine procedures as a pharmaceutical composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero-order delivery profile as opposed to the spiked profiles of immediate release formulations. A time-delay material, such as glycerol monostearate or glycerol stearate, may also be used. Oral compositions can include standard vehicles, such as mannitol, lactose, starch, magnesium stearate, sodium saccharine, cellulose, magnesium carbonate, and the like. Such vehicles are preferably of pharmaceutical grade. Typically, compositions for intravenous administration comprise sterile isotonic aqueous buffer. Where necessary, the compositions may also include a solubilizing agent.

In another embodiment, the compound or a pharmaceutically acceptable salt thereof can be formulated for intravenous administration. Compositions for intravenous administration may optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container, such as an ampoule or sachette, indicating the quantity of active agent. Where the compound or a pharmaceutically acceptable salt thereof is to be administered by infusion, it can be dispensed, for example, with an infusion bottle containing sterile pharmaceutical grade water or saline. Where the compound or a pharmaceutically acceptable salt thereof is administered by injection, an ampoule of sterile water for injection or saline can be provided so that the ingredients may be mixed prior to administration.

The amount of a compound or a pharmaceutically acceptable salt thereof that will be effective in the prevention, treatment, management or amelioration of a particular disease will depend on the nature of the disease, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of the practitioner and each patient's circumstances. However, suitable dosage ranges for oral administration are generally about 0.001 milligram to about 500 milligrams of a compound or a pharmaceutically acceptable salt thereof per kilogram body weight per day. In specific preferred embodiments of the invention, the oral dose is about 0.01 milligram to about 100 milligrams per kilogram body weight per day, more preferably about 0.1 milligram to about 75 milligrams per kilogram body weight per day, more preferably about 0.5 milligram to 5 milligrams per kilogram body weight per day. The dosage amounts described herein refer to total amounts administered; that is, if more than one compound is administered, or if a compound is administered with a therapeutic agent, then the preferred dosages correspond to the total amount administered. Oral compositions preferably contain about 10% to about 95% active ingredient by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. Suitable dosage ranges for intranasal administration are generally about 0.01 pg/kg body weight per day to about 1 mg/kg body weight per day. Suppositories generally contain about 0.01 milligram to about 50 milligrams of a compound of the invention per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 200 milligrams per kilogram of body weight per day. Suitable doses for topical administration are in the range of about 0.001 milligram to about 1 milligram, depending on the area of administration. Effective doses may be extrapolated from dose-response curves derived from in vitro or animal model test systems. Such animal models and systems are well known in the art.

The compound and pharmaceutically acceptable salts thereof are preferably assayed in vitro and in vivo, for the desired therapeutic or prophylactic activity, prior to use in humans. For example, in vitro assays can be used to determine whether it is preferable to administer the compound, a pharmaceutically acceptable salt thereof, and/or another therapeutic agent. Animal model systems can be used to demonstrate safety and efficacy.

Equivalents:

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for identifying a compound that modulates the ability of fungal tRNA splicing endonuclease to produce mature tRNA, the method comprising:
   (a) contacting a compound or a compound from a library of compounds of compounds with a fungal cell that contains the fungal tRNA splicing endonuclease and expresses a full-length protein encoded by the coding region of a reporter gene of a nucleic acid substrate, wherein the nucleic acid substrate comprises the coding region of a reporter gene and a tRNA intron in a mature domain of a precursor tRNA, and wherein the tRNA intron is contained within the nucleic acid substrate such that the transcribed mRNA from the coding region of the reporter gene is out of frame; and
   (b) detecting the amount of full-length protein expressed, wherein an alteration in the amount of the full-length protein expressed in the presence of the compound or the compound from the library of compounds relative to the amount of the full-length protein expressed in the absence of the compound or the compound from the library of compounds or in the presence of a negative control indicates that the compound or the compound from the library of compounds modulates the ability of fungal tRNA splicing endonuclease to produce mature tRNA.

2. The method of claim 1, wherein a decrease in the amount of the full-length protein expressed in the presence of the compound or the compound from the library of compounds relative to the amount of the full-length protein expressed in the absence of the compound or the compound from the library of compounds or the presence of a negative control indicates that the compound or the compound from the library of compounds reduces the ability of fungal tRNA splicing endonuclease to produce mature tRNA.

3. The method of claim 1, wherein an increase in the amount of the full-length protein expressed in the presence of the compound or the compound from the library of compounds relative to the amount of the full-length protein expressed in the absence of the compound or the compound from the library of compounds or the presence of a negative control indicates that the compound or the compound from the library of compounds increases the ability of fungal tRNA splicing endonuclease to produce mature tRNA.

4. The method of claim 1 or 2, wherein the coding region of the reporter gene encodes at least one or more coding regions of the reporter genes from the group consisting of firefly luciferase, renilla luciferase, click beetle luciferase, green fluorescent protein, yellow fluorescent protein, red fluorescent protein, cyan fluorescent protein, blue fluorescent protein, beta-galactosidase, beta-glucoronidase, beta-lactamase, chloramphenicol acetyltransferase, and alkaline phosphatase.

5. The method of claim 1 or 2, wherein the fungal cell is a yeast cell.

6. The method of claim 5, wherein the yeast cell is a *Saccharomyces cerevisiae* cell, a *Schizosaccharomyces pombe* cell, a *Pichia pastoris* cell, or a *Hansenula polymorpha* cell.

7. The method of claim 1 or 2, wherein the method further comprises assessing the specificity of the compound or the compound from the library of compounds for modulating fungal tRNA splicing endonuclease relative to animalia tRNA splicing endonuclease, wherein such assessment comprises contacting the compound or the compound from the library of compounds with an animalia tRNA splicing endonuclease and the substrate, and detecting the amount of substrate cleaved by the animalia tRNA splicing endonuclease, wherein the compound or the compound from the library of compounds is specific for fungal tRNA splicing endonuclease if the amount of substrate cleaved by the animalia tRNA splicing endonuclease in the presence of the compound or the compound from the library of compounds is not altered relative to the amount of substrate cleaved by the animalia tRNA splicing endonuclease in the absence of the compound or the compound from the library of compounds or the presence of a negative control.

8. The method of claim 3, wherein the method further comprises assessing the specificity of the compound or the compound from the library of compounds for modulating fungal tRNA splicing endonuclease relative to animalia tRNA splicing endonuclease, wherein such assessment comprises contacting the compound or the compound from the library of compounds with an animalia tRNA splicing endonuclease and the substrate, and detecting the amount of substrate cleaved by the animalia tRNA splicing endonuclease, wherein the compound or the compound from the library of compounds is specific for fungal tRNA splicing endonuclease if the amount of substrate cleaved by the animalia tRNA splicing endonuclease in the presence of the compound or the compound from the library of compounds is not altered relative to the amount of substrate cleaved by the animalia tRNA splicing endonuclease in the absence of the compound or the compound from the library of compounds or the presence of a negative control.

9. The method of claim 3, wherein the coding region of the reporter gene encodes at least one or more coding regions of the reporter genes from the group consisting of firefly luciferase, renilla luciferase, click beetle luciferase, green fluorescent protein, yellow fluorescent protein, red fluorescent protein, cyan fluorescent protein, blue fluorescent protein, beta-galactosidase, beta-glucoronidase, beta-lactamase, chloramphenicol acetyltransferase, and alkaline phosphatase.

10. The method of claim 3, wherein the fungal cell is a yeast cell.

11. The method of claim 10, wherein the yeast cell is a *Saccharomyces cerevisiae* cell, a *Schizosaccharomyces pombe* cell, a *Pichia pastoris* cell, or a *Hansenula polymorpha* cell.

12. The method of claim 1, 2 or 3, wherein the tRNA intron is in the coding region of the reporter gene.

* * * * *

UNITED STATES PATENT AND TRADEMARK OFFICE
CERTIFICATE OF CORRECTION

| | | |
|---|---|---|
| PATENT NO. | : 7,829,503 B2 | Page 1 of 1 |
| APPLICATION NO. | : 10/551304 | |
| DATED | : November 9, 2010 | |
| INVENTOR(S) | : Christopher R. Trotta | |

It is certified that error appears in the above-identified patent and that said Letters Patent is hereby corrected as shown below:

In claim 1, line 5: replace "compounds of compounds" with --compounds--
In claim 2, line 6: replace "compounds or" with --compounds, or--
In claim 3, line 6: replace "compounds or" with --compounds, or--
In claim 6, lines 3-4: replace "polymorphacell" with --polymorpha cell--
In claim 8, line 17: replace "compounds or" with --compounds, or--

Signed and Sealed this
Fifth Day of April, 2011

David J. Kappos
*Director of the United States Patent and Trademark Office*

UNITED STATES PATENT AND TRADEMARK OFFICE
CERTIFICATE OF CORRECTION

PATENT NO. : 7,829,503 B2  
APPLICATION NO. : 10/551304  
DATED : November 9, 2010  
INVENTOR(S) : Christopher R. Trotta Page 1 of 1

It is certified that error appears in the above-identified patent and that said Letters Patent is hereby corrected as shown below:

Column 75, line 16 (claim 1, line 5) replace "compounds of compounds" with --compounds--
Column 75, line 42 (claim 2, line 6) replace "compounds or" with --compounds, or--
Column 75, line 51 (claim 3, line 6) replace "compounds or" with --compounds, or--
Column 76, lines 5-6 (claim 6, lines 3-4) replace "polymorphacell" with --polymorpha cell--
Column 76, line 41 (claim 8, line 17) replace "compounds or" with --compounds, or--

This certificate supersedes the Certificate of Correction issued April 5, 2011.

Signed and Sealed this
Third Day of May, 2011

David J. Kappos
*Director of the United States Patent and Trademark Office*